US006902921B2

(12) United States Patent
Srinivasan et al.

(10) Patent No.: US 6,902,921 B2
(45) Date of Patent: Jun. 7, 2005

(54) SULFURYLASE-LUCIFERASE FUSION PROTEINS AND THERMOSTABLE SULFURYLASE

(75) Inventors: Maithreyan Srinivasan, Hamden, CT (US); Michael Reifler, Hamden, CT (US)

(73) Assignee: 454 Corporation, Branford, CT (US)

( * ) Notice: Subject to any disclaimer, the term of this patent is extended or adjusted under 35 U.S.C. 154(b) by 0 days.

(21) Appl. No.: 10/154,515

(22) Filed: May 23, 2002

(65) Prior Publication Data

US 2003/0113747 A1 Jun. 19, 2003

Related U.S. Application Data

(63) Continuation-in-part of application No. 10/122,706, filed on Apr. 11, 2002.
(60) Provisional application No. 60/335,949, filed on Oct. 30, 2001, and provisional application No. 60/349,076, filed on Jan. 16, 2002.

(51) Int. Cl.[7] .......................... C12N 9/12; C12N 9/02; C12P 21/04; C07H 21/04
(52) U.S. Cl. ..................... 435/194; 435/69.7; 435/189; 536/23.2; 536/23.4
(58) Field of Search ............................... 435/194, 69.7, 435/189, 193; 536/23.2, 23.4

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,822,746 A | 4/1989 | Walt |
| 4,863,849 A | 9/1989 | Melamede |
| 4,873,316 A | 10/1989 | Meade et al. |
| 4,965,188 A | 10/1990 | Mullis et al. |
| 4,971,903 A | 11/1990 | Hyman |
| 5,114,984 A | 5/1992 | Branch et al. |
| 5,143,853 A | 9/1992 | Walt |
| 5,244,636 A | 9/1993 | Walt et al. |
| 5,250,264 A | 10/1993 | Walt et al. |
| 5,252,494 A | 10/1993 | Walt |
| 5,254,477 A | 10/1993 | Walt |
| 5,298,741 A | 3/1994 | Walt et al. |
| 5,320,814 A | 6/1994 | Walt et al. |
| 5,405,746 A | 4/1995 | Uhlen |
| 5,429,807 A | 7/1995 | Matson et al. |
| 5,436,327 A | 7/1995 | Southern et al. |
| 5,445,934 A | 8/1995 | Fodor et al. |
| 5,512,490 A | 4/1996 | Walt et al. |
| 5,534,424 A | 7/1996 | Uhlen et al. |
| 5,633,972 A | 5/1997 | Walt et al. |
| 5,648,245 A | 7/1997 | Fire et al. |
| 5,700,637 A | 12/1997 | Southern |
| 5,714,320 A | 2/1998 | Kool |
| 5,716,785 A | 2/1998 | Van Gelder et al. |
| 5,744,305 A | 4/1998 | Fodor et al. |
| 5,750,341 A | 5/1998 | Macevicz |
| 5,770,367 A | 6/1998 | Southern et al. |
| 5,780,231 A | 7/1998 | Brenner |
| 5,795,716 A | 8/1998 | Chee et al. |
| 5,800,992 A | 9/1998 | Fodor et al. |
| 5,814,524 A | 9/1998 | Walt et al. |
| 5,854,033 A | 12/1998 | Lizardi |
| 5,871,928 A | 2/1999 | Fodor et al. |
| 5,891,636 A | 4/1999 | Van Gelder et al. |
| 5,900,481 A | 5/1999 | Lough et al. |
| 5,962,228 A | 10/1999 | Brenner |
| 6,013,445 A | 1/2000 | Albrecht et al. |
| 6,023,540 A | 2/2000 | Walt et al. |
| 6,040,193 A | 3/2000 | Winkler et al. |
| 6,054,270 A | 4/2000 | Southern |
| 6,080,585 A | 6/2000 | Southern et al. |
| 6,114,114 A | 9/2000 | Seilhamer et al. |
| 6,133,436 A | 10/2000 | Koster et al. |
| 6,136,543 A | 10/2000 | Anazawa et al. |
| 6,150,095 A | 11/2000 | Southern et al. |
| 6,200,737 B1 | 3/2001 | Walt et al. |
| 6,210,891 B1 | 4/2001 | Nyren et al. |
| 6,210,896 B1 | 4/2001 | Chan |
| 6,210,910 B1 | 4/2001 | Walt et al. |
| 6,218,111 B1 | 4/2001 | Southern et al. |
| 6,221,653 B1 | 4/2001 | Caren et al. |
| 6,255,476 B1 | 7/2001 | Vinayak et al. |
| 6,258,568 B1 | 7/2001 | Nyren |
| 6,263,286 B1 | 7/2001 | Gilmanshin et al. |
| 6,274,320 B1 | 8/2001 | Rothberg et al. |
| 6,306,597 B1 | 10/2001 | Macevicz |
| 6,307,039 B1 | 10/2001 | Southern |
| 6,333,155 B1 | 12/2001 | Lockhart et al. |
| 6,355,420 B1 | 3/2002 | Chan |
| 6,355,431 B1 | 3/2002 | Chee et al. |
| 2001/0006630 A1 | 7/2001 | Yacoby-Zeevi |
| 2001/0041335 A1 | 11/2001 | Goldberg et al. |
| 2002/0009729 A1 | 1/2002 | McGall et al. |
| 2002/0022721 A1 | 2/2002 | Trulson et al. |

FOREIGN PATENT DOCUMENTS

| | | |
|---|---|---|
| EP | 0 264 166 | 4/1988 |
| EP | 0 373 203 | 8/1994 |
| EP | 0 619 321 | 1/1999 |
| WO | WO 89/10977 | 11/1989 |

(Continued)

OTHER PUBLICATIONS

Baldwin. Structure (Mar. 15, 1996) vol. 4, pp. 223–228.*
Schauer. TIBTECH (Jan. 1988) vol. 6, pp. 23–27.*

(Continued)

*Primary Examiner*—Elizabeth Slobodyansky
(74) *Attorney, Agent, or Firm*—Mintz Levin Cohn Ferris Glovsky and Popeo PC; Ivor R. Elrifi

(57) ABSTRACT

The present invention relates to the field of DNA recombinant technology. More specifically, this invention relates to fusion proteins comprising an ATP generating polypeptide joined to a polypeptide that converts ATP into a detectable entity. Accordingly, this invention focuses on sulfurylase-luciferase fusion proteins. This invention also relates to pharmaceutical compositions containing the fusion proteins and methods for using them.

8 Claims, 3 Drawing Sheets

FOREIGN PATENT DOCUMENTS

| | | |
|---|---|---|
| WO | WO 98/13523 | 4/1998 |
| WO | WO 98/28440 | 7/1998 |
| WO | WO 98/35012 | 8/1998 |
| WO | WO 98/53300 | 11/1998 |
| WO | WO 99/05315 | 2/1999 |
| WO | WO 99/60007 | 11/1999 |
| WO | WO 99/61662 | 12/1999 |
| WO | WO 99/66313 | 12/1999 |
| WO | WO 99/67641 | 12/1999 |
| WO | WO 00/06770 | 2/2000 |
| WO | WO 00/27521 | 5/2000 |
| WO | WO 00/39587 | 7/2000 |
| WO | WO 00/43540 | 7/2000 |
| WO | WO 00/44491 | 8/2000 |
| WO | WO 00/47996 | 8/2000 |
| WO | WO 00/48000 | 8/2000 |
| WO | WO 00/56455 | 9/2000 |
| WO | WO 00/58507 | 10/2000 |
| WO | WO 00/60072 | 10/2000 |
| WO | WO 00/60114 | 10/2000 |
| WO | WO 00/63437 | 10/2000 |
| WO | WO 00/71243 | 11/2000 |
| WO | WO 00/71992 | 11/2000 |
| WO | WO 00/71995 | 11/2000 |
| WO | WO 00/75373 | 12/2000 |
| WO | WO 01/18524 | 3/2001 |
| WO | WO 01/24937 | 4/2001 |
| WO | WO 01/25480 | 4/2001 |
| WO | WO 01/42496 | 6/2001 |
| WO | WO 01/46675 | 6/2001 |
| WO | WO 01/57268 | 8/2001 |
| WO | WO 01/57269 | 8/2001 |
| WO | WO 01/59432 | 8/2001 |
| WO | WO 01/61043 | 8/2001 |
| WO | WO 01/85341 | 11/2001 |
| WO | WO 02/00336 | 1/2002 |
| WO | WO 02/12897 | 2/2002 |
| WO | WO 02/16649 | 2/2002 |
| WO | WO 02/20836 | 3/2002 |
| WO | WO 02/20837 | 3/2002 |
| WO | WO 02/21128 | 3/2002 |

OTHER PUBLICATIONS

Cherest et al. (1987) Mol. Gen. Genet., vol. 210, pp. 307–313.*
Onda et al. (1996) Bioscience Biotechnology and Biochemistry, vol. 60(10), pp. 1740–1742.*
Baldari et al. (1987). *The EMBO J.* 6: 229–234.
Baner et al. (1998). *Nuc. Acids Res.* 26: 5073–5078.
Banerji et al. (1983). *Cell* 33: 729–740.
Barany (1991). *Proc. Natl. Acad. Sci. USA* 88: 189–193.
Barringer et al. (1990). *Gene* 89: 117–122.
Blum et al. (1989). *J. Bioluminescence and Chemiluminescence* 4: 543–550.
Byrne and Ruddle (1989). *Proc. Natl. Acad. Sci. USA* 86: 5473–5477.
Calame and Eaton (1988). *Adv. In Immunol.* 43: 235–275.
Camper and Tilghman (1989). *Genes & Development* 3: 537–546.
DeWet et al. (1985). *Proc. Natl. Acad. Sci. USA* 82:7870–7873.
DeWet et al. (1987). *Mol. and Cell. Biol.* 7: 725–737.
Edlund et al. (1985). *Science* 230: 912–916.
Fire and Xu (1995). *Proc. Natl. Acad. Sci. USA* 92: 4641–4645.
Ford et al. (1991). *Protein Expression and Purification* 2: 95–107.
Green et al. (1984). *Talanta* 31: 173–176.
Guatelli et al. (1990). *Proc. Natl. Acad. Sci. USA* 87: 1874–1878.
Hawes and Nicholas (1973). *Biochem. J.* 133: 541–550.
Hengsakul and Cass (1996). *Bioconjugate Chem.* 7: 249–254.
Hopp et al. (1988). *Bio/Technology* 6: 1204–1210.
Jha et al. (1990). *FEBS* 274: 23–26.
Kaufman et al. (1987). *The EMBO J.* 6: 187–193.
Keller et al. (1987). *Proc. Natl. Acad. Sci. USA* 84: 3264–3268.
Kessel and Gruss (1990). *Science* 249: 374–379.
Kievits et al. (1991). *J. Virological Methods* 35: 273–286.
Kurjan and Herskowitz (1982). *Cell* 30: 933–943.
Kwoh et al. (1989). *Proc. Natl. Acad. Sci. USA* 86: 1173–1177.
Landegren and Nilsson (1997). *Ann. Med.* 29: 585–590.
Leach (1981). *J. Applied Biochem.* 3: 473–517.
Liu et al. (1996). *J. Am. Chem. Soc.* 118: 1587–1594.
Lizardi et al. (1988). *Bio/Technology* 6: 1197–1202.
Lizardi et al. (1998). *Nature Genetics* 19: 225–232.
Luckow and Summers (1989). *Virology* 170: 31–39.
Nilsson et al. (1985). *The EMBO J.* 4: 1075–1080.
Nilsson et al. (1991). *Methods in Enzymology* 198: 3–16.
Nilsson et al. (1994). *Science* 265: 2085–2087.
Nilsson et al. (1997). *Nature Genetics* 16: 252–255.
Ow et al. (1986). *Science* 234: 856–859.
Pinkert et al. (1987). *Genes & Development* 1: 268–276.
Pirrung and Huang (1996). *Bioconjugate Chem.* 7; 317–321.
Queen and Baltimore (1983). *Cell* 33: 741–748.
Robbins and Lipmann (1958). *J. Biol. Chem.* 233: 686–690.
Ronaghi et al. (1996). *Analytical Biochem.* 242: 84–89.
Ronaghi et al. (1998). *Science* 281: 364–365.
Saiki et al. (1985). *Science* 230: 1350–1354.
Samols et al. (1988). *J. Biol. Chem.* 263: 6461–6464.
Schultz et al. (1987). *Gene* 54: 113–123.
Seed (1987). *Nature* 329: 840–842.
Seliger and McElroy (1960). *Archives of Biochem. and Biophysics* 88: 136–141.
Seubert et al. (1983). *Archives of Biochem. and Biophysics* 225: 679–691.
Seubert et al. (1985). *Archives of Biochem. and Biophysics* 240: 509–523.
Smith and Johnson (1988). *Gene* 67: 31–40.
Smith et al. (1983). *Molecular and Cellular Biol.* 3: 2156–2165.
Walker et al. (1992). *Nuc. Acids Res.* 20: 1691–1696.
Walker et al. (1992). *Proc. Natl. Acad. Sci. USA* 89: 392–396.
Wilson and Bandurski (1958). *J. Biol. Chem.* 233: 975–981.
Winoto and Baltimore (1989). *The EMBO J.* 8: 729–733.
Wood et al. 91989). *J. of Bioluminescence and Chemiluminescence* 4: 289–301.
Wood et al. (1989). *Science* 244: 700–702.
Zhang et al. (1998). *Gene* 211: 277–285.
Hyman (1988). *Analytical Biochem.* 174: 423–436.
Mitra and Church (1999). *Nuc. Acids Res.* 27(e34): i–vi.
Tawfik and Griffiths (1998). *Nature Biotechnol.* 16: 652–656.

* cited by examiner

2A

2B

US 6,902,921 B2

SULFURYLASE-LUCIFERASE FUSION PROTEINS AND THERMOSTABLE SULFURYLASE

CROSS REFERENCE TO RELATED APPLICATIONS

This application claims the benefit of U.S. Ser. No. 60/335,949 filed Oct. 30, 2001; U.S. Pat. No. 60/349,076 filed Jan. 16, 2002; and U.S. Ser. No. 10/122,706 filed Apr. 11, 2002. This application is a continuation-in-part application of U.S. application Ser. No. 10/122,706. The contents of these applications are incorporated herein by reference in their entirety.

FIELD OF THE INVENTION

The invention relates generally to fusion proteins that are useful as reporter proteins, in particular to fusion proteins of ATP sulfurylase and luciferase which are utilized to achieve an efficient conversion of pyrophosphate (PPi) to light. This invention also relates to a novel thermostable sulfurylase which can be used in the detection of inorganic pyrophosphate, particularly in the sequencing of nucleic acid.

BACKGROUND OF THE INVENTION

ATP sulfurylase has been identified as being involved in sulfur metabolism. It catalyzes the initial reaction in the metabolism of inorganic sulfate ($SO_4^{-2}$); see e.g., Robbins and Lipmann, 1958. *J. Biol. Chem.* 233: 686–690; Hawes and Nicholas, 1973. *Biochem. J.* 133: 541–550). In this reaction $SO_4^{-2}$ is activated to adenosine 5'-phosphosulfate (APS). ATP sulfurylase is also commonly used in pyrophosphate sequencing methods. In order to convert pyrophosphate (PPi) generated from the addition of dNMP to a growing DNA chain to light, PPi must first be converted to ATP by ATP sulfurylase.

ATP produced by an ATP sulfurylase can also be hydrolyzed using enzymatic reactions to generate light. Light-emitting chemical reactions (i.e., chemiluminescence) and biological reactions (i.e., bioluminescence) are widely used in analytical biochemistry for sensitive measurements of various metabolites. In bioluminescent reactions, the chemical reaction that leads to the emission of light is enzyme-catalyzed. For example, the luciferin-luciferase system allows for specific assay of ATP. Thus, both ATP generating enzymes, such as ATP sulfurylase, and light emitting enzymes, such as luciferase, could be useful in a number of different assays for the detection and/or concentration of specific substances in fluids and gases. Since high physical and chemical stability is sometimes required for enzymes involved in sequencing reactions, a thermostable enzyme is desirable.

Because the product of the sulfurylase reaction is consumed by luciferase, proximity between these two enzymes by covalently linking the two enzymes in the form of a fusion protein would provide for a more efficient use of the substrate. Substrate channeling is a phenomenon in which substrates are efficiently delivered from enzyme to enzyme without equilibration with other pools of the same substrates. In effect, this creates local pools of metabolites at high concentrations relative to those found in other areas of the cell. Therefore, a fusion of an ATP generating polypeptide and an ATP converting peptide could benefit from the phenomenon of substrate channeling and would reduce production costs and increase the number of enzymatic reactions that occur during a given time period.

All patents and publications cited throughout the specification are hereby incorporated by reference into this specification in their entirety in order to more fully describe the state of the art to which this invention pertains.

SUMMARY OF THE INVENTION

The invention provides a fusion protein comprising an ATP generating polypeptide bound to a polypeptide which converts ATP into an entity which is detectable. In one aspect, the invention provides a fusion protein comprising a sulfurylase polypeptide bound to a luciferase polypeptide. This invention provides a nucleic acid that comprises an open reading frame that encodes a novel thermostable sulfurylase polypeptide. In a further aspect, the invention provides for a fusion protein comprising a thermostable sulfurylase joined to at least one affinity tag.

In another aspect, the invention provides a recombinant polynucleotide that comprises a coding sequence for a fusion protein having a sulfurylase poylpeptide sequence joined to a luciferase polypeptide sequence. In a further aspect, the invention provides an expression vector for expressing a fusion protein. The expression vector comprises a coding sequence for a fusion protein having: (i) a regulatory sequence, (ii) a first polypeptide sequence of an ATP generating polypeptide and (iii) a second polypeptide sequence that converts ATP to an entity which is detectable. In an additional embodiment, the fusion protein comprises a sulfurylase polypeptide and a luciferase polypeptide. In another aspect, the invention provides a transformed host cell which comprises the expression vector. In an additional aspect, the invention provides a fusion protein bound to a mobile support. The invention also includes a kit comprising a sulfurylase-luciferase fusion protein expression vector.

The invention also includes a method for determining the nucleic acid sequence in a template nucleic acid polymer, comprising: (a) introducing the template nucleic acid polymer into a polymerization environment in which the nucleic acid polymer will act as a template polymer for the synthesis of a complementary nucleic acid polymer when nucleotides are added; (b) successively providing to the polymerization environment a series of feedstocks, each feedstock comprising a nucleotide selected from among the nucleotides from which the complementary nucleic acid polymer will be formed, such that if the nucleotide in the feedstock is complementary to the next nucleotide in the template polymer to be sequenced said nucleotide will be incorporated into the complementary polymer and inorganic pyrophosphate will be released; (c) separately recovering each of the feedstocks from the polymerization environment; and (d) measuring the amount of PPi with an ATP generating polypeptide-ATP converting polypeptide fusion protein in each of the recovered feedstocks to determine the identity of each nucleotide in the complementary polymer and thus the sequence of the template polymer. In one embodiment, the amount of inorganic pyrophosphate is measured by the steps of: (a) adding adenosine-5'-phosphosulfate to the feedstock; (b) combining the recovered feedstock containing adenosine-5'-phosphosulfate with an ATP generating polypeptide-ATP converting polypeptide fusion protein such that any inorganic pyrophosphate in the recovered feedstock and the adenosine-5'-phosphosulfate will react to the form ATP and sulfate; (c) combining the ATP and sulfate-containing feedstock with luciferin in the presence of oxygen such that the ATP is consumed to produced AMP, inorganic pyrophosphate, carbon dioxide and light; and (d) measuring the amount of light produced.

In another aspect, the invention includes a method wherein each feedstock comprises adenosine-5'- phosphosulfate and luciferin in addition to the selected nucleotide base, and the amount of inorganic pyrophosphate is determined by reacting the inorganic pyrophosphate feedstock with an ATP generating polypeptide-ATP converting polypeptide fusion protein thereby producing light in an amount proportional to the amount of inorganic pyrophosphate, and measuring the amount of light produced.

In another aspect, the invention provides a method for sequencing a nucleic acid, the method comprising: (a) providing one or more nucleic acid anchor primers; (b) providing a plurality of single-stranded circular nucleic acid templates disposed within a plurality of cavities on a planar surface, each cavity forming an analyte reaction chamber, wherein the reaction chambers have a center to center spacing of between 5 to 200 $\mu$m; (c) annealing an effective amount of the nucleic acid anchor primer to at least one of the single-stranded circular templates to yield a primed anchor primer-circular template complex; (d) combining the primed anchor primer-circular template complex with a polymerase to form an extended anchor primer covalently linked to multiple copies of a nucleic acid complementary to the circular nucleic acid template; (e) annealing an effective amount of a sequencing primer to one or more copies of said covalently linked complementary nucleic acid; (f) extending the sequencing primer with a polymerase and a predetermined nucleotide triphosphate to yield a sequencing product and, if the predetermined nucleotide triphosphate is incorporated onto the 3' end of said sequencing primer, a sequencing reaction byproduct; and (g) identifying the sequencing reaction byproduct with the use of a ATP generating polypeptide-ATP converting polypeptide fusion protein, thereby determining the sequence of the nucleic acid.

In one aspect, the invention provides a method for sequencing a nucleic acid, the method comprising: (a) providing at least one nucleic acid anchor primer; (b) providing a plurality of single-stranded circular nucleic acid templates in an array having at least 400,000 discrete reaction sites; (c) annealing a first amount of the nucleic acid anchor primer to at least one of the single-stranded circular templates to yield a primed anchor primer-circular template complex; (d) combining the primed anchor primer-circular template complex with a polymerase to form an extended anchor primer covalently linked to multiple copies of a nucleic acid complementary to the circular nucleic acid template; (e) annealing a second amount of a sequencing primer to one or more copies of the covalently linked complementary nucleic acid; (f) extending the sequencing primer with a polymerase and a predetermined nucleotide triphosphate to yield a sequencing product and, when the predetermined nucleotide triphosphate is incorporated onto the 3' end of the sequencing primer, to yield a sequencing reaction byproduct; and (g) identifying the sequencing reaction byproduct with the use of a ATP generating polypeptide-ATP converting polypeptide fusion protein, thereby determining the sequence of the nucleic acid at each reaction site that contains a nucleic acid template.

In another aspect, the invention includes a method of determining the base sequence of a plurality of nucleotides on an array, the method comprising the steps of: (a) providing a plurality of sample DNAs, each disposed within a plurality of cavities on a planar surface, each cavity forming an analyte reaction chamber, wherein the reaction chambers have a center to center spacing of between 5 to 200 $\mu$m, (b) adding an activated nucleotide 5'-triphosphate precursor of one known nitrogenous base to a reaction mixture in each reaction chamber, each reaction mixture comprising a template-directed nucleotide polymerase and a single-stranded polynucleotide template hybridized to a complementary oligonucleotide primer strand at least one nucleotide residue shorter than the templates to form at least one unpaired nucleotide residue in each template at the 3'-end of the primer strand, under reaction conditions which allow incorporation of the activated nucleoside 5'-triphosphate precursor onto the 3'-end of the primer strands, provided the nitrogenous base of the activated nucleoside 5'-triphosphate precursor is complementary to the nitrogenous base of the unpaired nucleotide residue of the templates; (c) determining whether or not the nucleoside 5'-triphosphate precursor was incorporated into the primer strands through detection of a sequencing byproduct with a ATP generating polypeptide-ATP converting polypeptide fusion protein, thus indicating that the unpaired nucleotide residue of the template has a nitrogenous base composition that is complementary to that of the incorporated nucleoside 5'-triphosphate precursor; and (d) sequentially repeating steps (b) and (c), wherein each sequential repetition adds and, detects the incorporation of one type of activated nucleoside 5'-triphosphate precursor of known nitrogenous base composition; and (e) determining the base sequence of the unpaired nucleotide residues of the template in each reaction chamber from the sequence of incorporation of said nucleoside precursors.

In one aspect, the invention includes a method for determining the nucleic acid sequence in a template nucleic acid polymer, comprising: (a) introducing a plurality of template nucleic acid polymers into a plurality of cavities on a planar surface, each cavity forming an analyte reaction chamber, wherein the reaction chambers have a center to center spacing of between 5 to 200 $\mu$m, each reaction chamber having a polymerization environment in which the nucleic acid polymer will act as a template polymer for the synthesis of a complementary nucleic acid polymer when nucleotides are added; (b) successively providing to the polymerization environment a series of feedstocks, each feedstock comprising a nucleotide selected from among the nucleotides from which the complementary nucleic acid polymer will be formed, such that if the nucleotide in the feedstock is complementary to the next nucleotide in the template polymer to be sequenced said nucleotide will be incorporated into the complementary polymer and inorganic pyrophosphate will be released; (c) detecting the formation of inorganic pyrophosphate with an ATP generating polypeptide-ATP converting polypeptide fusion protein to determine the identify of each nucleotide in the complementary polymer and thus the sequence of the template polymer.

In one aspect, the invention provides a method of identifying the base in a target position in a DNA sequence of sample DNA including the steps comprising: (a) disposing sample DNA within a plurality of cavities on a planar surface, each cavity forming an analyte reaction chamber, wherein the reaction chambers have a center to center spacing of between 5 to 200 $\mu$m, said DNA being rendered single stranded either before or after being disposed in the reaction chambers, (b) providing an extension primer which hybridizes to said immobilized single-stranded DNA at a position immediately adjacent to said target position; (c) subjecting said immobilized single-stranded DNA to a polymerase reaction in the presence of a predetermined nucleotide triphosphate, wherein if the predetermined nucleotide triphosphate is incorporated onto the 3' end of said sequencing primer then a sequencing reaction byproduct is formed; and (d) identifying the sequencing reaction byproduct with a ATP generating polypeptide-ATP converting polypeptide fusion protein, thereby determining the nucleotide complementary to the base at said target position.

The invention also includes a method of identifying a base at a target position in a sample DNA sequence comprising: (a) providing sample DNA disposed within a plurality of cavities on a planar surface, each cavity forming an analyte reaction chamber, wherein the reaction chambers have a center to center spacing of between 5 to 200 µm, said DNA being rendered single stranded either before or after being disposed in the reaction chambers; (b) providing an extension primer which hybridizes to the sample DNA immediately adjacent to the target position; (c) subjecting the sample DNA sequence and the extension primer to a polymerase reaction in the presence of a nucleotide triphosphate whereby the nucleotide triphosphate will only become incorporated and release pyrophosphate (PPi) if it is complementary to the base in the target position, said nucleotide triphosphate being added either to separate aliquots of sample-primer mixture or successively to the same sample-primer mixture; (d) detecting the release of PPi with an ATP generating polypeptide-ATP converting polypeptide fusion protein to indicate which nucleotide is incorporated.

In one aspect, the invention provides a method of identifying a base at a target position in a single-stranded sample DNA sequence, the method comprising: (a) providing an extension primer which hybridizes to sample DNA immediately adjacent to the target position, said sample DNA disposed within a plurality of cavities on a planar surface, each cavity forming an analyte reaction chamber, wherein the reaction chambers have a center to center spacing of between 5 to 200 um, said DNA being rendered single stranded either before or after being disposed in the reaction chambers; (b) subjecting the sample DNA and extension primer to a polymerase reaction in the presence of a predetermined deoxynucleotide or dideoxynucleotide whereby the deoxynucleotide or dideoxynucleotide will only become incorporated and release pyrophosphate (PPi) if it is complementary to the base in the target position, said predetermined deoxynucleotides or dideoxynucleotides being added either to separate aliquots of sample-primer mixture or successively to the same sample-primer mixture, (c) detecting any release of PPi with an ATP generating polypeptide-ATP converting polypeptide fusion protein to indicate which deoxynucleotide or dideoxynucleotide is incorporated;characterized in that, the PPi-detection enzyme(s) are included in the polymerase reaction step and in that in place of deoxy- or dideoxy adenosine triphosphate (ATP) a dATP or ddATP analogue is used which is capable of acting as a substrate for a polymerase but incapable of acting as a substrate for a said PPi—detection enzyme.

In another aspect, the invention includes a method of determining the base sequence of a plurality of nucleotides on an array, the method comprising: (a) providing a plurality of sample DNAs, each disposed within a plurality of cavities on a planar surface, each cavity forming an analyte reaction chamber, wherein the reaction chambers have a center to center spacing of between 5 to 200 µm, (b) converting PPi into light with an ATP generating polypeptide-ATP converting polypeptide fusion protein; (c) detecting the light level emitted from a plurality of reaction sites on respective portions of an optically sensitive device; (d) converting the light impinging upon each of said portions of said optically sensitive device into an electrical signal which is distinguishable from the signals from all of said other regions; (e) determining a light intensity for each of said discrete regions from the corresponding electrical signal; (f) recording the variations of said electrical signals with time.

In one aspect, the invention provides a method for sequencing a nucleic acid, the method comprising:(a) providing one or more nucleic acid anchor primers; (b) providing a plurality of single-stranded circular nucleic acid templates disposed within a plurality of cavities on a planar surface, each cavity forming an analyte reaction chamber, wherein the reaction chambers have a center to center spacing of between 5 to 200 µm;(c) converting PPi into a detectable entity with the use of an ATP generating polypeptide-ATP converting polypeptide fusion protein; (d) detecting the light level emitted from a plurality of reaction sites on respective portions of an optically sensitive device; (e) converting the light impinging upon each of said portions of said optically sensitive device into an electrical signal which is distinguishable from the signals from all of said other regions; (f) determining a light intensity for each of said discrete regions from the corresponding electrical signal; (g) recording the variations of said electrical signals with time.

In another aspect, the invention includes a method for sequencing a nucleic acid, the method comprising: (a) providing at least one nucleic acid anchor primer; (b) providing a plurality of single-stranded circular nucleic acid templates in an array having at least 400,000 discrete reaction sites; (c) converting PPi into a detectable entity with an ATP generating polypeptide-ATP converting polypeptide fusion protein; (d) detecting the light level emitted from a plurality of reaction sites on respective portions of an optically sensitive device; (e) converting the light impinging upon each of said portions of said optically sensitive device into an electrical signal which is distinguishable from the signals from all of said other regions; (f) determining a light intensity for each of said discrete regions from the corresponding electrical signal; (g) recording the variations of said electrical signals with time.

In another aspect, the invention includes an isolated polypeptide comprising an amino acid sequence selected from the group consisting of: (a) a mature form of an amino acid sequence of SEQ ID NO: 2; (b) a variant of a mature form of an amino acid sequence of SEQ ID NO: 2; an amino acid sequence of SEQ ID NO: 2; (c) a variant of an amino acid sequence of SEQ ID NO: 2, wherein one or more amino acid residues in said variant differs from the amino acid sequence of said mature form, provided that said variant differs in no more than 5% of amino acid residues from said amino acid sequence; (d) and at least one conservative amino acid substitution to the amino acid sequences in (a), (b), (c) or (d). The invention also includes an antibody that binds immunospecifically to the polypeptide of (a), (b), (c) or (d).

In another aspect, the invention includes an isolated nucleic acid molecule comprising a nucleic acid sequence encoding a polypeptide comprising an amino acid sequence selected from the group consisting of: (a) a mature form of an amino acid sequence of SEQ ID NO: 2; (b) a variant of a mature form of an amino acid sequence of SEQ ID NO: 2, wherein one or more amino acid residues in said variant differs from the amino acid sequence of said mature form, provided that said variant differs in no more than 5% of the amino acid residues from the amino acid sequence of said mature form; (c) an amino acid sequence of SEQ ID NO: 2; (d) a variant of an amino acid sequence of SEQ ID NO: 2, wherein one or more amino acid residues in said variant differs from the amino acid sequence of said mature form, provided that said variant differs in no more than 15% of amino acid residues from said amino acid sequence; a nucleic acid fragment encoding at least a portion of a polypeptide comprising an amino acid sequence of SEQ ID NO: 2, or a variant of said polypeptide, wherein one or more amino acid residues in said variant differs from the amino acid sequence of said mature form, provided that said variant differs in no more than 5% of amino acid residues from said amino acid sequence; (e) and a nucleic acid molecule comprising the complement of (a), (b), (c), (d) or (e).

In a further aspect, the invention provides a nucleic acid molecule wherein the nucleic acid molecule comprises nucleotide sequence selected from the group consisting of: (a) a first nucleotide sequence comprising a coding sequence differing by one or more nucleotide sequences from a coding sequence encoding said amino acid sequence, provided that no more than 20% of the nucleotides in the coding sequence in said first nucleotide sequence differ from said coding sequence; an isolated second polynucleotide that is a complement of the first polynucleotide; (b) and a nucleic acid fragment of (a) or (b). The invention also includes a vector comprising the nucleic acid molecule of (a) or (b). In another aspect, the invention includes a cell comprising the vector.

In a further aspect, the invention includes a method for determining the nucleic acid sequence in a template nucleic acid polymer, comprising: (a) introducing the template nucleic acid polymer into a polymerization environment in which the nucleic acid polymer will act as a template polymer for the synthesis of a complementary nucleic acid polymer when nucleotides are added; (b) successively providing to the polymerization environment a series of feedstocks, each feedstock comprising a nucleotide selected from among the nucleotides from which the complementary nucleic acid polymer will be formed, such that if the nucleotide in the feedstock is complementary to the next nucleotide in the template polymer to be sequenced said nucleotide will be incorporated into the complementary polymer and inorganic pyrophosphate will be released; (c) separately recovering each of the feedstocks from the polymerization environment; and (d) measuring the amount of PPi with an ATP sulfurylase and a luciferase in each of the recovered feedstocks to determine the identity of each nucleotide in the complementary polymer and thus the sequence of the template polymer.

In another aspect, the invention provides a method for sequencing a nucleic acid, the method comprising: (a) providing one or more nucleic acid anchor primers; (b) providing a plurality of single-stranded circular nucleic acid templates disposed within a plurality of cavities in an array on a planar surface, each cavity forming an analyte reaction chamber, wherein the reaction chambers have a center to center spacing of between 5 to 200 $\mu$m and at least 400,000 discrete sites; (c) annealing an effective amount of the nucleic acid anchor primer to at least one of the single-stranded circular templates to yield a primed anchor primer-circular template complex; (d) combining the primed anchor primer-circular template complex with a polymerase to form an extended anchor primer covalently linked to multiple copies of a nucleic acid complementary to the circular nucleic acid template; (e) annealing an effective amount of a sequencing primer to one or more copies of said covalently linked complementary nucleic acid; (f) extending the sequencing primer with a polymerase and a predetermined nucleotide triphosphate to yield a sequencing product and, if the predetermined nucleotide triphosphate is incorporated onto the 3' end of said sequencing primer, a sequencing reaction byproduct; and (g) identifying the sequencing reaction byproduct with the use of an ATP sulfurylase and a luciferase, thereby determining the sequence of the nucleic acid.

In another aspect, the invention provides a method for sequencing a nucleic acid, the method comprising: (a) providing at least one nucleic acid anchor primer; (b) providing a plurality of single-stranded circular nucleic acid templates in an array having at least 400,000 discrete reaction sites; (c) annealing a first amount of the nucleic acid anchor primer to at least one of the single-stranded circular templates to yield a primed anchor primer-circular template complex; (d) combining the primed anchor primer-circular template complex with a polymerase to form an extended anchor primer covalently linked to multiple copies of a nucleic acid complementary to the circular nucleic acid template; (e) annealing a second amount of a sequencing primer to one or more copies of the covalently linked complementary nucleic acid; (f) extending the sequencing primer with a polymerase and a predetermined nucleotide triphosphate to yield a sequencing product and, when the predetermined nucleotide triphosphate is incorporated onto the 3' end of the sequencing primer, to yield a sequencing reaction byproduct; and (g) identifying the sequencing reaction byproduct with the use of a thermostable sulfurylase and a luciferase, thereby determining the sequence of the nucleic acid at each reaction site that contains a nucleic acid template.

In a further aspect, the invention includes a method of determining the base sequence of a plurality of nucleotides on an array, the method comprising: (a) providing a plurality of sample DNAs, each disposed within a plurality of cavities on a planar surface, each cavity forming an analyte reaction chamber, wherein the reaction chambers have a center to center spacing of between 5 to 200 $\mu$m, (b) adding an activated nucleotide 5'-triphosphate precursor of one known nitrogenous base to a reaction mixture in each reaction chamber, each reaction mixture comprising a template-directed nucleotide polymerase and a single-stranded polynucleotide template hybridized to a complementary oligonucleotide primer strand at least one nucleotide residue shorter than the templates to form at least one unpaired nucleotide residue in each template at the 3'-end of the primer strand, under reaction conditions which allow incorporation of the activated nucleoside 5'-triphosphate precursor onto the 3'-end of the primer strands, provided the nitrogenous base of the activated nucleoside 5'-triphosphate precursor is complementary to the nitrogenous base of the unpaired nucleotide residue of the templates; (c) detecting whether or not the nucleoside 5'-triphosphate precursor was incorporated into the primer strands through detection of a sequencing byproduct with a thermostable sulfurylase and luciferase, thus indicating that the unpaired nucleotide residue of the template has a nitrogenous base composition that is complementary to that of the incorporated nucleoside 5'-triphosphate precursor; and (d) sequentially repeating steps (b) and (c), wherein each sequential repetition adds and, detects the incorporation of one type of activated nucleoside 5'-triphosphate precursor of known nitrogenous base composition; and (e) determining the base sequence of the unpaired nucleotide residues of the template in each reaction chamber from the sequence of incorporation of said nucleoside precursors.

DETAILED DESCRIPTION OF THE INVENTION

Figure 1:
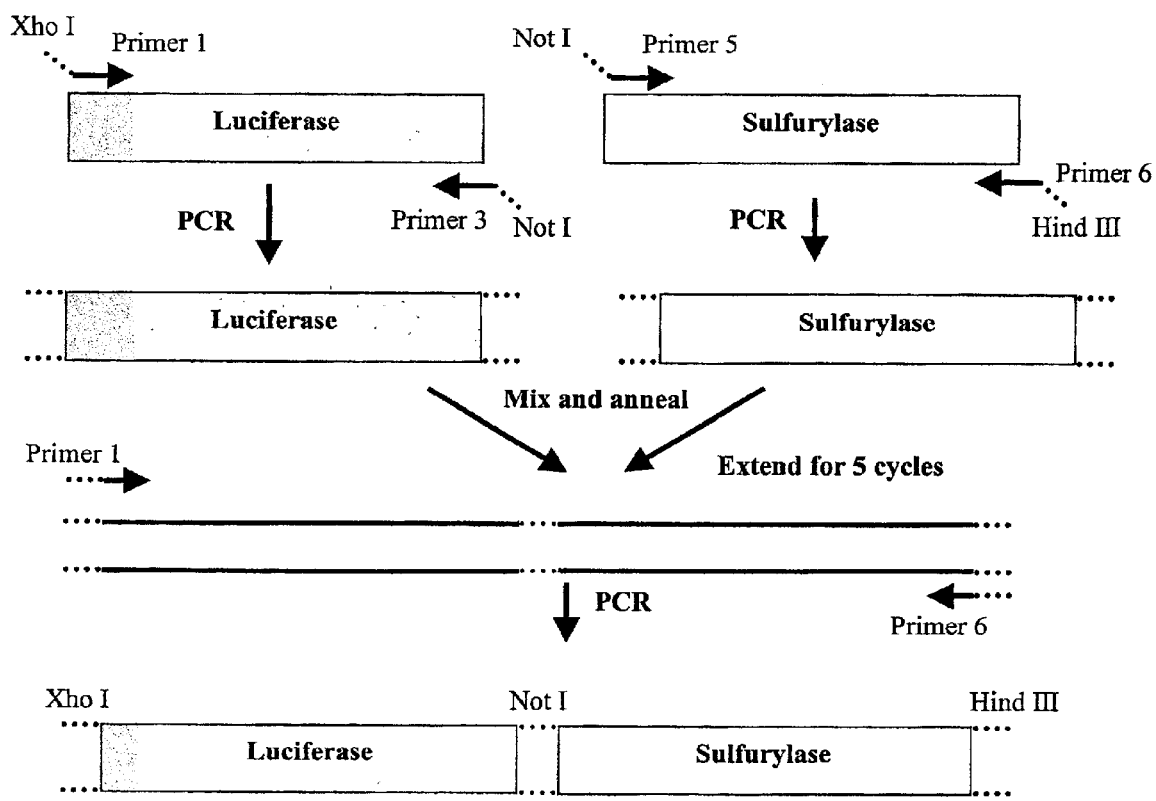
FIG. 1 is one embodiment for a cloning strategy for obtaining the luciferase-sulfurylase sequence.

This invention provides a fusion protein containing an ATP generating polypeptide bound to a polypeptide which converts ATP into an entity which is detectable. As used herein, the term "fusion protein" refers to a chimeric protein containing an exogenous protein fragment joined to another exogenous protein fragment. The fusion protein could include an affinity tag to allow attachment of the protein to a solid support or to allow for purification of the recombinant fusion protein from the host cell or culture supernatant, or both.

In a preferred embodiment, the ATP generating polypeptide and ATP converting polypeptide are from a eukaryote or a prokaryote. The eukaryote could be an animal, plant, fungus or yeast. In some embodiments, the animal is a mammal, rodent, insect, worm, mollusk, reptile, bird and amphibian. Plant sources of the polypeptides include but are not limited to *Arabidopsis thaliana, Brassica napus, Allium sativum, Amaranthus caudatus, Hevea brasiliensis, Hordeum vulgare, Lycopersicon esculentum, Nicotiana tabacum, Oryza sativum, Pisum sativum, Populus trichocarpa, Solanum tuberosum, Secale cereale, Sambucus nigra, Ulmus americana* or *Triticum aestivum*. Examples of fungi include but are not limited to *Penicillum chrysogenum, Stachybotrys chartarum, Aspergillus fumigatus, Podospora anserina* and *Trichoderma reesei*. Examples of sources of yeast include but are not limited to *Saccharomyces cerevisiae, Candida tropicalis, Candida lypolitica, Candida utilis, Kluyveromyces lactis, Schizosaccharomyces pombe, Yarrowia lipolytica, Candida* spp., *Pichia* spp. and *Hansenula* spp.

The prokaryote source could be bacteria or archaea. In some embodiments, the bacteria *E. coli, B. subtilis, Streptococcus gordonii*, flavobacteria or green sulfur bacteria. In other embodiments, the archaea is *Sufolobus, Thermococcus, Methanobacterium, Halococcus, Halobacterium* or *Methanococcus jannaschii*.

The ATP generating polypeptide can be a ATP sulfurylase, hydrolase or an ATP synthase. In a preferred embodiment, the ATP generating polypeptide is ATP sulfurylase. In one embodiment, the ATP sulfurylase is a thermostable sulfurylase cloned from *Bacillus stearothermophilus* (Bst) and comprising the nucleotide sequence of SEQ ID NO: 1. This putative gene was cloned using genomic DNA acquired from ATCC (Cat. No. 12980D). The gene is shown to code for a functional ATP sulfurylase that can be expressed as a fusion protein with an affinity tag. The disclosed Bst sulfurylase nucleic acid (SEQ ID NO: 1) includes the 1247 nucleotide sequence. An open reading frame (ORF) for the mature protein was identified beginning with an ATG codon at nucleotides 1–3 and ending with a TAA codon at nucleotides 1159–1161. The start and stop codons of the open reading frame are highlighted in bold type. The putative untranslated regions are underlined and found upstream of the initiation codon and downstream from the termination codon.

| Bst Thermostable Sulfurylase Nucleotide Sequence | | |
|---|---|---|
| <u>GTTATGAAC</u>ATGAGTTTGAGCATTCCGCATGGCGGCACATTGATCAACCGTTGGAATCCG | 60 | (SEQ ID NO:1) |
| GATTACCCAATCGATGAAGCAACGAAAACGATCGAGCTGTCCAAAGCCGAACTAAGCGAC | 120 | |
| CTTGAGCTGATCGGCACAGGCGCCTACAGCCCGCTCACCGGGTTTTTAACGAAAGCCGAT | 180 | |
| TACGATGCGGTCGTAGAAACGATGCGCCTCGCTGATGGCACTGTCTGGAGCATTCCGATC | 240 | |
| ACGCTGGCGGTGACGGAAGAAAAAGCGAGTGAACTCACTGTCGGCGACAAAGCGAAACTC | 300 | |
| GTTTATGGCGGCGACGTCTACGGCGTCATTGAAATCGCCGATATTTACCGCCCGGATAAA | 360 | |
| ACGAAAGAAGCCAAGCTCGTCTATAAAACCGATGAACTCGCTCACCCGGGCGTGCGCAAG | 420 | |
| CTGTTTGAAAAACCAGATGTGTACGTCGGCGGAGCGGTTACGCTCGTCAAACGGACCGAC | 480 | |
| AAAGGCCAGTTTGCTCCGTTTTATTTCGATCCGGCCGAAACGCGGAAACGATTTGCCGAA | 540 | |
| CTCGGCTGGAATACCGTCGTCGGCTTCCAAACACGCAACCCGGTTCACCGCGCCCATGAA | 600 | |
| TACATTCAAAAATGCGCGCTTGAAATCGTGGACGGCTTGTTTTTAAACCCGCTCGTCGGC | 660 | |
| GAAACGAAAGCGGACGATATTCCGGCCGACATCCGGATGGAAAGCTATCAAGTGCTGCTG | 720 | |
| GAAAACTATTATCCGAAAGACCGCGTTTTCTTGGGCGTCTTCCAAGCTGCGATGCGCTAT | 780 | |
| GCCGGTCCGCGCGAAGCGATTTTCCATGCCATGGTGCGGAAAAACTTCGGCTGCACGCAC | 840 | |
| TTCATCGTCGGCCGCGACCATGCGGGCGTCGGCAACTATTACGGCACGTATGATGCGCAA | 900 | |
| AAAATCTTCTCGAACTTTACAGCCGAAGAGCTTGGCATTACACCGCTCTTTTTCGAACAC | 960 | |
| AGCTTTTATTGCACGAAATGCGAAGGCATGGCATCGACGAAAACATGCCCGCACGACGCA | 1020 | |
| CAATATCACGTTGTCCTTTCTGGCACGAAAGTCCGTGAAATGTTGCGTAACGGCCAAGTG | 1080 | |
| CCGCCGAGCACATTCAGCCGTCCGGAAGTGGCCGCCGTTTTGATCAAAGGGCTGCAAGAA | 1140 | |

| Bst Thermostable Sulfurylase Nucleotide Sequence |
| --- |
| CGCGAAACGGTCACCCCGTCGACACGCTAAAGGAGGAGCGAGATGAGCACGAATATCGTT 1200 |
| TGGCATCATACATCGGTGACAAAAGAAGATCGCCGCCAACGCAACGG 1247 |

The Bst sulfurylase polypeptide (SEQ ID NO:2) is 386 amino acid residues in length and is presented using the three letter amino acid code.

| Bst Sulfurylase Amino Acid Sequence |
| --- |
| Met Ser Leu Ser Ile Pro His Gly Gly Thr Leu Ile Asn Arg Trp Asn  (SEQ ID NO:2)
1               5                   10                  15 |
| Pro Asp Tyr Pro Ile Asp Glu Ala Thr Lys Thr Ile Glu Leu Ser Lys
                20                  25                  30 |
| Ala Glu Leu Ser Asp Leu Glu Leu Ile Gly Thr Gly Ala Tyr Ser Pro
            35                  40                  45 |
| Leu Thr Gly Phe Leu Thr Lys Ala Asp Tyr Asp Ala Val Val Glu Thr
        50                  55                  60 |
| Met Arg Leu Ala Asp Gly Thr Val Trp Ser Ile Pro Ile Thr Leu Ala
    65                  70                  75 |
| Val Thr Glu Glu Lys Ala Ser Glu Leu Thr Val Gly Asp Lys Ala Lys
80                  85                  90                  95 |
| Leu Val Tyr Gly Gly Asp Val Tyr Gly Val Ile Glu Ile Ala Asp Ile
                100                 105                 110 |
| Tyr Arg Pro Asp Lys Thr Lys Glu Ala Lys Leu Val Tyr Lys Thr Asp
            115                 120                 125 |
| Glu Leu Ala His Pro Gly Val Arg Lys Leu Phe Glu Lys Pro Asp Val
        130                 135                 140 |
| Tyr Val Gly Gly Ala Val Thr Leu Val Lys Arg Thr Asp Lys Gly Gln
    145                 150                 155 |
| Phe Ala Pro Phe Tyr Phe Asp Pro Ala Glu Thr Arg Lys Arg Phe Ala
160                 165                 170                 175 |
| Glu Leu Gly Trp Asn Thr Val Val Gly Phe Gln Thr Arg Asn Pro Val
                180                 185                 190 |
| His Arg Ala His Glu Tyr Ile Gln Lys Cys Ala Leu Glu Ile Val Asp
            195                 200                 205 |
| Gly Leu Phe Leu Asn Pro Leu Val Gly Glu Thr Lys Ala Asp Asp Ile
        210                 215                 220 |
| Pro Ala Asp Ile Arg Met Glu Ser Tyr Gln Val Leu Leu Glu Asn Tyr
    225                 230                 235 |
| Tyr Pro Lys Asp Arg Val Phe Leu Gly Val Phe Gln Ala Ala Met Arg
240                 245                 250                 255 |
| Tyr Ala Gly Pro Arg Glu Ala Ile Phe His Ala Met Val Arg Lys Asn
                260                 265                 270 |
| Phe Gly Cys Thr His Phe Ile Val Gly Arg Asp His Ala Gly Val Gly
            275                 280                 285 |
| Asn Tyr Tyr Gly Thr Tyr Asp Ala Gln Lys Ile Phe Ser Asn Phe Thr
        290                 295                 300 |

-continued

Bst Sulfurylase Amino Acid Sequence

Ala Glu Glu Leu Gly Ile Thr Pro Leu Phe Phe Glu His Ser Phe Tyr
    305                 310                 315

Cys Thr Lys Cys Glu Gly Met Ala Ser Thr Lys Tbr Cys Pro His Asp
320                 325                 330                 335

Ala Gln Tyr His Val Val Leu Ser Gly Thr Lys Val Arg Glu Met Leu
                340                 345                 350

Arg Asn Gly Gln Val Pro Pro Ser Thr Phe Ser Arg Pro Glu Val Ala
            355                 360                 365

Ala Val Leu Ile Lys Gly Leu Gln Glu Arg Glu Thr Val Thr Pro Ser
        370                 375                 380

Thr Arg
    385

In one embodiment, the thermostable sulfurylase is active at temperatures above ambient to at least 50° C. This property is beneficial so that the sulfurylase will not be denatured at higher temperatures commonly utilized in polymerase chain reaction (PCR) reactions or sequencing reactions. In one embodiment, the ATP sulfurylase is from a thermophile. The thermostable sulfurylase can come from thermophilic bacteria, including but not limited to, *Bacillus stearothermophilus, Thermus thermophilus, Bacillus caldolyticus, Bacillus subtilis, Bacillus thermoleovorans, Pyrococcus furiosus, Sulfolobus acidocaldarius, Rhodothermus obamensis, Aquifex aeolicus, Archaeoglobus fulgidus, Aeropyrum pernix, Pyrobaculum aerophilum, Pyrococcus abyssi, Penicillium chrysogenum, Sulfolobus solfataricus* and *Thermomonospora fusca*.

The homology of twelve ATP sulfurylases can be shown graphically in the ClustalW analysis in Table 1. The alignment is of ATP sulfurylases from the following species: *Bacillus stearothermophilus* (Bst), University of Oklahoma—Strain 10 (Univ of OK), *Aquifex aeolicus* (Aae), *Pyrococcus furiosus* (Pfu), *Sulfolobus solataricus* (Sso), *Pyrobaculum aerophilum* (Pae), *Archaeoglobus fulgidus* (Afu), *Penicillium chrysogenum* (Pch), *Aeropyrum pernix* (Ape), *Saccharomyces cerevisiae* (Sce), and *Thermomonospora fusca* (Tfu).

TABLE 1

ClustalW Analysis of ATP Sulfurylase Amino Acid Sequence

```
                            10        20        30        40        50
                   ....|....|....|....|....|....|....|....|....|....|
        Bst-Sulf   -----MSLSIPHGGTLENRWNPDYP-----IDEATK---------TIESS  31
        Univ of OK -----MSVSIPHGGTLENKWNPDYP-----LDEATK---------TIESS  31
        Aae-Sulf   --------------------------MEKIKYLKS----------IQSS   13
        Pfu-Sulf   ------MVSKPHGGKLERRKAAPRTRERILSEQHEYP--------RVQED   36
        Sso-Sulf   ------MNLIGHG----KVEIVERIKTISDFKELHRIEVK----------   30
        Pae-Sulf   --MPMPAPLEPHGGRLYYNVIEDRDKAAAMIQGLPSIEIEPTLGPDGSPI   48
        Afu-Sulf   --MPLIKTPPPHGGKLKERKVKKRDIAEKMIAGCPTYELKPTTLPDGTPI   48
        Pch-Sulf   -----MAN-APHGGVIKDLEARDAPRQAELAAEAES--LP-----AVTST   37
        Ape-Sulf   MGCSVGLVSRPHGGRLVRRVLSGRREEIFESQYREMP--------RLEVP   42
        Sce-Sulf   -----MP--APHGGIIQDLIARDALKKNELLSEAQSSDIL-----VWNET   38
        Tfu-Sulf   ---------------MSQVSDAVGR----YQLSQLDF--------SE    20

60        70        80        90       100
                   ....|....|....|....|....|....|....|....|....|....|
        Bst-Sulf   KAELSDKELIGTCAYSPLTGETKADKDAVKEIMRLADGTVNSIPITLAV   81
        Univ of OK KAELSDKELIGTCAKSPLTGETKTDKKAVKETMRLSDCTVNSIPKTLAV   81
        Aae-Sulf   QRELSDKELAVCARIPLDRFKGEEDKRNVKSMRLKSGTLEPIPITLPV   63
        Pfu-Sulf   HGRAIDKKNIAHGVKSPLKGFETREDKVEKYMRLSDDTPVWTIPIVLDK   86
        Sso-Sulf   RQLAHKKVSIAYGFLSPLKGEENYEKVKGVKENMRLPNGVKWPIPKVFDY   80
        Pae-Sulf   RNPYRKKMSIAYGFKSPKEGEKTRNKVKKLKERRLLNGWKKPFPKIYDV   98
        Afu-Sulf   RHVYRKKMSKCYGFKSPKEGSKVGNELKRVKNERRLLSEWKKPYPILFDK   98
        Pch-Sulf   ERQLCDKKLIMNGGKSPLEGFKNQADKDRVCKDNRLADGNKKSRPITLDA   87
        Ape-Sulf   LERAIDAKDKARGVKSPLEGFKVDDKLKVKSRMRLKDDLPWTIPIVLDA   92
        Sce-Sulf   PRQLCDKKLILNGGKSPLTGFKNKDDKSKVTDSRLKDCTKWIPITLDK   88
        Tfu-Sulf   AEAIFIKREKAAEFEREKLLESGGKD-S--KVMKREAKKAFWPAPIPFPK   67
```

TABLE 1-continued

ClustalW Analysis of ATP Sulfurylase Amino Acid Sequence

```
                       110       120       130       140       150
                  ....|....|....|....|....|....|....|....|....|....|
Bst-Sulf     TSEKAS--ELTVGDKAKLV-YGGDVY--GKEEIAELYKP-DKTKEAKLVK 125
Univ of OK   TKEKAK--ELAVGDKAKLV-YGGDVY--GVIEIAELYKP-DKTKEAKLVK 125
Aae-Sulf     EKDIAK--DKKEGKWIVLR--DPKNVEIAIMRVEEEYKW-KLEYEAKNVL 108
Pfu-Sulf     G-----EPTFKGDAILLY---YENPEEARMHVEEIYTY-DKKEFAVKVK 127
Sso-Sulf     SQN--EK--VKEGDTIGKT---YLGKEIAIMKKKIEKY-DKLKIAEKVK 122
Pae-Sulf     DKE--KIKGIKEGDSVLLK---LKGKEEAKNKEELWKLPDKKELADAVK 143
Afu-Sulf     SKEDYKALDVKEGDRLLLM---LKGQEFATEDKEEYKI-DPVDVATKTK 144
Pch-Sulf     SQEVIDEKKIQAASRITLRDFRDDRN-KALITKDRIYKP-DKTKEAKLVK 135
Ape-Sulf     NRDWVLNEGVSAGDDKIDT---YHGLEKAKKTEKEIYSW-DKGLHAKKVK 138
Sce-Sulf     DKAFAN--QKKPDTRKALK-FQDDEIEAKKITVKEYKP-NKTIEAKKVK 133
Tfu-Sulf     MH-------VDT HNFPEV-IEFRDKRKAEKGKRLIVASVQDLIDAGKVV 109

160       170       180       190       200
                  ....|....|....|....|....|....|....|....|....|....|
Bst-Sulf     KID-----------KLAHPGVRKLE-EKPKVYKGGAVIEKKRTDKG-QKA 162
Univ of OK   KID-----------KLAHPGVRKLE-EKPKVYKGGEITKKRTDKG-QKA 162
Aae-Sulf     GIT-----------DPRHPLKAEMH-TWGKYYKSGELKVKQLPKYY-DKP 145
Pfu-Sulf     KID-----------DPNILGKARVK-SMGKYLKGGGIEIKNELPN--PKA 163
Sso-Sulf     KI--K---------DIKHPCKKRTL-SYAKAFKACDKWIKEPQFNKPKS 160
Pae-Sulf     GIPERNKEVVKKRFDEKHPGWLIYR-SMRPMAKAGKKITVKNPPRFKEPKS 192
Afu-Sulf     GIPEKNPEVVREPFDDKHPGYVIYK-MHNPIIKAGKYTKNEPKFKEPKD 193
Pch-Sulf     GG-----------DPEHPAIVYLNNTVKEFYKGCKKEAKNKLNHY-DKV 172
Ape-Sulf     KIR-----------DPNHPGKEATK-KRGKILKGCRKEKKQGPPN--PLE 174
Sce-Sulf     RG-----------DPEHPAISYLKNVAGKYYKGGSKEAKQLPQHY-DKP 170
Tfu-Sulf     EP--------------KGR-KASRNRLQTAALKEAKKKYGFDAAKG 140

210       220       230       240       250
                  ....|....|....|....|....|....|....|....|....|....|
Bst-Sulf     PKYFDEAKTRKREA-KLGWNTVVGFQTRKPVHRAHEYKQKCAKEIVDK-- 209
Univ of OK   AKYFDPAKTRKKEA-KFGWNTVVGFQTRKPVHRAHEYKQKCAKEIVDK-- 209
Aae-Sulf     EKRKTPKKVREEIK-SLGLDKKVAFQTRKPMHRVHEEITKRAKEKVGKG- 193
Pfu-Sulf     KKTLRPVKTRILEK-KRGWKTKVAFQTRKVPHLGHEYKQKAAKTFVDK-- 210
Sso-Sulf     EKWLTPRMHRTVEK-KKCWKRVVAFQTRKVPHTGHEYLMKFAWFAANENQ 209
Pae-Sulf     RKWMPPRVSREYVK-KKGWRIVVAHQTRKVPHIGHEMKMKRAKFVAGG-- 239
Afu-Sulf     RKWFPPSKCREVIKNKKKKRTVKAHQTRKVPHVGHEMKMKCAAYTG-D-- 240
Pch-Sulf     ALRYTPAKLRVHED-KLGWSRVVAFQTRKPMHRAHRELTVRAARSRQAN- 220
Ape-Sulf     RKTLWPVKTRVLFK-KKGWRTVAAFQTRKVPHLGHEYKQKAAKTFVDK-- 221
Sce-Sulf     GLRKTEAKLRLEEK-SRQNDRVVAFQTRKPMHRAHRELTVRAAREANAK- 218
Tfu-Sulf     GARRDEEKARAKER---------VFSFRDEFGQWDPKNQKPEKWNLYN-- 179

260       270       280       290       300
                  ....|....|....|....|....|....|....|....|....|....|
Bst-Sulf     --------KFIKPKVGETKADDIPAKIRKESKQVLKKN-KYPKDRVFKGV 250
Univ of OK   --------KFIKPKVGETKSDDIPAKIRKESKQVLKKN-KYPKDRVFKGV 250
Aae-Sulf     --------KLKHPKVGLTKPGDVDVYTRKRIKVLKYEK-KYDKKKTILAF 234
Pfu-Sulf     --------KFIKPKVGRKKKGDYKDKVIKKAKY-LKMK-KCSN------- 243
Sso-Sulf     KVDEPRTGKLKKVKKGEKKVGDYIDKAILKLTKDALSKYGKISPKVHLKSF 259
Pae-Sulf     --ERPGDAKLKNAKKGAKKPGDYVDKAIKEGKKALNKAGKFHPDEHVKTM 287
Afu-Sulf     --IEPCHGKLKNAKKGAKKRGDYPDKAILEGKKEAKNKYGKIKPERHMKTF 288
Pch-Sulf     --------KLKHEKKGLTKPGDIDHFTRKRAKQALKPR-KPNG-MAVKGL 260
Ape-Sulf     --------KLKHEKAGWKKRGDYRDFVIKRAKKALKTH-KYPRGVVVLSV 262
Sce-Sulf     --------KLKHEKKGLTKPGDIDHKTRKRVKQEKKKR-KPNG-IAFLSL 258
Tfu-Sulf     ---------TR------VHRCKNIRVFPKSNKTELDVWHKIRRE------ 208

310       320       330       340       350
                  ....|....|....|....|....|....|....|....|....|....|
Bst-Sulf     FQAAMRYAGPREAKFHAKKRKNFGCTHFKKGRDHAGVC---N---KYGTK 294
Univ of OK   FQAAMRYAGPREAKFHAKKRKNFGCTHFKKGRDHAGVC---N---KYGTK 294
Aae-Sulf     LPLAMRMAGPREAKWHGIKRKNYGATHFKKGRDHASPGKDSKGKPKKDPK 284
Pfu-Sulf     -----------TTHHAIKRKTSTSKQT---------------------- 259
Sso-Sulf     TLWDMRYAGPREAKLHAIKRSNLGCTHKKFGRDHAGVC------NKKSPK 303
Pae-Sulf     TLWDMRYGNPLKKLHGIKRQNMGATHKMFGRDHAATC------DKKDPK 331
Afu-Sulf     TLWDMRYGNPIKKLHGVKRKNMGCTHKHFGRDHAAVC------EKKDMK 332
Pch-Sulf     LGLAMRMGCPREAKKWHAIKRKNHCATHKFKGRDHAGPCSNSKGEDKKGPK 310
Ape-Sulf     LRMNMNYAGPREAKHHAIKRKNFGATHKKGRDHAGVC------SKKGPK 306
Sce-Sulf     LPLAMRMSGDREAKWHAIKRKNYGAKHFKKGRDHAGPCKNSKGVDKKGPK 308
Tfu-Sulf     ---GKRLP----KKYFAHRRKVFERDGIKKP---DS--------PKKVTRD 240
```

TABLE 1-continued

ClustalW Analysis of ATP Sulfurylase Amino Acid Sequence

```
                360       370       380       390       400
           ....|....|....|....|....|....|....|....|....|....|
Bst-Sulf   AQ  SNFT------------AEE GITP FFEHSF CTKCEGMASTK- 331
Univ of OK AQ  LNFT------------AEE GITP FFEHSF CTKCEGMASTK- 331
Aae-Sulf   AQ  KKY-------------EDEIG KM PFEELV VPELDQYVEIN- 320
Pfu-Sulf   ------------------------------------------------- 259
Sso-Sulf    AH  DS----------INEED--L IKP FLRENY CPRCGSIENE-- 339
Pae-Sulf   AT Y  TRGLPSYGLNEPPHMTDKG R KP NLGEFA CPKCGEYTYLGM 381
Afu-Sulf   AT I  SQGIPSFGFEAPPNEVDYG K IPQNMAEFW CPICQEIAYS-- 380
Pch-Sulf    AQHAVEKY-------------KDE G EV EFQMVT LPDYDEYRPVD- 346
Ape-Sulf    AW  REF-------------PDL G TP FVREAY CRRCGGMVNEK- 341
Sce-Sulf   AQ  VESY------------KHE D EV PFRMVT LPDEDRYAPID- 344
Tfu-Sulf    D   EAS--------------------- RYRTVGDMTCTGAVLST-- 267

410       420       430       440       450
           ....|....|....|....|....|....|....|....|....|....|
Bst-Sulf   --------TCPHDAQYHVV SGTK RE-M RN QVP STFS RPEV AA  I 372
Univ of OK --------TCPHDAKYHVV SGTK RE-M RN QVP STFS RPEV AA  I 372
Aae-Sulf   --------EAKKRNLKYIN SGTE RENF KQ GRKL EWFT RPEV AE  A 362
Pfu-Sulf   ------------------------------------------------- 259
Sso-Sulf   --------ILCDHKDEKQEF SG L RS-I LDEVKPTKMVM RPEV YD  M 380
Pae-Sulf   SYEGYKEVALCGHT--PER SG L RG-I IE LRP KVVM RPEV YD  V 428
Afu-Sulf   --------ENCGHTDAKQKF SG G RG-M AE VFP RVVM RPEV YKQ V 421
Pch-Sulf   --------QVPAG-VKTLN SGTE RR-R RS AHI EWFSY PEV VK  R 386
Ape-Sulf   --------VCPHGDEYRVR SGTR RE-M GR ERP EYMM PEV ADA I 382
Sce-Sulf   --------QIDTTKTRTLN SGTE RR-R RV GEI EWFSY PEV VK  R 385
Tfu-Sulf   --------AT-TLDEVIAE A R TE---RGQTRADDRGSEAAMEERKR 305

460       470       480       490       500
           ....|....|....|....|....|....|....|....|....|....|
Bst-Sulf    GLQER-----------------ET T-----------------PSTR--- 386
Univ of OK  GLQER-----------------ET A-----------------PSAR--- 386
Aae-Sulf    TYVPKHKQGFCVWLTGLPCAGKST A-EILATMLQARGRKVTLLDGDVV 411
Pfu-Sulf   ------------------------------------------------- 259
Sso-Sulf    AAEQYGFGS--------PFVTEEY E--------------KRQSILG-- 406
Pae-Sulf    WWRVYGY----------PYVTDKY R--------------IKEQELEVE 454
Afu-Sulf    WWKVYNY----------PFVNRKY E--------------LKNKELEID 447
Pch-Sulf    SNPPRATQGFTIFLTGYMNSGKDA ARALQVTLNQQGGRSVSLLLGDTV 436
Ape-Sulf   SHPDPFI------------------------------------------ 389
Sce-Sulf    SNPPRPKQGFSIVLGNSLTVSREQ SIALLSTFLQFGGGRYYKIFEHNN 435
Tfu-Sulf    GYF--------------------------------------------- 309

510       520       530       540       550
           ....|....|....|....|....|....|....|....|....|....|
Bst-Sulf   ------------------------------------------------- 386
Univ of OK ------------------------------------------------- 386
Aae-Sulf   RTHLSRGLGFSKEDRITNILRVGFVASEIVKHNGVVICALVSPYRSARN- 460
Pfu-Sulf   ------------------------------------------------- 259
Sso-Sulf   ------------------------------------------------- 406
Pae-Sulf   L------------------------------------------------ 455
Afu-Sulf   LPAMEVPKA---------------------------------------- 456
Pch-Sulf   RHELSSELGFTREDRHTNIQRIAFVATELTRAGAAVIAAPIAPYEESRKF 486
Ape-Sulf   ------------------------------------------------- 389
Sce-Sulf   KTELLSLI------------------QDFIGSGSGLIIP--NQWEDD--- 462
Tfu-Sulf   ------------------------------------------------- 309

560       570       580       590       600
           ....|....|....|....|....|....|....|....|....|....|
Bst-Sulf   ------------------------------------------------- 386
Univ of OK ------------------------------------------------- 386
Aae-Sulf   QVRNMMEEGKFIEVFVDAPVEVCEERDVKGLYKKAKEGLIKGFTGVDDPY 510
Pfu-Sulf   ------------------------------------------------- 259
Sso-Sulf   ------------------------------------------------- 406
Pae-Sulf   ------------------------------------------------- 455
Afu-Sulf   ------------------------------------------------- 456
Pch-Sulf   ARDAVSQAGSFFLVHVATPLEHCEQSDKRGIYAAARRGIEKGFTGVDDPY 536
Ape-Sulf   ------------------------------------------------- 389
Sce-Sulf   -KDSVVGKQNVYLLDTSS------------------------------- 479
Tfu-Sulf   ------------------------------------------------- 309
```

TABLE 1-continued

ClustalW Analysis of ATP Sulfurylase Amino Acid Sequence

```
                   610       610       620
           ....|....|....|....|....|....|....|....|..
Bst-Sulf   --------------------------------------  386 (SEQ ID NO:2)
Univ of OK --------------------------------------  386 (SEQ ID NO:22)
Aae-Sulf   EPPVAPEVRVDTTKLTPEESALKILEFLKKEGFIKD-    546 (SEQ ID NO:23)
Pfu-Sulf   --------------------------------------  259 (SEQ ID NO:24)
Sso-Sulf   --------------------------------------  406 (SEQ ID NO:25)
Pae-Sulf   --------------------------------------  455 (SEQ ID NO:26)
Afu-Sulf   --------------------------------------  456 (SEQ ID NO:27)
Pch-Sulf   ETPEKADLVVDFSKQSVRSIVHEIILVLESQGFLERQ    573 (SEQ ID NO:28)
Ape-Sulf   --------------------------------------  389 (SEQ ID NO:29)
Sce-Sulf   ----SADIQLESADEPISHIVQKVVLFLEDNGFFVF-    511 (SEQ ID NO:30)
Tfu-Sulf   --------------------------------------  309 (SEQ ID NO:31)
```

A thermostable sulfurylase polypeptide is encoded by the open reading frame ("ORF") of a thermostable sulfurylase nucleic acid. An ORF corresponds to a nucleotide sequence that could potentially be translated into a polypeptide. A stretch of nucleic acids comprising an ORF is uninterrupted by a stop codon. An ORF that represents the coding sequence for a full protein begins with an ATG "start" codon and terminates with one of the three "stop" codons, namely, TAA, TAG, or TGA. For the purposes of this invention, an ORF may be any part of a coding sequence, with or without a start codon, a stop codon, or both. For an ORF to be considered as a good candidate for coding for a bonafide cellular protein, a minimum size requirement is often set, e.g., a stretch of DNA that would encode a protein of 50 amino acids or more.

The invention further encompasses nucleic acid molecules that differ from the nucleotide sequences shown in SEQ ID NO:1 due to degeneracy of the genetic code and thus encode the same thermostable sulfurylase proteins as that encoded by the nucleotide sequences shown in SEQ ID NO:1. In another embodiment, an isolated nucleic acid molecule of the invention has a nucleotide sequence encoding a protein having an amino acid sequence shown in SEQ ID NO:2. In addition to the thermostable sulfurylase nucleotide sequence shown in SEQ ID NO:1 it will be appreciated by those skilled in the art that DNA sequence polymorphisms that lead to changes in the amino acid sequences of the thermostable sulfurylase polypeptides may exist within a population (e.g., the bacterial population). Such genetic polymorphism in the thermostable sulfurylase genes may exist among individuals within a population due to natural allelic variation. As used herein, the terms "gene" and "recombinant gene" refer to nucleic acid molecules comprising an open reading frame encoding a thermostable sulfurylase protein. Such natural allelic variations can typically result in 1–5% variance in the nucleotide sequence of the thermostable sulfurylase genes. Any and all such nucleotide variations and resulting amino acid polymorphisms in the thermostable sulfurylase polypeptides, which are the result of natural allelic variation and that do not alter the functional activity of the thermostable sulfurylase polypeptides, are intended to be within the scope of the invention.

Moreover, nucleic acid molecules encoding thermostable sulfurylase proteins from other species, and thus that have a nucleotide sequence that differs from the sequence SEQ ID NO:1 are intended to be within the scope of the invention. Nucleic acid molecules corresponding to natural allelic variants and homologues of the thermostable sulfurylase cDNAs of the invention can be isolated based on their homology to the thermostable sulfurylase nucleic acids disclosed herein using the human cDNAs, or a portion thereof, as a hybridization probe according to standard hybridization techniques under stringent hybridization conditions. The invention further includes the nucleic acid sequence of SEQ ID NO: 1 and mature and variant forms thereof, wherein a first nucleotide sequence comprising a coding sequence differing by one or more nucleotide sequences from a coding sequence encoding said amino acid sequence, provided that no more than 11% of the nucleotides in the coding sequence differ from the coding sequence.

Another aspect of the invention pertains to nucleic acid molecules encoding a thermostable sulfurylase protein that contains changes in amino acid residues that are not essential for activity. Such thermostable sulfurylase proteins differ in amino acid sequence from SEQ ID NO:2 yet retain biological activity. In separate embodiments, the isolated nucleic acid molecule comprises a nucleotide sequence encoding a protein, wherein the protein comprises an amino acid sequence at least about 96%, 97%, 98% or 99% homologous to the amino acid sequence of SEQ ID NO:2. An isolated nucleic acid molecule encoding a thermostable sulfurylase protein homologous to the protein of SEQ ID NO:2 can be created by introducing one or more nucleotide substitutions, additions or deletions into the nucleotide sequence of SEQ ID NO:1 such that one or more amino acid substitutions, additions or deletions are introduced into the encoded protein.

Mutations can be introduced into SEQ ID NO:2 by standard techniques, such as site-directed mutagenesis and PCR-mediated mutagenesis. Preferably, conservative amino acid substitutions are made at one or more predicted, non-essential amino acid residues. A "conservative amino acid substitution" is one in which the amino acid residue is replaced with an amino acid residue having a similar side chain. Families of amino acid residues having similar side chains have been defined within the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in the thermostable sulfurylase protein is replaced with another amino acid residue from the same side chain family. Alternatively, in another embodiment, mutations can be introduced randomly along all or part of a thermostable sulfurylase coding sequence, such as by saturation mutagenesis, and the resultant mutants can be screened for thermostable sulfurylase biological activity to identify mutants that retain activity. Following mutagenesis of SEQ ID NO:1, the encoded protein can be expressed by any recombinant technology known in the art and the activity of the protein can be determined.

The relatedness of amino acid families may also be determined based on side chain interactions. Substituted amino acids may be fully conserved "strong" residues or fully conserved "weak" residues. The "strong" group of conserved amino acid residues may be any one of the following groups: STA, NEQK, NHQK, NDEQ, QHRK, MILV, MILF, HY, FYW, wherein the single letter amino acid codes are grouped by those amino acids that may be substituted for each other. Likewise, the "weak" group of conserved residues may be any one of the following: CSA, ATV, SAG, STNK, STPA, SGND, SNDEQK, NDEQHK, NEQHRK, VLIM, HFY, wherein the letters within each group represent the single letter amino acid code.

The thermostable sulfurylase nucleic acid of the invention includes the nucleic acid whose sequence is provided herein, or fragments thereof. The invention also includes mutant or variant nucleic acids any of whose bases may be changed from the corresponding base shown herein while still encoding a protein that maintains its sulfurylase-like activities and physiological functions, or a fragment of such a nucleic acid. The invention further includes nucleic acids whose sequences are complementary to those just described, including nucleic acid fragments that are complementary to any of the nucleic acids just described. The invention additionally includes nucleic acids or nucleic acid fragments, or complements thereto, whose structures include chemical modifications. Such modifications include, by way of nonlimiting example, modified bases, and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject.

A thermostable sulfurylase nucleic acid can encode a mature thermostable sulfurylase polypeptide. As used herein, a "mature" form of a polypeptide or protein disclosed in the present invention is the product of a naturally occurring polypeptide or precursor form or proprotein. The naturally occurring polypeptide, precursor or proprotein includes, by way of nonlimiting example, the full-length gene product, encoded by the corresponding gene. Alternatively, it may be defined as the polypeptide, precursor or proprotein encoded by an ORF described herein. The product "mature" form arises, again by way of nonlimiting example, as a result of one or more naturally occurring processing steps as they may take place within the cell, or host cell, in which the gene product arises. Examples of such processing steps leading to a "mature" form of a polypeptide or protein include the cleavage of the N-terminal methionine residue encoded by the initiation codon of an ORF, or the proteolytic cleavage of a signal peptide or leader sequence. Thus a mature form arising from a precursor polypeptide or protein that has residues 1 to N, where residue 1 is the N-terminal methionine, would have residues 2 through N remaining after removal of the N-terminal methionine. Alternatively, a mature form arising from a precursor polypeptide or protein having residues 1 to N, in which an N-terminal signal sequence from residue 1 to residue M is cleaved, would have the residues from residue M+1 to residue N remaining. Further as used herein, a "mature" form of a polypeptide or protein may arise from a step of post-translational modification other than a proteolytic cleavage event. Such additional processes include, by way of non-limiting example, glycosylation, myristoylation or phosphorylation. In general, a mature polypeptide or protein may result from the operation of only one of these processes, or a combination of any of them.

The term "isolated" nucleic acid molecule, as utilized herein, is one, which is separated from other nucleic acid molecules which are present in the natural source of the nucleic acid. Preferably, an "isolated" nucleic acid is free of sequences which naturally flank the nucleic acid (i.e., sequences located at the 5'- and 3'-termini of the nucleic acid) in the genomic DNA of the organism from which the nucleic acid is derived. For example, in various embodiments, the isolated thermostable sulfurylase nucleic acid molecules can contain less than about 5 kb, 4 kb, 3 kb, 2 kb, 1 kb, 0.5 kb or 0.1 kb of nucleotide sequences which naturally flank the nucleic acid molecule in genomic DNA of the cell/tissue from which the nucleic acid is derived (e.g., brain, heart, liver, spleen, etc.). Moreover, an "isolated" nucleic acid molecule, such as a cDNA molecule, can be substantially free of other cellular material or culture medium when produced by recombinant techniques, or of chemical precursors or other chemicals when chemically synthesized.

A nucleic acid molecule of the invention, e.g., a nucleic acid molecule having the nucleotide sequence of SEQ ID NO:1 or a complement of this aforementioned nucleotide sequence, can be isolated using standard molecular biology techniques and the sequence information provided herein. Using all or a portion of the nucleic acid sequence of SEQ ID NO:1 as a hybridization probe, thermostable sulfurylase molecules can be isolated using standard hybridization and cloning techniques (e.g., as described in Sambrook, et al., (eds.), *Molecular Cloning: A Laboratory Manual.* $2^{nd}$ Ed., Cold Spring Harbor Laboratory Press, Cold Spring Harbor, N.Y., 1989; and Ausubel, et al., (eds.), Current Protocols in *Molecular Biology*, John Wiley & Sons, New York, N.Y., 1993.)

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to thermostable sulfurylase nucleotide sequences can be prepared by standard synthetic techniques, e.g., using an automated DNA synthesizer.

As used herein, the term "complementary" refers to Watson-Crick or Hoogsteen base pairing between nucleotides units of a nucleic acid molecule, and the term "binding" means the physical or chemical interaction between two polypeptides or compounds or associated polypeptides or compounds or combinations thereof. Binding includes ionic, non-ionic, van der Waals, hydrophobic interactions, and the like. A physical interaction can be either direct or indirect. Indirect interactions may be through or due to the effects of another polypeptide or compound. Direct binding refers to interactions that do not take place through, or due to, the effect of another polypeptide or compound, but instead are without other substantial chemical intermediates.

Fragments provided herein are defined as sequences of at least 6 (contiguous) nucleic acids or at least 4 (contiguous) amino acids, a length sufficient to allow for specific hybridization in the case of nucleic acids or for specific recognition of an epitope in the case of amino acids, respectively, and are at most some portion less than a full length sequence.

Fragments may be derived from any contiguous portion of a nucleic acid or amino acid sequence of choice. Derivatives are nucleic acid sequences or amino acid sequences formed from the native compounds either directly or by modification or partial substitution. Analogs are nucleic acid sequences or amino acid sequences that have a structure similar to, but not identical to, the native compound but differs from it in respect to certain components or side chains. Analogs may be synthetic or from a different evolutionary origin and may have a similar or opposite metabolic activity compared to wild type. Homologs are nucleic acid sequences or amino acid sequences of a particular gene that are derived from different species.

Derivatives and analogs may be full length or other than full length, if the derivative or analog contains a modified nucleic acid or amino acid, as described below. Derivatives or analogs of the nucleic acids or proteins of the invention include, but are not limited to, molecules comprising regions that are substantially homologous to the nucleic acids or proteins of the invention, in various embodiments, by at least about 89% identity over a nucleic acid or amino acid sequence of identical size or when compared to an aligned sequence in which the alignment is done by a computer homology program known in the art, or whose encoding nucleic acid is capable of hybridizing to the complement of a sequence encoding the aforementioned proteins under stringent, moderately stringent, or low stringent conditions. See e.g. Ausubel, et al., CURRENT PROTOCOLS IN MOLECULAR BIOLOGY, John Wiley & Sons, New York, N.Y., 1993, and below.

A "homologous nucleic acid sequence" or "homologous amino acid sequence," or variations thereof, refer to sequences characterized by a homology at the nucleotide level or amino acid level as discussed above. Homologous nucleotide sequences encode those sequences coding for isoforms of thermostable sulfurylase polypeptides. Isoforms can be expressed in different tissues of the same organism as a result of, for example, alternative splicing of RNA. Alternatively, isoforms can be encoded by different genes. In the invention, homologous nucleotide sequences include nucleotide sequences encoding for a thermostable sulfurylase polypeptide of species other than humans, including, but not limited to: vertebrates, and thus can include, e.g., frog, mouse, rat, rabbit, dog, cat cow, horse, and other organisms. Homologous nucleotide sequences also include, but are not limited to, naturally occurring allelic variations and mutations of the nucleotide sequences set forth herein. Homologous nucleic acid sequences include those nucleic acid sequences that encode conservative amino acid substitutions in SEQ ID NO:1, as well as a polypeptide possessing thermostable sulfurylase biological activity. Various biological activities of the thermostable sulfurylase proteins are described below.

The thermostable sulfurylase proteins of the invention include the sulfurylase protein whose sequence is provided herein. The invention also includes mutant or variant proteins any of whose residues may be changed from the corresponding residue shown herein while still encoding a protein that maintains its sulfurylase-like activities and physiological functions, or a functional fragment thereof. The invention further encompasses antibodies and antibody fragments, such as $F_{ab}$ or $(F_{ab})_2$, that bind immunospecifically to any of the proteins of the invention. This invention also includes a variant or a mature form of the amino acid sequence of SEQ ID NO:2, wherein one or more amino acid residues in the variant differs in no more than 4% of the amino acic residues from the amino acid sequence of the mature form.

Several assays have been developed for detection of the forward ATP sulfurylase reaction. The colorimetric molybdolysis assay is based on phosphate detection (see e.g., Wilson and Bandurski, 1958. *J. Biol. Chem.* 233: 975–981), whereas the continuous spectrophotometric molybdolysis assay is based upon the detection of NADH oxidation (see e.g., Seubert, et al, 1983. *Arch. Biochem. Biophys.* 225: 679–691; Seubert, et al, 1985. *Arch. Biochem. Biophys.* 240: 509–523). The later assay requires the presence of several detection enzymes.

Suitable enzymes for converting ATP into light include luciferases, e.g., insect luciferases. Luciferases produce light as an end-product of catalysis. The best known light-emitting enzyme is that of the firefly, *Photinus pyralis* (*Coleoptera*). The corresponding gene has been cloned and expressed in bacteria (see e.g., de Wet, et al., 1985. *Proc. Nat. Acad. Sci. USA* 80: 7870–7873) and plants (see e.g., Ow, et al., 1986. *Science* 234: 856–859), as well as in insect (see e.g., Jha, et al., 1990. *FEBS Lett.* 274: 24–26) and mammalian cells (see e.g., de Wet, et al, 1987. *Mol. Cell. Biol.* 7: 725–7373; Keller, et al., 1987. *Proc. Natl. Acad. Sci. USA* 82: 3264–3268). In addition, a number of luciferase genes from the Jamaican click beetle, *Pyroplorus plagiophihalamus* (*Coleoptera*), have recently been cloned and partially characterized (see e.g., Wood, et al., 1989. *J. Biolumin. Chemilumin.* 4: 289–301; Wood, et al., 1989. *Science* 244: 700–702). Distinct luciferases can sometimes produce light of different wavelengths, which may enable simultaneous monitoring of light emissions at different wavelengths. Accordingly, these aforementioned characteristics are unique, and add new dimensions with respect to the utilization of current reporter systems.

Firefly luciferase catalyzes bioluminescence in the presence of luciferin, adenosine 5'-triphosphate (ATP), magnesium ions, and oxygen, resulting in a quantum yield of 0.88 (see e.g., McElroy and Selinger, 1960. *Arch. Biochem. Biophys.* 88: 136–145). The firefly luciferase bioluminescent reaction can be utilized as an assay for the detection of ATP with a detection limit of approximately $1\times10^{-13}$ M (see e.g., Leach, 1981. *J. Appl. Biochem.* 3: 473–517). In addition, the overall degree of sensitivity and convenience of the luciferase-mediated detection systems have created considerable interest in the development of firefly luciferase-based biosensors (see e.g., Green and Kricka, 1984. *Talanta* 31: 173–176; Blum, et al., 1989. *J. Biolumin. Chemilumin.* 4: 543–550).

The development of new reagents have made it possible to obtain stable light emission proportional to the concentrations of ATP (see e.g., Lundin, 1982. Applications of firefly luciferase In; *Luminescent Assays* (Raven Press, New York). With such stable light emission reagents, it is possible to make endpoint assays and to calibrate each individual assay by addition of a known amount of ATP. In addition, a stable light-emitting system also allows continuous monitoring of ATP-converting systems.

In a preferred embodiment, the ATP generating-ATP converting fusion protein is attached to an affinity tag. The term "affinity tag" is used herein to denote a peptide segment that can be attached to a polypeptide to provide for purification or detection of the polypeptide or provide sites for attachment of the polypeptide to a substrate. In principal, any peptide or protein for which an antibody or other specific binding agent is available can be used as an affinity tag. Affinity tags include a poly-histidine tract or a biotin carboxyl carrier protein (BCCP) domain, protein A (Nilsson et al., EMBO J. 4:1075, 1985; Nilsson et al., Methods Enzymol. 198:3, 1991), glutathione S transferase (Smith and Johnson, Gene 67:31, 1988), substance P, Flag.™.peptide (Hopp et al., Biotechnology 6:1204–1210, 1988; available from Eastman Kodak Co., New Haven, Conn.), streptavidin binding peptide, or other antigenic epitope or binding domain. See, in general Ford et al., Protein Expression and Purification 2: 95–107, 1991. DNAs encoding affinity tags are available from commercial suppliers (e.g., Pharmacia Biotech, Piscataway, N.J.).

As used herein, the term "poly-histidine tag," when used in reference to a fusion protein refers to the presence of two to ten histidine residues at either the amino- or carboxy-terminus of a protein of interest. A poly-histidine tract of six to ten residues is preferred. The poly-histidine tract is also defined functionally as being a number of consecutive histidine residues added to the protein of interest which allows the affinity purification of the resulting fusion protein on a nickel-chelate or IDA column.

In some embodiments, the fusion protein has an orientation such that the sulfurylase polypeptide is N-terminal to the luciferase polypeptide. In other embodiments, the luciferase polypeptide is N-terminal to the sulfurylase polypeptide. As used herein, the term sulfurylase-luciferase fusion protein refers to either of these orientations. The terms "amino-terminal" (N-terminal) and "carboxyl-terminal" (C-terminal) are used herein to denote positions within polypeptides and proteins. Where the context allows, these terms are used with reference to a particular sequence or portion of a polypeptide or protein to denote proximity or relative position. For example, a certain sequence positioned carboxyl-terminal to a reference sequence within a protein is located proximal to the carboxyl terminus of the reference sequence, but is not necessarily at the carboxyl terminus of the complete protein.

The fusion protein of this invention can be produced by standard recombinant DNA techniques. For example, DNA fragments coding for the different polypeptide sequences are ligated together in-frame in accordance with conventional techniques, e.g., by employing blunt-ended or "sticky"-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, for example, Ausubel et al. (eds.) CURRENT PROTOCOLS IN MOLECULAR BIOLOGY, John Wiley & Sons, 1992). The two polypeptides of the fusion protein can also be joined by a linker, such as a unique restriction site, which is engineered with specific primers during the cloning procedure. In one embodiment, the sulfurylase and luciferase polypeptides are joined by a linker, for example an ala-ala-ala linker which is encoded by a NotI restriction site.

In one embodiment, the invention includes a recombinant polynucleotide that comprises a coding sequence for a fusion protein having an ATP generating polypeptide sequence and an ATP converting polypeptide sequence. In a preferred embodiment, the recombinant polynucleotide encodes a sulfurylase-luciferase fusion protein. The term "recombinant DNA molecule" or "recombinant polynucleotide" as used herein refers to a DNA molecule which is comprised of segments of DNA joined together by means of molecular biological techniques. The term "recombinant protein" or "recombinant polypeptide" as used herein refers to a protein molecule which is expressed from a recombinant DNA molecule.

In one aspect, this invention discloses a sulfurylase-luciferase fusion protein with an N-terminal hexahistidine tag and a BCCP tag. The nucleic acid sequence of the disclosed N-terminal hexahistidine-BCCP luciferase-sulfurylase gene (His6-BCCP L-S) gene is shown below:

| His6-BCCP L–S Nucleotide Sequence: | | |
|---|---|---|
| ATGCGGGGTTCTCATCATCATCATCATCATGGTATGGCTAGCATGGAAGCGCCAGCAGCA | 60 | (SEQ ID NO:3) |
| GCGGAAATCAGTGGTCACATCGTACGTTCCCCGATGGTTGGTACTTTCTACCGCACCCCA | 120 | |
| AGCCCGGACGCAAAAGCGTTCATCGAAGTGGGTCAGAAAGTCAACGTGGGCGATACCCTG | 180 | |
| TGCATCGTTGAAGCCATGAAAATGATGAACCAGATCGAAGCGGACAAATCCGGTACCGTG | 240 | |
| AAAGCAATTCTGGTCGAAAGTGGACAACCGGTAGAATTTGACGAGCCGCTGGTCGTCATC | 300 | |
| GAGGGATCCGAGCTCGAGATCCAAATGGAAGACGCCAAAAACATAAAGAAAGGCCCGGCG | 360 | |
| CCATTCTATCCTCTAGAGGATGGAACCGCTGGAGAGCAACTGCATAAGGCTATGAAGAGA | 420 | |
| TACGCCCTGGTTCCTGGAACAATTGCTTTTACAGATGCACATATCGAGGTGAACATCACG | 480 | |
| TACGCGGAATACTTCGAAATGTCCGTTCGGTTGGCAGAAGCTATGAAACGATATGGGCTG | 540 | |
| AATACAAATCACAGAATCGTCGTATGCAGTGAAAACTCTCTTCAATTCTTTATGCCGGTG | 600 | |
| TTGGGCGCGTTATTTATCGGAGTTGCAGTTGCGCCCGCGAACGACATTTATAATGAACGT | 660 | |
| GAATTGCTCAACAGTATGAACATTTCGCAGCCTACCGTAGTGTTTGTTTCCAAAAAGGGG | 720 | |
| TTGCAAAAAATTTTGAACGTGCAAAAAAAATTACCAATAATCCAGAAAATTATTATCATG | 780 | |
| GATTCTAAAACGGATTACCAGGGATTTCAGTCGATGTACACGTTCGTCACATCTCATCTA | 840 | |
| CCTCCCGGTTTTAATGAATACGATTTTGTACCAGAGTCCTTTGATCGTGACAAAACAATT | 900 | |

His6-BCCP L-S Nucleotide Sequence:

```
GCACTGATAATGAATTCCTCTGGATCTACTGGGTTACCTAAGGGTGTGGCCCTTCCGCAT    960
AGAACTGCCTGCGTCAGATTCTCGCATGCCAGAGATCCTATTTTTGGCAATCAAATCATT   1020
CCGGATACTGCGATTTTAAGTGTTGTTCCATTCCATCACGGTTTTGGAATGTTTACTACA   1080
CTCGGATATTTGATATGTGGATTTCGAGTCGTCTTAATGTATAGATTTGAAGAAGAGCTG   1140
TTTTTACGATCCCTTCAGGATTACAAAATTCAAAGTGCGTTGCTAGTACCAACCCTATTT   1200
TCATTCTTCGCCAAAAGCACTCTGATTGACAAATACGATTTATCTAATTTACACGAAATT   1260
GCTTCTGGGGCGCACCTCTTTCGAAAGAAGTCGGGGAAGCGGTTGCAAAACGCTTCCAT    1320
CTTCCAGGGATACGACAAGGATATGGGCTCACTGAGACTACATCAGCTATTCTGATTACA   1380
CCCGAGGGGATGATAAACCGGGCGCGGTCGGTAAAGTTGTTCCATTTTTTGAAGCGAAG    1440
GTTGTGGATCTGGATACCGGGAAAACGCTGGGCGTTAATCAGAGAGGCGAATTATGTGTC   1500
AGAGGACCTATGATTATGTCCGGTTATGTAAACAATCCGGAAGCGACCAACGCCTTGATT   1560
GACAAGGATGGCTACATTCTGGAGACATAGCTTACTGGGACGAAGACGAACACTTC       1620
TTCATAGTTGACCGCTTGAAGTCTTTAATTAAATACAAAGGATATCAGGTGGCCCCCGCT   1680
GAATTGGAATCGATATTGTTACAACACCCCAACATCTTCGACGCGGGCGTGGCAGGTCTT   1740
CCCGACGATGACGCCGGTGAACTTCCCGCCGCCGTTGTTGTTTGGAGCACGGAAAGACG    1800
ATGACGGAAAAAGAGATCGTGGATTACGTCGCCAGTCAAGTAACAACCGCGAAAAAGTTG   1860
CGCGGAGGAGTTGTGTTTGTGGACGAAGTACCGAAAGGTCTTACCGGAAAACTCGACGCA   1920
AGAAAAATCAGAGAGATCCTCATAAAGGCCAAGAAGGGCGGAAAGTCCAAATTGGCGGCC   1980
GCTATGCCTGCTCCTCACGGTGGTATTCTACAAGACTTGATTGCTAGAGATGCGTTAAAG   2040
AAGAATGAATTGTTATCTGAAGCGCAATCTTCGGACATTTTAGTATGGAACTTGACTCCT   2100
AGACAACTATGTGATATTGAATTGATTCTAAATGGTGGGTTTTCTCCTCTGACTGGGTTT   2160
TTGAACGAAAACGATTACTCCTCTGTTGTTACAGATTCGAGATTAGCAGACGGCACATTG   2220
TGGACCATCCCTATTACATTAGATGTTGATGAAGCATTTGCTAACCAAATTAAACCAGAC   2280
ACAAGAATTGCCCTTTTCCAAGATGATGAAATTCCTATTGCTATACTTACTGTCCAGGAT   2340
GTTTACAAGCCAAACAAAACTATCGAAGCCGAAAAAGTCTTCAGAGGTGACCCAGAACAT   2400
CCAGCCATTAGCTATTTATTTAACGTTGCCGGTGATTATTACGTCGGCGGTTCTTTAGAA   2460
GCGATTCAATTACCTCAACATTATGACTATCCAGGTTTGCGTAAGACACCTGCCCAACTA   2520
AGACTTGAATTCCAATCAAGACAATGGGACCGTGTCGTAGCTTTCCAAACTCGTAATCCA   2580
ATGCATAGAGCCCACAGGGAGTTGACTGTGAGAGCCGCCAGAGAAGCTAATGCTAAGGTG   2640
CTGATCCATCCAGTTGTTGGACTAACCAAACCAGGTGATATAGACCATCACACTCGTGTT   2700
CGTGTCTACCAGGAAATTATTAAGCGTTATCCTAATGGTATTGCTTTCTTATCCCTGTTG   2760
CCATTAGCAATGAGAATGAGTGGTGATAGAGAAGCCGTATGGCATGCTATTATTAGAAAG   2820
AATTATGGTGCCTCCCACTTCATTGTTGGTAGAGACCATGCGGGCCCAGGTAAGAACTCC   2880
AAGGGTGTTGATTTCTACGGTCCATACGATGCTCAAGAATTGGTCGAATCCTACAAGCAT   2940
GAACTGGACATTGAAGTTGTTCCATTCAGAATGGTCACTTATTTGCCAGACGAAGACCGT   3000
TATGCTCCAATTGATCAAATTGACACCACAAAGACGAGAACCTTGAACATTTCAGGTACA   3060
GAGTTGAGACGCCGTTTAAGAGTTGGTGGTGAGATTCCTGAATGGTTCTCATATCCTGAA   3120
GTGGTTAAAATCCTAAGAGAATCCAACCCCACCAAGACCAAAACAAGGTTTTTCAATTGTT   3180
```

| His6-BCCP L-S Nucleotide Sequence: |  |
|---|---|
| TTAGGTAATTCATTAACCGTTTCTCGTGAGCAATTATCCATTGCTTTGTTGTCAACATTC | 3240 |
| TTGCAATTCGGTGGTGGCAGGTATTACAAGATCTTTGAACACAATAATAAGACAGAGTTA | 3300 |
| CTATCTTTGATTCAAGATTTCATTGGTTCTGGTAGTGGACTAATTATTCCAAATCAATGG | 3360 |
| GAAGATGACAAGGACTCTGTTGTTGGCAAGCAAAACGTTTACTTATTAGATACCTCAAGC | 3420 |
| TCAGCCGATATTCAGCTAGAGTCAGCGGATGAACCTATTTCACATATTGTACAAAAAGTT | 3480 |
| GTCCTATTCTTGGAAGACAATGGCTTTTTTGTATTTTAA | 3519 |

The amino acid sequence of the disclosed His6-BCCP L-S polypeptide is presented using the three letter amino acid code (SEQ ID NO:4).

```
His6-BCCP L-S Amino Acid Sequence

Met Arg Gly Ser His His His His His Gly Met Ala Ser Met Glu    (SEQ ID NO:4)
1               5                   10                  15

Ala Pro Ala Ala Ala Glu Ile Ser Gly His Ile Val Arg Ser Pro Met
            20                  25                  30

Val Gly Thr Phe Tyr Arg Thr Pro Ser Pro Asp Ala Lys Ala Phe Ile
            35                  40                  45

Glu Val Gly Gln Lys Val Asn Val Gly Asp Thr Leu Cys Ile Val Glu
            50                  55                  60

Ala Met Lys Met Met Asn Gln Ile Glu Ala Asp Lys Ser Gly Thr Val
65                  70                  75                  80

Lys Ala Ile Leu Val Glu Ser Gly Gln Pro Val Glu Phe Asp Glu Pro
            85                  90                  95

Leu Val Val Ile Glu Gly Ser Glu Leu Glu Ile Gln Met Glu Asp Ala
            100                 105                 110

Lys Asn Ile Lys Lys Gly Pro Ala Pro Phe Tyr Pro Leu Glu Asp Gly
            115                 120                 125

Thr Ala Gly Glu Gln Leu His Lys Ala Met Lys Arg Tyr Ala Leu Val
130                 135                 140

Pro Gly Thr Ile Ala Phe Thr Asp Ala His Ile Glu Val Asn Ile Thr
145                 150                 155                 160

Tyr Ala Glu Tyr Phe Glu Met Ser Val Arg Leu Ala Glu Ala Met Lys
            165                 170                 175

Arg Tyr Gly Leu Asn Thr Asn His Arg Ile Val Val Cys Ser Glu Asn
            180                 185                 190

Ser Leu Gln Phe Phe Met Pro Val Leu Gly Ala Leu Phe Ile Gly Val
            195                 200                 205

Ala Val Ala Pro Ala Asn Asp Ile Tyr Asn Glu Arg Glu Leu Leu Asn
            210                 215                 220

Ser Met Asn Ile Ser Gln Pro Thr Val Val Phe Val Ser Lys Lys Gly
225                 230                 235                 240

Leu Gln Lys Ile Leu Asn Val Gln Lys Lys Leu Pro Ile Ile Gln Lys
            245                 250                 255

Ile Ile Ile Met Asp Ser Lys Thr Asp Tyr Gln Gly Phe Gln Ser Met
            260                 265                 270
```

His6-BCCP L-S Amino Acid Sequence

Tyr Thr Phe Val Thr Ser His Leu Pro Pro Gly Phe Asn Glu Tyr Asp
        275                 280                 285

Phe Val Pro Glu Ser Phe Asp Arg Asp Lys Thr Ile Ala Leu Ile Met
    290                 295                 300

Asn Ser Ser Gly Ser Thr Gly Leu Pro Lys Gly Val Ala Leu Pro His
305                 310                 315                 320

Arg Thr Ala Cys Val Arg Phe Ser His Ala Arg Asp Pro Ile Phe Gly
            325                 330                 335

Asn Gln Ile Ile Pro Asp Thr Ala Ile Leu Ser Val Val Pro Phe His
            340                 345                 350

His Gly Phe Gly Met Phe Thr Thr Leu Gly Tyr Leu Ile Cys Gly Phe
        355                 360                 365

Arg Val Val Leu Met Tyr Arg Phe Glu Glu Gln Leu Phe Leu Arg Ser
    370                 375                 380

Leu Gln Asp Tyr Lys Ile Gln Ser Ala Leu Leu Val Pro Thr Leu Phe
385                 390                 395                 400

Ser Phe Phe Ala Lys Ser Thr Leu Ile Asp Lys Tyr Asp Leu Ser Asn
            405                 410                 415

Leu His Glu Ile Ala Ser Gly Gly Ala Pro Leu Ser Lys Glu Val Gly
            420                 425                 430

Glu Ala Val Ala Lys Arg Phe His Leu Pro Gly Ile Arg Gln Gly Tyr
            435                 440                 445

Gly Leu Thr Glu Thr Thr Ser Ala Ile Leu Ile Thr Pro Glu Gly Asp
        450                 455                 460

Asp Lys Pro Gly Ala Val Gly Lys Val Val Pro Phe Phe Glu Ala Lys
465                 470                 475                 480

Val Val Asp Leu Asp Thr Gly Lys Thr Leu Gly Val Asn Gln Arg Gly
            485                 490                 495

Glu Leu Cys Val Arg Gly Pro Met Ile Met Ser Gly Tyr Val Asn Asn
            500                 505                 510

Pro Glu Ala Thr Asn Ala Leu Ile Asp Lys Asp Gly Trp Leu His Ser
        515                 520                 525

Gly Asp Ile Ala Tyr Trp Asp Glu Asp Glu His Phe Phe Ile Val Asp
    530                 535                 540

Arg Leu Lys Ser Leu Ile Lys Tyr Lys Gly Tyr Gln Val Ala Pro Ala
545                 550                 555                 560

Glu Leu Glu Ser Ile Leu Leu Gln His Pro Asn Ile Phe Asp Ala Gly
            565                 570                 575

Val Ala Gly Leu Pro Asp Asp Ala Gly Glu Leu Pro Ala Ala Val
            580                 585                 590

Val Val Leu Glu His Gly Lys Thr Met Thr Glu Lys Glu Ile Val Asp
        595                 600                 605

Tyr Val Ala Ser Gln Val Thr Thr Ala Lys Lys Leu Arg Gly Gly Val
    610                 615                 620

Val Phe Val Asp Glu Val Pro Lys Gly Leu Thr Gly Lys Leu Asp Ala
625                 630                 635                 640

Arg Lys Ile Arg Glu Ile Leu Ile Lys Ala Lys Gly Gly Lys Ser
            645                 650                 655

Lys Leu Ala Ala Ala Met Pro Ala Pro His Gly Gly Ile Leu Gln Asp
            660                 665                 670

-continued

His6-BCCP L-S Amino Acid Sequence

Leu Ile Ala Arg Asp Ala Leu Lys Lys Asn Glu Leu Leu Ser Glu Ala
            675                 680                 685

Gln Ser Ser Asp Ile Leu Val Trp Asn Leu Thr Pro Arg Gln Leu Cys
            690                 695                 700

Asp Ile Glu Leu Ile Leu Asn Gly Gly Phe Ser Pro Leu Thr Gly Phe
705                 710                 715

Leu Asn Glu Asn Asp Tyr Ser Ser Val Val Thr Asp Ser Arg Leu Ala
720                 725                 730                 735

Asp Gly Thr Leu Trp Thr Ile Pro Ile Thr Leu Asp Val Asp Glu Ala
            740                 745                 750

Phe Ala Asn Gln Ile Lys Pro Asp Thr Arg Ile Ala Leu Phe Gln Asp
            755                 760                 765

Asp Glu Ile Pro Ile Ala Ile Leu Thr Val Gln Asp Val Tyr Lys Pro
            770                 775                 780

Asn Lys Thr Ile Glu Ala Glu Lys Val Phe Arg Gly Asp Pro Glu His
            785                 790                 795

Pro Ala Ile Ser Tyr Leu Phe Asn Val Ala Gly Asp Tyr Tyr Val Gly
800                 805                 810                 815

Gly Ser Leu Glu Ala Ile Gln Leu Pro Gln His Tyr Asp Tyr Pro Gly
            820                 825                 830

Leu Arg Lys Thr Pro Ala Gln Leu Arg Leu Glu Phe Gln Ser Arg Gln
            835                 840                 845

Trp Asp Arg Val Val Ala Phe Gln Thr Arg Asn Pro Met His Arg Ala
            850                 855                 860

His Arg Glu Leu Thr Val Arg Ala Ala Arg Glu Ala Asn Ala Lys Val
            865                 870                 875

Leu Ile His Pro Val Val Gly Leu Thr Lys Pro Gly Asp Ile Asp His
880                 885                 890                 895

His Thr Arg Val Arg Val Tyr Gln Glu Ile Ile Lys Arg Tyr Pro Asn
            900                 905                 910

Gly Ile Ala Phe Leu Ser Leu Leu Pro Leu Ala Met Arg Met Ser Gly
            915                 920                 925

Asp Arg Glu Ala Val Trp His Ala Ile Ile Arg Lys Asn Tyr Gly Ala
            930                 935                 940

Ser His Phe Ile Val Gly Arg Asp His Ala Gly Pro Gly Lys Asn Ser
            945                 950                 955

Lys Gly Val Asp Phe Tyr Gly Pro Tyr Asp Ala Gln Glu Leu Val Glu
960                 965                 970                 975

Ser Tyr Lys His Glu Leu Asp Ile Glu Val Val Pro Phe Arg Met Val
            980                 985                 990

Thr Tyr Leu Pro Asp Glu Asp Arg Tyr Ala Pro Ile Asp Gln Ile Asp
            995                 1000                1005

Thr Thr Lys Thr Arg Thr Leu Asn Ile Ser Gly Thr Glu Leu Arg Arg
            1010                1015                1020

Arg Leu Arg Val Gly Gly Glu Ile Pro Glu Trp Phe Ser Tyr Pro Glu
            1025                1030                1035

Val Val Lys Ile Leu Arg Glu Ser Asn Pro Pro Arg Pro Lys Gln Gly
1040                1045                1050                1055

Phe Ser Ile Val Leu Gly Asn Ser Leu Thr Val Ser Arg Glu Gln Leu
                1060                1065                1070

-continued

His6-BCCP L-S Amino Acid Sequence

```
Ser Ile Ala Leu Leu Ser Thr Phe Leu Gln Phe Gly Gly Gly Arg Tyr
        1075                1080                1085
Tyr Lys Ile Phe Glu His Asn Asn Lys Thr Glu Leu Leu Ser Leu Ile
    1090                1095                1100
Gln Asp Phe Ile Gly Ser Gly Ser Gly Leu Ile Ile Pro Asn Gln Trp
1105                1110                1115
Glu Asp Lys Asp Ser Val Val Gly Lys Gln Asn Val Tyr Leu Leu
1120            1125            1130                    1135
Asp Thr Ser Ser Ser Ala Asp Ile Gln Leu Glu Ser Ala Asp Glu Pro
            1140                1145                1150
Ile Ser His Ile Val Gln Lys Val Val Leu Phe Leu Glu Asp Asn Gly
        1155                1160                1165
Phe Phe Val Phe
    1170
```

Accordingly, in one aspect, the invention provides for a fusion protein comprising a thermostable sulfurylase joined to at least one affinity tag. The nucleic acid sequence of the disclosed N-terminal hexahistidine-BCCP Bst ATP Sulfurylase (His6-BCCP Bst Sulfurylase) gene is shown below:

His6-BCCP Bst Sulfurylase Nucleotide Sequence

| Sequence | Position | |
|---|---|---|
| ATGCGGGGTTCTCATCATCATCATCATCATGGTATGGCTAGCATGGAAGCGCCAGCAGCA | 60 | (SEQ ID NO:5) |
| GCGGAAATCAGTGGTCACATCGTACGTTCCCCGATGGTTGGTACTTTCTACCGCACCCCA | 120 | |
| AGCCCGGACGCAAAAGCGTTCATCGAAGTGGGTCAGAAAGTCAACGTGGGCGATACCCTG | 180 | |
| TGCATCGTTGAAGCCATGAAAATGATGAACCAGATCGAAGCGGACAAATCCGGTACCGTG | 240 | |
| AAAGCAATTCTGGTCGAAAGTGGACAACCGGTAGAATTTGACGAGCCGCTGGTCGTCATC | 300 | |
| GAGGGATCCGAGCTCGAGATCTGCAGCATGAGCGTAAGCATCCCGCATGGCGGCACATTG | 360 | |
| ATCAACCGTTGGAATCCGGATTACCCAATCGATGAAGCAACGAAAACGATCGAGCTGTCC | 420 | |
| AAAGCCGAACTAAGCGACCTTGAGCTGATCGGCACAGGCGCCTACAGCCCGCTCACCGGG | 480 | |
| TTTTTAACGAAAGCCGATTACGATGCGGTCGTAGAAACGATGCGCCTCGCTGATGGCACT | 540 | |
| GTCTGGAGCATTCCGATCACGCTGGCGGTGACGGAAGAAAAAGCGAGTGAACTCACTGTC | 600 | |
| GGCGACAAAGCGAAACTCGTTTATGGCGGCGACGTCTACGGCGTCATTGAAATCGCCGAT | 660 | |
| ATTTACCGCCCGGATAAAACGAAAGAAGCCAAGCTCGTCTATAAAACCGATGAACTCGCT | 720 | |
| CACCCGGGCGTGCGCAAGCTGTTTGAAAAACCAGATGTGTACGTCGGCGGAGCGGTTACG | 780 | |
| CTCGTCAAACGGACCGACAAAGGCCAGTTTGCTCCGTTTTATTTCGATCCGGCCGAAACG | 840 | |
| CGGAAACGATTTGCCGAACTCGGCTGGAATACCGTCGTCGGCTTCCAAACACGCAACCCG | 900 | |
| GTTCACCGCGCCCATGAATACATTCAAAAATGCGCGCTTGAAATCGTGGACGGCTTGTTT | 960 | |
| TTAAACCCGCTCGTCGGCGAAACGAAAGCGGACGATATTCCGGCCGACATCCGGATGGAA | 1020 | |
| AGCTATCAAGTGCTGCTGGAAAACTATTATCCGAAAGACCGCGTTTTCTTGGGCGTCTTC | 1080 | |
| CAAGCTGCGATGCGCTATGCCGGTCCGCGCGAAGCGATTTTCCATGCCATGGTGCGGAAA | 1140 | |
| AACTTCGGCTGCACGCACTTCATCGTCGGCCGCGACCATGCGGGCGTCGGCAACTATTAC | 1200 | |
| GGCACGTATGATGCGCAAAAAATCTTCTCGAACTTTACAGCCGAAGAGCTTGGCATTACA | 1260 | |
| CCGCTCTTTTTCGAACACAGCTTTTATTGCACGAAATGCGAAGGCATGGCATCGACGAAA | 1320 | |

-continued

His6-BCCP Bst Sulfurylase Nucleotide Sequence

```
ACATGCCCGCACGACGCACAATATCACGTTGTCCTTTCTGGCACGAAAGTCCGTGAAATG   1380
TTGCGTAACGGCCAAGTGCCGCCGAGCACATTCAGCCGTCCGGAAGTGGCCGCCGTTTTG   1440
ATCAAAGGGCTGCAAGAACGCGAAACGGTCGCCCCGTCAGCGCGCTAA              1488
```

The amino acid sequence of the His6-BCCP Bst Sulfurylase polypeptide is presented using the three letter amino acid code in Table 6 (SEQ ID NO:6).

His6-BCCP Bst Sulfurylase Amino Acid Sequence

```
Met Arg Gly Ser His His His His His Gly Met Ala Ser Met Glu    (SEQ ID NO:6)
1               5                   10                  15

Ala Pro Ala Ala Ala Glu Ile Ser Gly His Ile Val Arg Ser Pro Met
                20                  25                  30

Val Gly Thr Phe Tyr Arg Thr Pro Ser Pro Asp Ala Lys Ala Phe Ile
            35                  40                  45

Glu Val Gly Gln Lys Val Asn Val Gly Asp Thr Leu Cys Ile Val Glu
    50                  55                  60

Ala Met Lys Met Met Asn Gln Ile Glu Ala Asp Lys Ser Gly Thr Val
65                  70                  75                  80

Lys Ala Ile Leu Val Glu Ser Gly Gln Pro Val Glu Phe Asp Glu Pro
                85                  90                  95

Leu Val Val Ile Glu Gly Ser Glu Leu Glu Ile Cys Ser Met Ser Val
            100                 105                 110

Ser Ile Pro His Gly Gly Thr Leu Ile Asn Arg Trp Asn Pro Asp Tyr
        115                 120                 125

Pro Ile Asp Glu Ala Thr Lys Thr Ile Glu Leu Ser Lys Ala Glu Leu
    130                 135                 140

Ser Asp Leu Glu Leu Ile Gly Thr Gly Ala Tyr Ser Pro Leu Thr Gly
145                 150                 155                 160

Phe Leu Thr Lys Ala Asp Tyr Asp Ala Val Val Glu Thr Met Arg Leu
                165                 170                 175

Ala Asp Gly Thr Val Trp Ser Ile Pro Ile Thr Leu Ala Val Thr Glu
            180                 185                 190

Glu Lys Ala Ser Glu Leu Thr Val Gly Asp Lys Ala Lys Leu Val Tyr
        195                 200                 205

Gly Gly Asp Val Tyr Gly Val Ile Glu Ile Ala Asp Ile Tyr Arg Pro
    210                 215                 220

Asp Lys Thr Lys Glu Ala Lys Leu Val Tyr Lys Thr Asp Glu Leu Ala
225                 230                 235                 240

His Pro Gly Val Arg Lys Leu Phe Glu Lys Pro Asp Val Tyr Val Gly
                245                 250                 255

Gly Ala Val Thr Leu Val Lys Arg Thr Asp Lys Gly Gln Phe Ala Pro
            260                 265                 270

Phe Tyr Phe Asp Pro Ala Glu Thr Arg Lys Arg Phe Ala Glu Leu Gly
        275                 280                 285

Trp Asn Thr Val Val Gly Phe Gln Thr Arg Asn Pro Val His Arg Ala
    290                 295                 300
```

His6-BCCP Bst Sulfurylase Amino Acid Sequence

```
His Glu Tyr Ile Gln Lys Cys Ala Leu Glu Ile Val Asp Gly Leu Phe
305             310                 315             320

Leu Asn Pro Leu Val Gly Glu Thr Lys Ala Asp Asp Ile Pro Ala Asp
            325                 330             335

Ile Arg Met Glu Ser Tyr Gln Val Leu Leu Glu Asn Tyr Tyr Pro Lys
            340                 345             350

Asp Arg Val Phe Leu Gly Val Phe Gln Ala Ala Met Arg Tyr Ala Gly
        355                 360             365

Pro Arg Glu Ala Ile Phe His Ala Met Val Arg Lys Asn Phe Gly Cys
        370             375             380

Thr His Phe Ile Val Gly Arg Asp His Ala Gly Val Gly Asn Tyr Tyr
385             390                 395             400

Gly Thr Tyr Asp Ala Gln Lys Ile Phe Ser Asn Phe Thr Ala Glu Glu
            405                 410             415

Leu Gly Ile Thr Pro Leu Phe Phe Glu His Ser Phe Tyr Cys Thr Lys
            420                 425             430

Cys Glu Gly Met Ala Ser Thr Lys Thr Cys Pro His Asp Ala Gln Tyr
            435                 440             445

His Val Val Leu Ser Gly Thr Lys Val Arg Glu Met Leu Arg Asn Gly
        450                 455             460

Gln Val Pro Pro Ser Thr Phe Ser Arg Pro Glu Val Ala Ala Val Leu
465             470                 475             480

Ile Lys Gly Leu Gln Glu Arg Glu Thr Val Ala Pro Ser Ala Arg
                485                 490             495
```

Another aspect of the invention pertains to vectors, preferably expression vectors, containing a nucleic acid encoding an ATP generating polypeptide and an ATP converting polypeptide, or derivatives, fragments, analogs or homologs thereof. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid in a form suitable for expression of the nucleic acid in a host cell, which means that the recombinant expression vectors include one or more regulatory sequences, selected on the basis of the host cells to be used for expression, that is operatively linked to the nucleic acid sequence to be expressed. Within a recombinant expression vector, "operably linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g. tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce a fusion protein.

The recombinant expression vectors of the invention can be designed for expression of the fusion protein in prokaryotic or eukaryotic cells. For example, a sulfurylase-luciferase fusion protein can be expressed in bacterial cells such as *E. coli*, insect cells (using baculovirus expression vectors) yeast cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in E. coli with vectors containing constitutive or inducible promoters directing the expression. Fusion vectors add a number of amino acids to a protein encoded therein, usually to the amino terminus of the recombinant protein. Such fusion vectors typically serve three purposes: (1) to increase expression of recombinant protein; (2) to increase the solubility of the recombinant protein; and (3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein.

In another embodiment, the ATP generating-ATP converting fusion protein expression vector is a yeast expression vector. Examples of vectors for expression in yeast S. cerivisae include pYepSec1 (Baldari, et al., (1987) EMBO J 6:229–234), pMFa (Kurjan and Herskowitz, (1982) Cell 30:933–943), pJRY88 (Schultz et al., (1987) Gene 54:113–123), pYES2 (Invitrogen Corporation, San Diego, Calif.), and picZ (Invitrogen Corp, San Diego, Calif.).

Alternatively, the fusion protein can be expressed in insect cells using baculovirus expression vectors. Baculovirus vectors available for expression of proteins in cultured insect cells (e.g., SF9 cells) include the pAc series (Smith et al. (1983) Mol Cell Biol 3:2156–2165) and the pVL series (Lucklow and Summers (1989) Virology 170:31–39).

In yet another embodiment, a nucleic acid of the invention is expressed in mammalian cells using a mammalian expression vector. Examples of mammalian expression vectors include pCDM8 (Seed (1987) Nature 329:840) and pMT2PC (Kaufman et al. (1987) EMBO J 6: 187–195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells. See, e.g., Chapters 16 and 17 of Sambrook et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) Genes Dev 1:268–277), lymphoid-specific promoters (Calame and Eaton (1988) Adv Immunol 43:235–275), in particular promoters of T cell receptors (Winoto and Baltimore (1989) EMBO J 8:729–733) and immunoglobulins (Banerji et al. (1983) Cell 33:729–740; Queen and Baltimore (1983) Cell 33:741–748), neuron-specific promoters (e.g., the neurofilament promoter; Byrne and Ruddle (1989) PNAS 86:5473–5477), pancreas-specific promoters (Edlund et al. (1985) Science 230:912–916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss (1990) Science 249:374–379) and the α-fetoprotein promoter (Campes and Tilghman (1989) Genes Dev 3:537–546).

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein. The invention also includes a kit comprising a sulfurylase-luciferase fusion protein expression vector.

A host cell can be any prokaryotic or eukaryotic cell. For example, the sulfurylase-luciferase fusion protein can be expressed in bacterial cells such as E. coli, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding ORFX or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) the fusion protein. Accordingly, the invention further provides methods for producing the fusion protein using the host cells of the invention. In one embodiment, the method comprises culturing the host cell of invention (into which a recombinant expression vector encoding the fusion protein has been introduced) in a suitable medium such that the fusion protein is produced. In another embodiment, the method further comprises isolating the fusion protein from the medium or the host cell.

The invention also includes a fusion protein bound to a mobile support. In a preferred embodiment, the fusion gene is a sulfurylase-luciferase fusion gene. In another embodiment, the mobile support is bound to strepavidin. The mobile support could be a bead or optical fiber. In a preferred embodiment, the bead is a nickel-agarose bead or a MPG-Streptavidin bead. In one embodiment, the sulfurylase-luciferase fusion protein is bound to the beads in a 1:3 ratio of protein to bead. It can be attached to the solid support via a covalent or non-covalent interaction. In general, any linkage recognized in the art can be used. Examples of such linkages common in the art include any suitable metal (e.g., $Co^{2+}$, $Ni^{2+}$)-hexahistidine complex, a biotin binding protein, e.g., NEUTRAVIDIN™ modified avidin (Pierce Chemicals, Rockford, Ill.), streptavidin/biotin, avidin/biotin, glutathione S-transferase (GST)/glutathione, monoclonal antibody/antigen, and maltose binding protein/maltose, and pluronic coupling technologies. Samples containing the appropriate tag are incubated with the sensitized substrate so that zero, one, or multiple molecules attach at each sensitized site.

Acetyl-CoA carboxylase (ACCase) catalyzes the first committed step in de novo fatty acid biosynthesis. It belongs to a group of carboxylases that use biotin as cofactor and bicarbonate as a source of the carboxyl group. There are two types of ACCase: prokaryotic ACCase (e.g., *E. coli, P. aeruginosa, Anabaena, Synechococcus* and probably pea chloroplast) in which the three functional domains: biotin carboxylase (BC), biotin carboxyl carrier protein (BCCP) and carboxyltransferase (CT) are located on separable subunits and eukaryotic ACCase (e.g., rat, chicken, yeast, diatom and wheat) in which all the domains are located on one large polypeptide. It is known that a BCCP as a subunit of acetyl CoA carboxylase from *E. coli* is biotinated at the Lys residue at the 122-position by the action of biotin holoenzyme synthetase in *E. coli* (Journal of Biological Chemistry, 263, 6461 (1988)). In a preferred embodiment of this invention, the fusion protein is bound to a BCCP domain which is then utilized for binding avidins; therefore, it can bind to a streptavidin mobile support. One biotin-(strept-)avidin-based anchoring method uses a thin layer of a photoactivatable biotin analog dried onto a solid surface. (Hengsakul and Cass, 1996. *Bioconjugate Chem.* 7: 249–254). The biotin analog is then exposed to white light through a mask, so as to create defined areas of activated biotin. Avidin (or streptavidin) is then added and allowed to bind to the activated biotin. The avidin possesses free biotin binding sites which can be utilized to "anchor" the biotinylated proteins through a biotin-(strept-)avidin linkage.

Alternatively, the fusion protein can be attached to the solid support with a biotin derivative possessing a photoremovable protecting group. This moiety is covalently bound to bovine serum albumin (BSA), which is attached to the solid support, e.g., a glass surface. See Pirrung and Huang, 1996. *Bioconjugate Chem.* 7: 317–321. A mask is then used to create activated biotin within the defined irradiated areas. Avidin may then be localized to the irradiated area, with a biotinylated sulfurylase-luciferase fusion protein subsequently attached through a BSA-biotin-avidin-biotin link.

Another method of attachment is with the use of a pluronics based attachment. Pluronics attach to hydrophobic surfaces by virtue of the reaction between the hydrophobic surface and the polypropylene oxide. The remaining polyethylene oxide groups extend off the surface, thereby creating a hydrophilic environment. Nitrilotriacetic acid (NTA) can be conjugated to the terminal ends of the polyethylene oxide chains to allow for hexahistidine tagged proteins to be attached.

This invention provides methods of sequencing which utilize and ATP generating polypeptide-ATP converting polypeptide fusion protein for detection. In a preferred embodiment, the nucleotide sequence of the sequencing product is determined by measuring inorganic pyrophosphate (PPi) liberated from a nucleotide triphosphate (dNTP) as the dNMP is incorporated into an extended sequence primer. This method of sequencing is termed Pyrosequencing•technology (PyroSequencing AB, Stockholm, Sweden). It can be performed in solution (liquid phase) or as a solid phase technique. Various sequencing methods, including PPi sequencing methods, are described in, e.g., WO9813523A1, Ronaghi, et al., 1996. Anal. Biochem. 242: 84–89, and Ronaghi, et al., 1998. Science 281: 363–365 (1998), U.S. Pat. No. 6,274,320 and the patent application U.S. Ser. No. 10/104,280 which was filed on Mar. 21, 2001 (21465-501CIP3). These disclosures of sequencing are incorporated herein in their entirety, by reference.

Pyrophosphate released under these conditions can be detected enzymatically (e.g., by the generation of light in the luciferase-luciferin reaction). Such methods enable a nucleotide to be identified in a given target position, and the DNA to be sequenced simply and rapidly while avoiding the need for electrophoresis and the use of potentially dangerous radiolabels.

The invention also provides a method for sequencing nucleic acids which generally comprises (a) providing one or more nucleic acid anchor primers and a plurality of single-stranded circular nucleic acid templates disposed within a plurality of reaction chambers or cavities; (b) annealing an effective amount of the nucleic acid anchor primer to at least one of the single-stranded circular templates to yield a primed anchor primer-circular template complex; (c) combining the primed anchor primer-circular template complex with a polymerase to form an extended anchor primer covalently linked to multiple copies of a nucleic acid complementary to the circular nucleic acid template; (d) annealing an effective amount of a sequencing primer to one or more copies of said covalently linked complementary nucleic acid; (e) extending the sequencing primer with a polymerase and a predetermined nucleotide triphosphate to yield a sequencing product and, if the predetermined nucleotide triphosphate is incorporated onto the 3' end of said sequencing primer, a sequencing reaction byproduct; and (f) identifying the PPi sequencing reaction byproduct with the use of an ATP generating polypeptide-ATP converting polypeptide fusion protein, thereby determining the sequence of the nucleic acid. In one embodiment, a dATP or ddATP analogue is used in place of deoxy- or dideoxy adenosine triphosphate. This analogue is capable of acting as a substrate for a polymerase but incapable of acting as a substrate for a PPi-detection enzyme. This method can be carried out in separate parallel common reactions in an aqueous environment.

In another aspect, the invention includes a method of determining the base sequence of a plurality of nucleotides on an array, which generally comprises (a) providing a plurality of sample DNAs, each disposed within a plurality of cavities on a planar surface; (b) adding an activated nucleotide 5'-triphosphate precursor of one known nitrogenous base to a reaction mixture in each reaction chamber, each reaction mixture comprising a template-directed nucleotide polymerase and a single-stranded polynucleotide template hybridized to a complementary oligonucleotide primer strand at least one nucleotide residue shorter than the templates to form at least one unpaired nucleotide residue in each template at the 3'-end of the primer strand, under reaction conditions which allow incorporation of the activated nucleoside 5'-triphosphate precursor onto the 3'-end of the primer strands, provided the nitrogenous base of the activated nucleoside 5'-triphosphate precursor is complementary to the nitrogenous base of the unpaired nucleotide residue of the templates; (c) utilizing an ATP generating polypeptide-ATP converting polypeptide fusion protein to detect whether or not the nucleoside 5'-triphosphate precursor was incorporated into the primer strands in which incorporation of the nucleoside 5'-triphosphate precursor indicates that the unpaired nucleotide residue of the template has a nitrogenous base composition that is complementary to that of the incorporated nucleoside 5'-triphosphate precursor; and (d) sequentially repeating steps (b) and (c), wherein each sequential repetition adds and, detects the incorporation of one type of activated nucleoside 5'-triphosphate precursor of known nitrogenous base composition; and (e) determining the base sequence of the unpaired nucleotide residues of the template in each reaction chamber from the sequence of incorporation of said nucleoside precursors.

The anchor primers of the invention generally comprise a stalk region and at least one adaptor region. In a preferred embodiment the anchor primer contains at least two contiguous adapter regions. The stalk region is present at the 5' end of the anchor primer and includes a region of nucleotides for attaching the anchor primer to the solid substrate.

The adaptor region(s) comprise nucleotide sequences that hybridize to a complementary sequence present in one or more members of a population of nucleic acid sequences. In some embodiments, the anchor primer includes two adjoining adaptor regions, which hybridize to complementary regions ligated to separate ends of a target nucleic acid sequence. In additional embodiments, the adapter regions in the anchor primers are complementary to non-contiguous regions of sequence present in a second nucleic acid sequence. Each adapter region, for example, can be homologous to each terminus of a fragment produced by digestion with one or more restriction endonucleases. The fragment can include, e.g., a sequence known or suspected to contain a sequence polymorphism. Additionally, the anchor primer may contain two adapter regions that are homologous to a gapped region of a target nucleic acid sequence, i.e., one that is non-contiguous because of a deletion of one or more nucleotides. When adapter regions having these sequences are used, an aligning oligonucleotide corresponding to the gapped sequence may be annealed to the anchor primer along with a population of template nucleic acid molecules.

The anchor primer may optionally contain additional elements such as one or more restriction enzyme recognition sites, RNA polymerase binding sites, e.g., a T7 promoter site, or sequences present in identified DNA sequences, e.g., sequences present in known genes. The adapter region(s) may also include sequences known to flank sequence polymorphisms. Sequence polymorphisms include nucleotide substitutions, insertions, deletions, or other rearrangements which result in a sequence difference between two otherwise identical nucleic acid sequences. An example of a sequence polymorphism is a single nucleotide polymorphism (SNP).

In general, any nucleic acid capable of base-pairing can be used as an anchor primer. In some embodiments, the anchor primer is an oligonucleotide. As utilized herein the term oligonucleotide includes linear oligomers of natural or modified monomers or linkages, e.g., deoxyribonucleosides, ribonucleosides, anomeric forms thereof, peptide nucleic acids (PNAs), and the like, that are capable of specifically binding to a target polynucleotide by way of a regular pattern of monomer-to-monomer interactions. These types of interactions can include, e.g., Watson-Crick type of base-pairing, base stacking, Hoogsteen or reverse-Hoogsteen types of base-pairing, or the like. Generally, the monomers are linked by phosphodiester bonds, or analogs thereof, to form oligonucleotides ranging in size from, e.g., 3–200, 8–150, 10–100, 20–80, or 25–50 monomeric units. Whenever an oligonucleotide is represented by a sequence of letters, it is understood that the nucleotides are oriented in the 5'→3' direction, from left-to-right, and that the letter "A" donates deoxyadenosine, the letter "T" denotes thymidine, the letter "C" denotes deoxycytosine, and the letter "G" denotes deoxyguanosine, unless otherwise noted herein. The oligonucleotides of the present invention can include non-natural nucleotide analogs. However, where, for example, processing by enzymes is required, or the like, oligonucleotides comprising naturally occurring nucleotides are generally required for maintenance of biological function.

Anchor primers are linked to the solid substrate at the sensitized sites. They can be linked by the same method of linkage as described for the fusion protein to the solid support. A region of a solid substrate containing a linked primer is referred to herein as an anchor pad. Thus, by specifying the sensitized states on the solid support, it is possible to form an array or matrix of anchor pads. The anchor pads can be, e.g., small diameter spots etched at evenly spaced intervals on the solid support. The anchor pads can be located at the bottoms of the cavitations or wells if the substrate has been cavitated, etched, or otherwise micromachined as discussed above.

In one embodiment, the anchor primer is linked to a particle. The anchor primer can be linked to the particle prior to formation of the extended anchor primer or after formation of the extended anchor primer.

Each sensitized site on a solid support is potentially capable of attaching multiple anchor primers. Thus, each anchor pad may include one or more anchor primers. It is preferable to maximize the number of pads that have only a single productive reaction center (e.g., the number of pads that, after the extension reaction, have only a single sequence extended from the anchor primer). This can be accomplished by techniques which include, but are not limited to: (i) varying the dilution of biotinylated anchor primers that are washed over the surface; (ii) varying the incubation time that the biotinylated primers are in contact with the avidin surface; (iii) varying the concentration of open- or closed-circular template so that, on average, only one primer on each pad is extended to generate the sequencing template; or (iv) reducing the size of the anchor pad to approach single-molecule dimensions (<1 $\mu$m) such that binding of one anchor inhibits or blocks the binding of another anchor (e.g. by photoactivation of a small spot); or (v) reducing the size of the anchor pad such that binding of one circular template inhibits or blocks the binding of a second circular template.

In some embodiments, each individual pad contains just one linked anchor primer. Pads having only one anchor primer can be made by performing limiting dilutions of a selected anchor primer on to the solid support such that, on average, only one anchor primer is deposited on each pad. The concentration of anchor primer to be applied to a pad can be calculated utilizing, for example, a Poisson distribution model.

In order to maximize the number of reaction pads that contain a single anchor primer, a series of dilution experiments are performed in which a range of anchor primer concentrations or circular template concentrations are varied. For highly dilute concentrations of primers, primers and circular templates binding to the same pad will be independent of each other, and a Poisson distribution will characterize the number of anchor primers extended on any one pad. Although there will be variability in the number of primers that are actually extended, a maximum of 37% of the pads will have a single extended anchor primer (the number of pads with a single anchor oligonucleotide).

In other embodiments multiple anchor primers are attached to any one individual pad in an array. Limiting dilutions of a plurality of circular nucleic acid templates (described in more detail below) may be hybridized to the anchor primers so immobilized such that, on average, only one primer on each pad is hybridized to a nucleic acid template. Library concentrations to be used may be calculated utilizing, for example, limiting dilutions and a Poisson distribution model.

The nucleic acid templates that can be sequenced according to the invention, e.g., a nucleic acid library, in general can include open circular or closed circular nucleic acid molecules. A "closed circle" is a covalently closed circular nucleic acid molecule, e.g., a circular DNA or RNA molecule. An "open circle" is a linear single-stranded nucleic acid molecule having a 5' phosphate group and a 3' hydroxyl group. In one embodiment, the single stranded nucleic acid contains at least 100 copies of nucleic acid sequence, each copy covalently linked end to end. In some embodiments, the open circle is formed in situ from a linear double-stranded nucleic acid molecule. The ends of a given open circle nucleic acid molecule can be ligated by DNA ligase. Sequences at the 5' and 3' ends of the open circle molecule are complementary to two regions of adjacent nucleotides in a second nucleic acid molecule, e.g., an adapter region of an anchor primer, or to two regions that are nearly adjoining in a second DNA molecule. Thus, the ends of the open-circle molecule can be ligated using DNA ligase, or extended by DNA polymerase in a gap-filling reaction. Open circles are described in detail in Lizardi, U.S. Pat. No. 5,854,033. An open circle can be converted to a closed circle in the presence of a DNA ligase (for DNA) or RNA ligase following, e.g., annealing of the open circle to an anchor primer.

If desired, nucleic acid templates can be provided as padlock probes. Padlock probes are linear oligonucleotides that include target-complementary sequences located at each end, and which are separated by a linker sequence. The linkers can be ligated to ends of members of a library of nucleic acid sequences that have been, e.g., physically sheared or digested with restriction endonucleases. Upon hybridization to a target-sequence, the 5'- and 3'-terminal regions of these linear oligonucleotides are brought in juxtaposition. This juxtaposition allows the two probe segments (if properly hybridized) to be covalently-bound by enzymatic ligation (e.g., with T4 DNA ligase), thus converting the probes to circularly-closed molecules which are catenated to the specific target sequences (see e.g., Nilsson, et al., 1994. *Science* 265: 2085–2088). The resulting probes are suitable for the simultaneous analysis of many gene sequences both due to their specificity and selectivity for gene sequence variants (see e.g., Lizardi, et al., 1998. *Nat. Genet.* 19: 225–232; Nilsson, et al., 1997. *Nat. Genet.* 16: 252–255) and due to the fact that the resulting reaction products remain localized to the specific target sequences. Moreover, intramolecular ligation of many different probes is expected to be less susceptible to non-specific cross-reactivity than multiplex PCR-based methodologies where non-cognate pairs of primers can give rise to irrelevant amplification products (see e.g., Landegren and Nilsson, 1997. *Ann. Med.* 29: 585–590).

A starting library can be constructed comprising either single-stranded or double-stranded nucleic acid molecules, provided that the nucleic acid sequence includes a region that, if present in the library, is available for annealing, or can be made available for annealing, to an anchor primer sequence. For example, when used as a template for rolling circle amplification, a region of a double-stranded template needs to be at least transiently single-stranded in order to act as a template for extension of the anchor primer.

Library templates can include multiple elements, including, but not limited to, one or more regions that are complementary to the anchor primer. For example, the template libraries may include a region complementary to a sequencing primer, a control nucleotide region, and an insert sequence comprised of the sequencing template to be subsequently characterized. As is explained in more detail below, the control nucleotide region is used to calibrate the relationship between the amount of byproduct and the number of nucleotides incorporated. As utilized herein the term "complement" refers to nucleotide sequences that are able to hybridize to a specific nucleotide sequence to form a matched duplex.

In one embodiment, a library template includes: (i) two distinct regions that are complementary to the anchor primer, (ii) one region homologous to the sequencing primer, (iii) one optional control nucleotide region, (iv) an insert sequence of, e.g., 30–500, 50–200, or 60–100 nucleotides, that is to be sequenced. The template can, of course, include two, three, or all four of these features.

The template nucleic acid can be constructed from any source of nucleic acid, e.g., any cell, tissue, or organism, and can be generated by any art-recognized method. Suitable methods include, e.g., sonication of genomic DNA and digestion with one or more restriction endonucleases (RE) to generate fragments of a desired range of lengths from an initial population of nucleic acid molecules. Preferably, one or more of the restriction enzymes have distinct four-base recognition sequences. Examples of such enzymes include, e.g., Sau3A1, MspI, and TaqI. Preferably, the enzymes are used in conjunction with anchor primers having regions containing recognition sequences for the corresponding restriction enzymes. In some embodiments, one or both of the adapter regions of the anchor primers contain additional sequences adjoining known restriction enzyme recognition sequences, thereby allowing for capture or annealing to the anchor primer of specific restriction fragments of interest to the anchor primer. In other embodiments, the restriction enzyme is used with a type IIS restriction enzyme.

Alternatively, template libraries can be made by generating a complementary DNA (cDNA) library from RNA, e.g., messenger RNA (mRNA). The cDNA library can, if desired, be further processed with restriction endonucleases to obtain a 3' end characteristic of a specific RNA, internal fragments, or fragments including the 3 end of the isolated RNA. Adapter regions in the anchor primer may be complementary to a sequence of interest that is thought to occur in the template library, e.g., a known or suspected sequence polymorphism within a fragment generated by endonuclease digestion.

In one embodiment, an indexing oligonucleotide can be attached to members of a template library to allow for subsequent correlation of a template nucleic acid with a population of nucleic acids from which the template nucleic acid is derived. For example, one or more samples of a starting DNA population can be fragmented separately using any of the previously disclosed methods (e.g., restriction digestion, sonication). An indexing oligonucleotide sequence specific for each sample is attached to, e.g., ligated to, the termini of members of the fragmented population. The indexing oligonucleotide can act as a region for circularization, amplification and, optionally, sequencing, which permits it to be used to index, or code, a nucleic acid so as to identify the starting sample from which it is derived.

Distinct template libraries made with a plurality of distinguishable indexing primers can be mixed together for subsequent reactions. Determining the sequence of the member of the library allows for the identification of a sequence corresponding to the indexing oligonucleotide. Based on this information, the origin of any given fragment can be inferred.

Libraries of nucleic acids are annealed to anchor primer sequences using recognized techniques (see, e.g., Hatch, et al., 1999. *Genet. Anal. Biomol. Engineer.* 15: 35–40; Kool, U.S. Pat. No. 5,714,320 and Lizardi, U.S. Pat. No. 5,854,033). In general, any procedure for annealing the anchor primers to the template nucleic acid sequences is suitable as long as it results in formation of specific, i.e., perfect or nearly perfect, complementarity between the adapter region or regions in the anchor primer sequence and a sequence present in the template library.

A number of in vitro nucleic acid amplification techniques may be utilized to extend the anchor primer sequence. The size of the amplified DNA preferably is smaller than the size of the anchor pad and also smaller than the distance between anchor pads.

The amplification is typically performed in the presence of a polymerase, e.g., a DNA or RNA-directed DNA polymerase, and one, two, three, or four types of nucleotide triphosphates, and, optionally, auxiliary binding proteins. In general, any polymerase capable of extending a primed 3'-OH group can be used a long as it lacks a 3' to 5' exonuclease activity. Suitable polymerases include, e.g., the DNA polymerases from *Bacillus stearothermophilus*, *Thermus acquaticus*, *Pyrococcus furiosis*, *Thermococcus litoralis*, and *Thermus thermophilus*, bacteriophage T4 and T7, and the *E. coli* DNA polymerase I Klenow fragment. Suitable RNA-directed DNA polymerases include, e.g., the reverse transcriptase from the Avian Myeloblastosis Virus, the reverse transcriptase from the Moloney Murine Leukemia Virus, and the reverse transcriptase from the Human Immunodeficiency Virus-I.

A number of in vitro nucleic acid amplification techniques have been described. These amplification methodologies may be differentiated into those methods: (i) which require temperature cycling—polymerase chain reaction (PCR) (see e.g., Saiki, et al., 1995. *Science* 230: 1350–1354), ligase chain reaction (see e.g., Barany, 1991. *Proc. Natl. Acad. Sci. USA* 88: 189–193; Barringer, et al., 1990. *Gene* 89: 117–122) and transcription-based amplification (see e.g., Kwoh, et al, 1989. *Proc. Natl. Acad. Sci. USA* 86: 1173–1177) and (ii) isothermal amplification systems—self-sustaining, sequence replication (see e.g., Guatelli, et al., 1990. *Proc. Natl. Acad. Sci. USA* 87: 1874–1878); the Qβ replicase system (see e.g., Lizardi, et al., 1988. *BioTechnology* 6: 1197–1202); strand displacement amplification Nucleic Acids Res. Apr. 11, 1992;20(7):1691–6.; and the methods described in PNAS Jan. 1, 1992;89(1):392–6; and NASBA J Virol Methods. 1991 December;35(3):273–86.

Isothermal amplification also includes rolling circle-based amplification (RCA). RCA is discussed in, e.g., Kool, U.S. Pat. No. 5,714,320 and Lizardi, U.S. Pat. No. 5,854,033; Hatch, et al., 1999. *Genet. Anal. Biomol. Engineer.* 15: 35–40. The result of the RCA is a single DNA strand extended from the 3' terminus of the anchor primer (and thus is linked to the solid support matrix) and including a concatamer containing multiple copies of the circular template annealed to a primer sequence. Typically, 1,000 to 10,000 or more copies of circular templates, each having a size of, e.g., approximately 30–500, 50–200, or 60–100 nucleotides size range, can be obtained with RCA.

In vivo, RCR is utilized in several biological systems. For example, the genome of several bacteriophage are single-stranded, circular DNA. During replication, the circular DNA is initially converted to a duplex form, which is then replicated by the aforementioned rolling-circle replication mechanism. The displaced terminus generates a series of genomic units that can be cleaved and inserted into the phage particles. Additionally, the displaced single-strand of a rolling-circle can be converted to duplex DNA by synthesis of a complementary DNA strand. This synthesis can be used to generate the concatemeric duplex molecules required for the maturation of certain phage DNAs. For example, this provides the principle pathway by which λ bacteriophage matures. RCR is also used in vivo to generate amplified rDNA in *Xenopus oocytes*, and this fact may help explain why the amplified rDNA is comprised of a large number of identical repeating units. In this case, a single genomic repeating unit is converted into a rolling-circle. The displaced terminus is then converted into duplex DNA which is subsequently cleaved from the circle so that the two termini can be ligated together so as to generate the amplified circle of rDNA.

Through the use of the RCA reaction, a strand may be generated which represents many tandem copies of the complement to the circularized molecule. For example, RCA has recently been utilized to obtain an isothermal cascade amplification reaction of circularized padlock probes in vitro in order to detect single-copy genes in human genomic DNA samples (see Lizardi, et al., 1998. *Nat. Genet.* 19: 225–232). In addition, RCA has also been utilized to detect single DNA molecules in a solid phase-based assay, although difficulties arose when this technique was applied to in situ hybridization (see Lizardi, et al., 1998. *Nat. Genet.* 19: 225–232).

If desired, RCA can be performed at elevated temperatures, e.g., at temperatures greater than 37° C., 42° C., 45° C., 50° C., 60° C., or 70° C. In addition initially at a lower temperature, e.g., room temperature, and then shifted to an elevated temperature. Elevated temperature RCA is preferably performed with thermostable nucleic acid polymerases and with primers that can anneal stably and with specificity at elevated temperatures.

RCA can also be performed with non-naturally occurring oligonucleotides, e.g., peptide nucleic acids. Further, RCA can be performed in the presence of auxiliary proteins such as single-stranded binding proteins.

The development of a method of amplifying short DNA molecules which have been immobilized to a solid support, termed RCA has been recently described in the literature (see e.g., Hatch, et al., 1999. *Genet. Anal. Biomol. Engineer.* 15: 35–40; Zhang, et al., 1998. *Gene* 211: 277–85; Baner, et al., 1998. *Nucl. Acids Res.* 26: 5073–5078; Liu, et al., 1995. *J. Am. Chem. Soc.* 118: 1587–1594; Fire and Xu, 1995. *Proc. Natl. Acad. Sci. USA* 92: 4641–4645; Nilsson, et al., 1994. *Science* 265: 2085–2088). RCA targets specific DNA sequences through hybridization and a DNA ligase reaction. The circular product is then subsequently used as a template in a rolling circle replication reaction.

RCA driven by DNA polymerase can replicate circularized oligonucleotide probes with either linear or geometric kinetics under isothermal conditions. In the presence of two primers (one hybridizing to the +strand, and the other, to the −strand of DNA), a complex pattern of DNA strand displacement ensues which possesses the ability to generate $1\times10^9$ or more copies of each circle in a short period of time (i.e., less-than 90 minutes), enabling the detection of single-point mutations within the human genome. Using a single primer, RCA generates hundreds of randomly-linked copies of a covalently closed circle in several minutes. If solid support matrix-associated, the DNA product remains bound at the site of synthesis, where it may be labeled, condensed, and imaged as a point light source. For example, linear oligonucleotide probes, which can generate RCA signals, have been bound covalently onto a glass surface. The color of the signal generated by these probes indicates the allele status of the target, depending upon the outcome of specific, target-directed ligation events. As RCA permits millions of individual probe molecules to be counted and sorted, it is particularly amenable for the analysis of rare somatic mutations. RCA also shows promise for the detection of padlock probes bound to single-copy genes in cytological preparations.

In addition, a solid-phase RCA methodology has also been developed to provide an effective method of detecting constituents within a solution. Initially, a recognition step is used to generate a complex h a circular template is bound to a surface. A polymerase enzyme is then used to amplify the bound complex. RCA uses small DNA probes that are amplified to provide an intense signal using detection methods, including the methods described in more detail below.

Other examples of isothermal amplification systems include, e.g., (i) self-sustaining, sequence replication (see e.g., Guatelli, et al., 1990. *Proc. Natl. Acad. Sci. USA* 87: 1874–1878), (ii) the Qβ replicase system (see e.g., Lizardi, et al., 1988. *BioTechnology* 6: 1197–1202), and (iii) nucleic acid sequence-based amplification (NASBA™; see Kievits, et al., 1991. *J. Virol. Methods* 35: 273–286).

Amplification of a nucleic acid template as described above results in multiple copies of a template nucleic acid sequence covalently linked to an anchor primer. In one embodiment, a region of the sequence product is determined by annealing a sequencing primer to a region of the template nucleic acid, and then contacting the sequencing primer with a DNA polymerase and a known nucleotide triphosphate, i.e., dATP, dCTP, dGTP, dTTP, or an analog of one of these nucleotides. The sequence can be determined by detecting a sequence reaction byproduct, as is described below.

The sequence primer can be any length or base composition, as long as it is capable of specifically annealing to a region of the amplified nucleic acid template. No particular structure for the sequencing primer is required so long as it is able to specifically prime a region on the amplified template nucleic acid. Preferably, the sequencing primer is complementary to a region of the template that is between the sequence to be characterized and the sequence hybridizable to the anchor primer. The sequencing primer is extended with the DNA polymerase to form a sequence product. The extension is performed in the presence of one or more types of nucleotide triphosphates, and if desired, auxiliary binding proteins.

The method comprises the steps of: (a) introducing the template nucleic acid polymer into a polymerization environment in which the nucleic acid polymer will act as a template polymer for the synthesis of a complementary nucleic acid polymer when nucleotides are added; (b) successively providing to the polymerization environment a series of feedstocks, each feedstock comprising a nucleotide selected from among the nucleotides from which the complementary nucleic acid polymer will be formed, such that if the nucleotide in the feedstock is complementary to the next nucleotide in the template polymer to be sequenced said nucleotide will be incorporated into the complementary polymer and inorganic pyrophosphate will be released; (c) separately recovering each of the feedstocks from the polymerization environment; and (d) measuring the amount of inorganic pyrophosphate by utilizing an ATP generating polypeptide-ATP converting polypeptide fusion protein in each of the recovered feedstocks to determine the identity of each nucleotide in the complementary polymer and thus the sequence of the template polymer.

The sequence primer can be any length or base composition, as long as it is capable of specifically annealing to a region of the amplified nucleic acid template. No particular structure is required for the sequencing primer so long as it is able to specifically prime a region on the amplified template nucleic acid. Preferably, the sequencing primer is complementary to a region of the template that is between the sequence to be characterized and the sequence hybridizable to the anchor primer. The sequencing primer is extended with the DNA polymerase to form a sequence product. The extension is performed in the presence of one or more types of nucleotide triphosphates, and if desired, auxiliary binding proteins.

This invention also includes a method wherein the amount of inorganic pyrophosphate is measured by (a) adding adenosine-5'-phosphosulfate to the feedstock; combining the recovered feedstock containing adenosine-5'-phosphosulfate with an ATP generating polypeptide-ATP converting polypeptide fusion protein such that any inorganic pyrophosphate in the recovered feedstock and the adenosine-5'-phosphosulfate will first react to the form ATP and sulfate and then react with luciferin in the presence of oxygen such that the ATP is consumed to produced AMP, inorganic pyrophosphate, carbon dioxide and light; and (b) measuring the amount of light produced. In a preferred embodiment, the template polymer and ATP generating polypeptide-ATP converting polypeptide fusion protein are immobilized on a solid support.

The invention also includes a method for determining the nucleic acid sequence in a template nucleic acid polymer, comprising: (a) introducing the template nucleic acid polymer into a polymerization environment in which the nucleic acid polymer will act as a template polymer for the synthesis of a complementary nucleic acid polymer when nucleotides are added; (b) successively providing to the polymerization environment a series of feedstocks, each feedstock comprising a nucleotide selected from among the nucleotides from which the complementary nucleic acid polymer will be formed, such that if the nucleotide in the feedstock is complementary to the next nucleotide in the template polymer to be sequenced said nucleotide will be incorporated into the complementary polymer and inorganic pyrophosphate will be released; (c) separately recovering each of the feedstocks from the polymerization environment; and (d) measuring the amount of PPi with a thermostable sulfurylase and a luciferase in each of the recovered feedstocks to determine the identity of each nucleotide in the complementary polymer and thus the sequence of the template polymer. In one embodiment, the thermostable sulfurylase and the luciferase are joined in a fusion protein. In another embodiment, the thermostable sulfurylase is joined to an affinity tag.

The invention further provides a method for sequencing a nucleic acid, the method comprising: (a) providing one or more nucleic acid anchor primers; (b) providing a plurality of single-stranded circular nucleic acid templates disposed within a plurality of cavities on a planar surface, each cavity forming an analyte reaction chamber, wherein the reaction chambers have a center to center spacing of between 5 to 200; (c) annealing an effective amount of the nucleic acid anchor primer to at least one of the single-stranded circular templates to yield a primed anchor primer-circular template complex; (d) combining the primed anchor primer-circular template complex with a polymerase to form an extended anchor primer covalently linked to multiple copies of a nucleic acid complementary to the circular nucleic acid template; (e) annealing an effective amount of a sequencing primer to one or more copies of said covalently linked complementary nucleic acid; (f) extending the sequencing primer with a polymerase and a predetermined nucleotide triphosphate to yield a sequencing product and, if the predetermined nucleotide triphosphate is incorporated onto the 3' end of said sequencing primer, a sequencing reaction byproduct; and (g) identifying the sequencing reaction byproduct with the use of a thermostable sulfurylase and a luciferase, thereby determining the sequence of the nucleic acid. In one embodiment, the thermostable sulfurylase and the luciferase are joined in a fusion protein. In another embodiment, the thermostable sulfurylase is joined to an affinity tag.

Also included in the invention is a method for sequencing a nucleic acid, the method comprising: (a) providing at least one nucleic acid anchor primer; (b) providing a plurality of single-stranded circular nucleic acid templates in an array having at least 400,000 discrete reaction sites; (c) annealing a first amount of the nucleic acid anchor primer to at least one of the single-stranded circular templates to yield a primed anchor primer-circular template complex; (d) combining the primed anchor primer-circular template complex with a polymerase to form an extended anchor primer covalently linked to multiple copies of a nucleic acid complementary to the circular nucleic acid template; (e) annealing a second amount of a sequencing primer to one or more copies of the covalently linked complementary nucleic acid; (f) extending the sequencing primer with a polymerase and a predetermined nucleotide triphosphate to yield a sequencing product and, when the predetermined nucleotide triphosphate is incorporated onto the 3' end of the sequencing primer, to yield a sequencing reaction byproduct; and (g) identifying the sequencing reaction byproduct with the use of a thermostable sulfurylase and a luciferase, thereby determining the sequence of the nucleic acid at each reaction site that contains a nucleic acid template. In one embodiment, the thermostable sulfurylase and the luciferase are joined in a fusion protein. In another embodiment, the thermostable sulfurylase is joined to an affinity tag.

The invention also includes a method of determining the base sequence of a plurality of nucleotides on an array, the method comprising: (a) providing a plurality of sample DNAs, each disposed within a plurality of cavities on a planar surface, each cavity forming an analyte reaction chamber, wherein the reaction chambers have a center to center spacing of between 5 to 200 $\mu$m, (b) adding an activated nucleotide 5'-triphosphate precursor of one known nitrogenous base to a reaction mixture in each reaction chamber, each reaction mixture comprising a template-directed nucleotide polymerase and a single-stranded polynucleotide template hybridized to a complementary oligonucleotide primer strand at least one nucleotide residue shorter than the templates to form at least one unpaired nucleotide residue in each template at the 3'-end of the primer strand, under reaction conditions which allow incorporation of the activated nucleoside 5'-triphosphate precursor onto the 3'-end of the primer strands, provided the nitrogenous base of the activated nucleoside 5'-triphosphate precursor is complementary to the nitrogenous base of the unpaired nucleotide residue of the templates; (c) detecting whether or not the nucleoside 5'-triphosphate precursor was incorporated into the primer strands through detection of a sequencing byproduct with a thermostable sulfurylase and luciferase, thus indicating that the unpaired nucleotide residue of the template has a nitrogenous base composition that is complementary to that of the incorporated nucleoside 5'-triphosphate precursor; and (d) sequentially repeating steps (b) and (c), wherein each sequential repetition adds and, detects the incorporation of one type of activated nucleoside 5'-triphosphate precursor of known nitrogenous base composition; and (e) determining the base sequence of the unpaired nucleotide residues of the template in each reaction chamber from the sequence of incorporation of said nucleoside precursors. In one embodiment, the thermostable sulfurylase and the luciferase are joined in a fusion protein. In another embodiment, the thermostable sulfurylase is joined to an affinity tag.

The invention will be further illustrated in the following non-limiting examples. There are several abbreviations which will be used in the following examples: FUS stands for fusion gene, S stands for sulfurylase, L stands for luciferase, TL stands for thermostable luciferase, X stands for XhoI, H stands for HindIII, N stands for NotI and B stands for BamHI. For example, FUS-L/S X F means a primer for the fusion gene, luciferase-sulfurylase Xho Forward and so forth. Primers 1 through 6 are for the L or TL to S fusions and primers 7 through 13 are for the S to L or TL fusions.

EXAMPLES

Example 1

Cloning Strategy for Obtaining the Bst Sulfurylase Gene

Gene specific primers, which incorporated restriction site linkers, were designed based on the sequence for a putative ATP sulfurylase from *Bacillus stearothermophilus* in ERGO, a curated database of genomic DNA made available on the World Wide Web by Integrated Genomics which included the *Bacillus stearothermophilus* Genome Sequencing Project at the University of Oklahoma (NSF Grant #EPS-9550478). The forward primer utilized was 5'-CCC TTC TGC AGC ATG AGC GTA AGC ATC CCG CAT GGC GGC ACA TTG-3' (SEQ ID NO: 7) and the reverse primer used was 5'-CCC GTA AGC TTT TAG CGC GCT GAC GGG GCG ACC GTT TCG CGT TCT TG-3' (SEQ ID NO:8). The reaction mix for PCR amplification contained 5.0 uL 10× polymerase buffer (Clontech, Cat. #8714), 2.0 uL 5 M betaine (Sigma, Cat. #B0300), 1.0 uL dNTP mix (10 mM each dATP, dCTP, dGTP, dTTP), 0.8 uL Advantage 2 polymerase (Clontech, Cat. #8714), 0.2 uL Advantage-HF 2 polymerase (Clontech, Cat. #K1914), 10 pmol forward primer, 10 pmol reverse primer, 100 ng (or less) Bst genomic DNA (ATCC, Cat. #12980D), and enough distilled water to make total volume of 50 uL. As little as 1 ng Bst genomic DNA was sufficient to yield PCR product. The PCR amplification of Bst ATP sulfurylase gene from genomic DNA consisted of an initial step at 96° C. for 3 min, then 35 cycles of 96° C. for 15 sec, 60° C. for 30 sec, 72° C. for 6 min, a finishing step at 72° C. for 10 min and finally 14° C. until removal. The PCR product was cleaned using QIAquick PCR Purification Kit (QIAGEN).

Example 2

Cloning Strategy for Obtaining the Sulfurylase-luciferase Fusion Protein

All chemicals were purchased from Sigma unless noted otherwise. Racemically pure D-luciferin was ordered from Pierce. The assay buffer for measuring ATP sulfurylase and luciferase activities contained Taq polymerase. A polymerase chain reaction (PCR)-mediated approach was utilized to link the open reading frames (ORFs) of luciferase and sulfurylase. The cloning strategy is outlined in FIG. 1. Briefly, it involved the amplification of luciferase and sulfurylase ORFs by PCR, using primers that contain convenient restriction sites (XhoI and HindIII) to clone the fusion gene into an expression vector, in-frame and, the design of a rare restriction site (NotI) at the junction of the two polypeptides so that other versions of luciferase, such as thermostable luciferase (TL), and sulfurylase can be conveniently swapped to obtain either sulfurlyase-luciferase (S-L) or luciferase-sulfurlyase (L-S) fusion proteins. A NotI site was used to fuse the variable heavy chain of antibodies to luciferase to generate a viable fusion protein. These primers were also designed in such a way that the primers that form part of the junction of the two ORFs contain sufficient overlapping regions of nucleotides. For example, the 5' end of FUS-L/S Not R contains deoxynucleotides in an anti-parallel orientation that encode the N-terminal 10 amino acids of yeast sulfurylase. Thus, a PCR product generated using this primer would anneal to the 5' end of yeast sulfurylase ORF and would generate the fusion protein, L-S.

Figure 2:
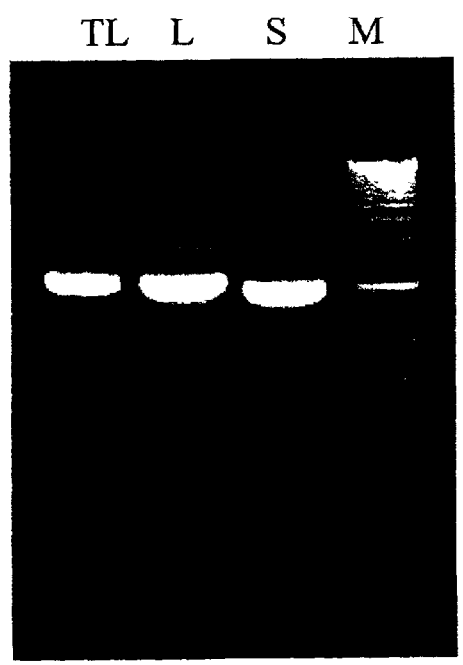
FIGS. 2A and 2B show the preparative agarose gel of luciferase and sulfurylase as well as sulfurylase-luciferase fusion genes.
Figure 2:
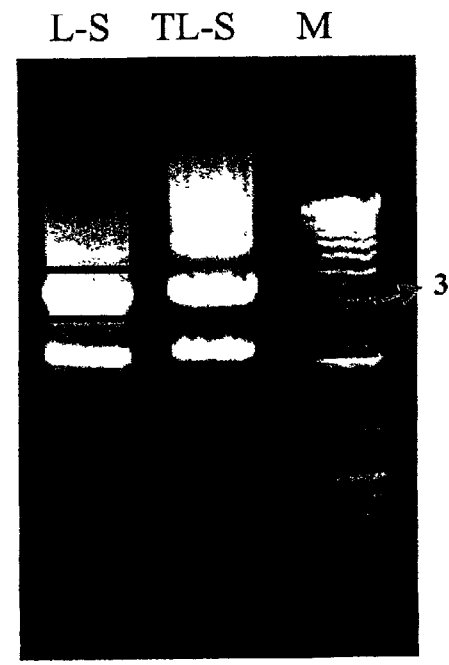
Figure 3:
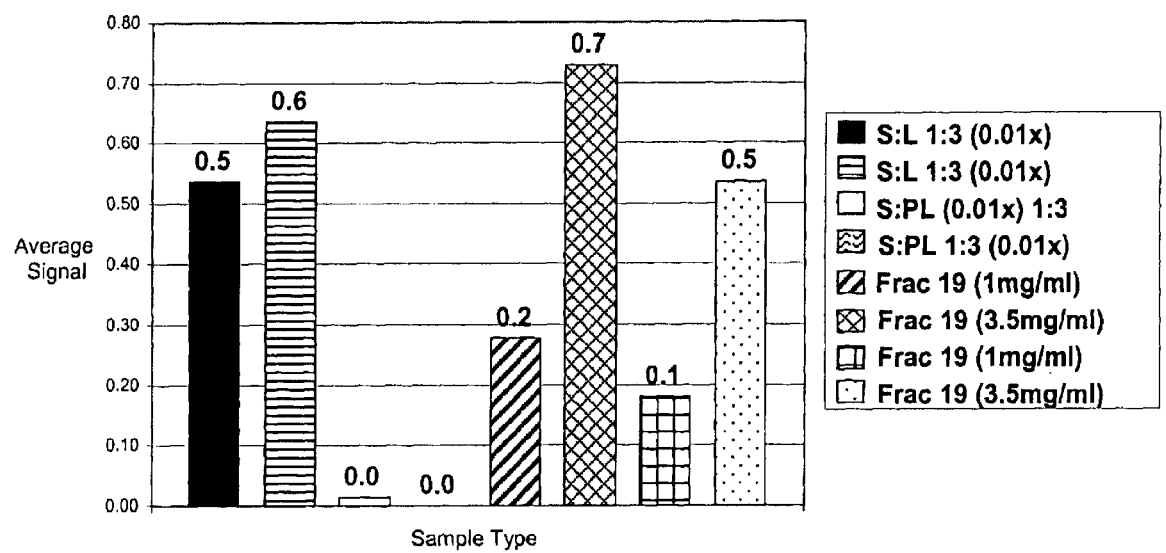
FIG. 3 shows the results of experiments to determine the activity of the luciferase-sulfurylase fusion protein on NTA-agarose and MPG-SA solid supports.

The products in boxes were obtained by PCR as elaborated in FIG. 2. As shown in FIG. 3, the PCR products were subjected to electrophoresis. The PCR products were then purified, digested with XhoI and Hind III and subcloned into XhoI/HindIII digested pRSETA-BCCP. pRSETA-BCCP is a derivative of pRSET A (Invitrogen) in which the sequence between NheI and BamHI restriction sites has been replaced by the portion of the biotin carboxyl carrier protein (BCCP) gene from *E. coli* (GenBank accession #M80458) that codes for residues 87–165. The 87-amino acid BCCP domain was obtained by PCR and cloned into the NheI and BamHI sites of pRSETA to obtain pRSETA-BCCP. The ligated fusion protein and pRSETA-BCCP were transformed into BL21DE3 and TOP10 cells. BL21DE3 cells yielded colonies for L-S and TOP10 cells yielded colonies for TL-S.

The following list of primers was used to construct the fusion proteins:

| PRIMER NO | TITLE | NUCLEIC ACID SEQUENCE | SEQ ID NO |
|---|---|---|---|
| 1 | FUS-L/S X F | CCCC CTC GAG ATC CAA ATG GAA GAC GCC AAA AAC ATA AAG AAA GGC CC | 9 |
| 2 | FUS-TL/S X F | CCCC CTC GAG ATC CAA ATG GCT GAC AAA AAC ATC TGT TAT GGC CC | 10 |
| 3 | FUS-L/S Not R | TTG TAG AAT ACC ACC GTG AGG AGC AGG CAT AGC GGC CGC CAA TTT GGA CTT TCC GCC CTT CTT GGC C | 11 |
| 4 | FUS-TL/S Not R | TTG TAG AAT ACC ACC GTG AGG AGC AGG CAT AGC GGC CGC ACC GTT GGT GTG TTT CTC GAA CAT C | 12 |
| 5 | FUS-S-Not F | GCG GCC GCT ATG CCT GCT CCT CAC GGT GGT ATT CTA C | 13 |
| 6 | FUS-S-Hind III R | CCCC AAG CTT TTA AAA TAC AAA AAA GCC ATT GTC TTC CAA GAA TAG GAC | 14 |
| 7 | FUS-S/L B F | CCCC GGA TCC ATC CAA ATG CCT GCT CCT CAC GGT GGT ATT CTA CAA GAC | 15 |
| 8 | FUS-S/L R | GGGCCTTTCTTTATGTTTTTGGCGTCTT CCAT AGC GGC CGC AAA TAC AAA AAA GCC ATT GTC | 16 |
| 9 | FUS-L-F | GCG GCC GCT ATG GAA GAC GCC AAA AAC ATA AAG AAA GGC CC | 17 |
| 10 | FUS-L-N-R | CCCC CCA TGG TTA CAA TTT GGA CTT TCC GCC CTT CTT GGC C | 18 |
| 11 | FUS-S/TL R | GG GCC ATA CAG GAT GTT TTT GTC AGC CAT AGC GGC CGC AAA TAC AAA AAA GCC ATT GTC | 19 |
| 12 | FUS-TL-F | GCG GCC GCT ATG GCT GAC AAA AAC ATC TGT TAT GGC CC | 20 |
| 13 | FUS-TL-H-R | CCCC AAG CTT CTA ACC GTT GGT GTG TTT CTC GAA CAT CTG ACG C | 21 |

These primes were utilized to perform PCR. The following PCR condition was used.

PCR Condition

96° C. for 96° C. for 0:15; 76° C. for 0:30; −1° C. per cycle; 72° C. for 6:00;

For 15 cycles; 96° C. for 0:15; 60° C. for 0:30; 72° C. for 6:00;

For 29 cycles; 72° C. for 10:00;

14° C. forever

Example 3

Cloning of the His6-BCCP Bst ATP Sulfurylase Fusion Protein

The Bst-affinity tagged fusion construct is a derivative of pRSETA in which the NheI-XhoI fragment has been replaced by the BCCP domain and the ATP sulfurylase is inserted after the BCCP domain.

Briefly, the BstSulf PCR product, as described in Example 1, was double-digested with PstI and HindIII, isolated on a 1% agarose/TAE gel, purified using QIAEXII (QIAGEN) and ligated into the large PstI/HindiIII fragment of pRSETA-BCCP using the Quick Ligation Kit from NEB according to manufacturer's instructions. As mentioned in Example 2, pRSETA-BCCP is a derivative of pRSET A (Invitrogen) in which the sequence between NheI and BamHI restriction sites has been replaced by the portion of the biotin carboxyl carrier protein (BCCP) gene from *E. coli* (GenBank accession #M80458) that codes for residues 87–165. 2 μL ligation reaction was used to transform 50 uL TOP10 competent cells (Invitrogen) and plated on LB-Ap plates. Sequencing of plasmid insert from ten clones was used to determine the consensus sequence for the ATP sulfurylase gene from ATCC 12980.

The plasmid pRSETA-BCCP-BstSulf was transformed into the *E. coli* expression host BL21 (DE3)pLysS (Novagen) and the induction expression of BstHBSulf was carried out according to the maufacturer's instructions. The cells were harvested and stored as frozen pellets. The pellets were lysed using BugBuster plus Benzonase according to manufacturer's instructions and protein was purified on a 20 mL column packed with Chelating Sepharose Fast Flow (Amersham, Cat. #17–0575–02) and charged with nickel (II). Protein was eluted using a 0–500 mM imidazole gradient. Analysis by SDS-PAGE showed a single band of the correct size.

Example 4

Binding Enzymes to Beads

The BCCP domain enables the *E. coli* to add a single biotin molecule onto a specific lysine residue. Hence these fusion proteins can be bound to solid supports that contain streptavidin. TL-S was successfully cloned into a TA vector. 25 μl of MPG-Streptavidin (CPG, Inc.) or Nickel-agarose (Qiagen) were taken in a 1.5 ml tube and placed on a magnet. The supernatant was removed and the beads were resuspended in 25 μg of His6-BCCP-sulfurylase and 75 μg of His6-BCCP-luciferase. To test the fusion protein, 100 μl of dialyzed fusion protein was bound to the 25 μl of beads. The beads were allowed to mix at room temperature for 1 hr, washed with assay buffer (25 mM Tricine (pH 7.8), 5 mM MgAcetate, 1 mM DTT, 1 mM EDTA, and 1 mg/ml BSA) and assayed for enzyme activities with 1 mM PPi, 4 mM APS and 300 mM D-luciferin. With the nickel-agarose beads, the EDTA was omitted from the assay buffer.

As shown in FIG. 3, these fusion proteins displayed activity on both the NTA- Agarose and MPG-SA beads. S:L 1:3 represents sulfurylase and luciferase bound individually to beads in a 1:3 ratio. Ni-Ag and MPG-SA are nickel-agarose and MPG-Streptavidin beads, respectively. PL is Promega luciferase, which does not have a polyhistidine or a biotin tag on it and hence serves as a negative control. Fraction 19 contains the fusion protein and is active on both kinds of beads. This suggests that the fusion protein was synthesized with a poly-histidine tag and a biotin molecule on the BCCP domain of the fusion protein.

What is claimed is:

1. An isolated polypeptide comprising an amino acid sequence selected from the group consisting of SEQ ID NOs:2, 4 and 6.

2. The polypeptide of claim 1 wherein the polypeptide comprises SEQ ID NO:2.

3. The polypeptide of claim 1 attached to a mobile support.

4. The polypeptide of claim 3 wherein the polypeptide is attached to the mobile support by a covalent or non-covalent interaction.

5. The polypeptide of claim 4 wherein the polypeptide is attached by a linkage selected from the group consisting of a $CO^{2+}$-hexahistidine linkage, a $Ni^{2+}$-hexahistidine linkage a biotin binding protein/biotin linkage, a glutathione S-transferase/glutathione linkage, a monoclonal antibody/antigen linkage, a maltose binding protein/maltose linkage and pluronic linkage.

6. The polypeptide of claim 5 wherein the biotin binding protein is selected from the group consisting of streptavidin and avidin.

7. The polypeptide of claim 3 wherein the mobile support is selected from the group consisting of a bead, optical fiber and glass surface.

8. The polypeptide of claim 7 wherein the bead is a nickel-agarose bead or a magnetic porous glass Streptavidin bead.

* * * * *

SEQUENCE LISTING

<160> NUMBER OF SEQ ID NOS: 31

<210> SEQ ID NO 1
<211> LENGTH: 1247
<212> TYPE: DNA
<213> ORGANISM: Bacillus stearothermophilus

<400> SEQUENCE: 1

```
gttatgaaca tgagtttgag cattccgcat ggcggcacat tgatcaaccg ttggaatccg      60
gattacccaa tcgatgaagc aacgaaaacg atcgagctgt ccaaagccga actaagcgac     120
cttgagctga tcggcacagg cgcctacagc ccgctcaccg ggttttaac gaaagccgat     180 tacgatgcgg tcgtagaaac gatgcgcctc gctgatggca ctgtctggag cattccgatc     240 acgctggcg tgacggaaga aaaagcgagt gaactcactg tcggcgacaa agcgaaactc     300
gtttatggcg gcgacgtcta cggcgtcatt gaaatcgccg atatttaccg cccggataaa     360
acgaaagaag ccaagctcgt ctataaaacc gatgaactcg ctcacccggg cgtgcgcaag     420
ctgtttgaaa aaccagatgt gtacgtcggc ggagcggtta cgctcgtcaa acggaccgac     480
aaaggccagt ttgctccgtt ttatttcgat ccggccgaaa cgcggaaacg atttgccgaa     540
ctcggctgga ataccgtcgt cggcttccaa acacgcaacc cggttcaccg cgcccatgaa     600
tacattcaaa aatgcgcgct tgaaatcgtg gacggcttgt tttaaaccc gctcgtcggc     660 gaaacgaaag cggacgatat tccggccgac atccggatgg aaagctatca agtgctgctg     720
gaaaactatt atccgaaaga ccgcgttttc ttgggcgtct tccaagctgc gatgcgctat     780
gccggtccgc gcgaagcgat tttccatgcc atggtgcgga aaaacttcgg ctgcacgcac     840
ttcatcgtcg gccgcgacca tgcgggcgtc ggcaactatt acggcacgta tgatgcgcaa     900 aaatcttct cgaactttac agccgaagag cttggcatta caccgctctt tttcgaacac     960
agctttattt gcacgaaatg cgaaggcatg gcatcgacga aaacatgccc gcacgacgca    1020
```

-continued

```
caatatcacg ttgtcctttc tggcacgaaa gtccgtgaaa tgttgcgtaa cggccaagtg   1080
ccgccgagca cattcagccg tccggaagtg gccgccgttt tgatcaaagg gctgcaagaa   1140
cgcgaaacgg tcaccccgtc gacacgctaa aggaggagcg agatgagcac gaatatcgtt   1200
tggcatcata catcggtgac aaaagaagat cgccgccaac gcaacgg                 1247
```

<210> SEQ ID NO 2
<211> LENGTH: 386
<212> TYPE: PRT
<213> ORGANISM: Bacillus stearothermophilus

<400> SEQUENCE: 2

```
Met Ser Leu Ser Ile Pro His Gly Gly Thr Leu Ile Asn Arg Trp Asn
  1               5                  10                  15

Pro Asp Tyr Pro Ile Asp Glu Ala Thr Lys Thr Ile Glu Leu Ser Lys
                 20                  25                  30

Ala Glu Leu Ser Asp Leu Glu Leu Ile Gly Thr Gly Ala Tyr Ser Pro
             35                  40                  45

Leu Thr Gly Phe Leu Thr Lys Ala Asp Tyr Asp Ala Val Val Glu Thr
         50                  55                  60

Met Arg Leu Ala Asp Gly Thr Val Trp Ser Ile Pro Ile Thr Leu Ala
 65                  70                  75                  80

Val Thr Glu Glu Lys Ala Ser Glu Leu Thr Val Gly Asp Lys Ala Lys
                 85                  90                  95

Leu Val Tyr Gly Gly Asp Val Tyr Gly Val Ile Glu Ile Ala Asp Ile
                100                 105                 110

Tyr Arg Pro Asp Lys Thr Lys Glu Ala Lys Leu Val Tyr Lys Thr Asp
            115                 120                 125

Glu Leu Ala His Pro Gly Val Arg Lys Leu Phe Glu Lys Pro Asp Val
        130                 135                 140

Tyr Val Gly Gly Ala Val Thr Leu Val Lys Arg Thr Asp Lys Gly Gln
145                 150                 155                 160

Phe Ala Pro Phe Tyr Phe Asp Pro Ala Glu Thr Arg Lys Arg Phe Ala
                165                 170                 175

Glu Leu Gly Trp Asn Thr Val Val Gly Phe Gln Thr Arg Asn Pro Val
            180                 185                 190

His Arg Ala His Glu Tyr Ile Gln Lys Cys Ala Leu Glu Ile Val Asp
        195                 200                 205

Gly Leu Phe Leu Asn Pro Leu Val Gly Glu Thr Lys Ala Asp Asp Ile
    210                 215                 220

Pro Ala Asp Ile Arg Met Glu Ser Tyr Gln Val Leu Leu Glu Asn Tyr
225                 230                 235                 240

Tyr Pro Lys Asp Arg Val Phe Leu Gly Val Phe Gln Ala Ala Met Arg
                245                 250                 255

Tyr Ala Gly Pro Arg Glu Ala Ile Phe His Ala Met Val Arg Lys Asn
            260                 265                 270

Phe Gly Cys Thr His Phe Ile Val Gly Arg Asp His Ala Gly Val Gly
        275                 280                 285

Asn Tyr Tyr Gly Thr Tyr Asp Ala Gln Lys Ile Phe Ser Asn Phe Thr
    290                 295                 300

Ala Glu Glu Leu Gly Ile Thr Pro Leu Phe Phe Glu His Ser Phe Tyr
305                 310                 315                 320

Cys Thr Lys Cys Glu Gly Met Ala Ser Thr Lys Thr Cys Pro His Asp
                325                 330                 335
```

```
Ala Gln Tyr His Val Val Leu Ser Gly Thr Lys Val Arg Glu Met Leu
                340                 345                 350
Arg Asn Gly Gln Val Pro Pro Ser Thr Phe Ser Arg Pro Glu Val Ala
            355                 360                 365
Ala Val Leu Ile Lys Gly Leu Gln Glu Arg Glu Thr Val Thr Pro Ser
        370                 375                 380
Thr Arg
385

<210> SEQ ID NO 3
<211> LENGTH: 3519
<212> TYPE: DNA
<213> ORGANISM: Escherichia coli

<400> SEQUENCE: 3
```

| | | | | | |
|---|---|---|---|---|---|
| atgcggggtt | ctcatcatca | tcatcatcat | ggtatggcta | gcatggaagc | gccagcagca | 60 |
| gcggaaatca | gtggtcacat | cgtacgttcc | ccgatggttg | gtactttcta | ccgcacccca | 120 |
| agcccggacg | caaaagcgtt | catcgaagtg | ggtcagaaag | tcaacgtggg | cgataccctg | 180 |
| tgcatcgttg | aagccatgaa | atgatgaac | cagatcgaag | cggacaaatc | cggtaccgtg | 240 |
| aaagcaattc | tggtcgaaag | tggacaaccg | gtagaatttg | acgagccgct | ggtcgtcatc | 300 |
| gagggatccg | agctcgagat | ccaaatggaa | gacgccaaaa | acataaagaa | aggcccggcg | 360 |
| ccattctatc | ctctagagga | tggaaccgct | ggagagcaac | tgcataaggc | tatgaagaga | 420 |
| tacgccctgg | ttcctggaac | aattgctttt | acagatgcac | atatcgaggt | gaacatcacg | 480 |
| tacgcggaat | acttcgaaat | gtccgttcgg | ttggcagaag | ctatgaaacg | atatgggctg | 540 |
| aatacaaatc | acagaatcgt | cgtatgcagt | gaaaactctc | ttcaattctt | tatgccggtg | 600 |
| ttgggcgcgt | tatttatcgg | agttgcagtt | gcgcccgcga | acgacattta | taatgaacgt | 660 |
| gaattgctca | acagtatgaa | catttcgcag | cctaccgtag | tgtttgtttc | caaaaagggg | 720 |
| ttgcaaaaaa | ttttgaacgt | gcaaaaaaaa | ttaccaataa | tccagaaaat | tattatcatg | 780 |
| gattctaaaa | cggattacca | gggatttcag | tcgatgtaca | cgttcgtcac | atctcatcta | 840 |
| cctcccggtt | ttaatgaata | cgattttgta | ccagagtcct | ttgatcgtga | caaaacaatt | 900 |
| gcactgataa | tgaattcctc | tggatctact | gggttaccta | agggtgtggc | ccttccgcat | 960 |
| agaactgcct | gcgtcagatt | ctcgcatgcc | agagatccta | ttttggcaa | tcaaatcatt | 1020 |
| ccggatactg | cgattttaag | tgttgttcca | ttccatcacg | gttttggaat | gtttactaca | 1080 |
| ctcggatatt | tgatatgtgg | atttcgagtc | gtcttaatgt | atagatttga | agaagagctg | 1140 |
| tttttacgat | cccttcagga | ttacaaaatt | caaagtgcgt | tgctagtacc | aaccctattt | 1200 |
| tcattcttcg | ccaaaagcac | tctgattgac | aaatacgatt | tatctaattt | acacgaaatt | 1260 |
| gcttctgggg | gcgcacctct | ttcgaaagaa | gtcggggaag | cggttgcaaa | acgcttccat | 1320 |
| cttccaggga | tacgacaagg | atatgggctc | actgagacta | catcagctat | tctgattaca | 1380 |
| cccgaggggg | atgataaacc | gggcgcggtc | ggtaaagttg | ttccattttt | tgaagcgaag | 1440 |
| gttgtggatc | tggataccgg | gaaaacgctg | ggcgttaatc | agagaggcga | attatgtgtc | 1500 |
| agaggaccta | tgattatgtc | cggttatgta | acaatccgg | aagcgaccaa | cgccttgatt | 1560 |
| gacaaggatg | gatggctaca | ttctggagac | atagcttact | gggacgaaga | cgaacacttc | 1620 |
| ttcatagttg | accgcttgaa | gtctttaatt | aaatacaaag | gatatcaggt | ggccccgct | 1680 |
| gaattggaat | cgatattgtt | acaacacccc | aacatcttcg | acgcgggcgt | ggcaggtctt | 1740 |

-continued

```
cccgacgatg acgccggtga acttcccgcc gccgttgttg ttttggagca cggaaagacg    1800
atgacggaaa aagagatcgt ggattacgtc gccagtcaag taacaaccgc gaaaaagttg    1860
cgcggaggag ttgtgtttgt ggacgaagta ccgaaaggtc ttaccggaaa actcgacgca    1920
agaaaaatca gagagatcct cataaaggcc aagaagggcg aaagtccaa attggcggcc     1980
gctatgcctg ctcctcacgg tggtattcta caagacttga ttgctagaga tgcgttaaag    2040
aagaatgaat tgttatctga agcgcaatct tcggacattt tagtatggaa cttgactcct    2100
agacaactat gtgatattga attgattcta aatggtgggt tttctcctct gactgggttt    2160
ttgaacgaaa acgattactc ctctgttgtt acagattcga gattagcaga cggcacattg    2220
tggaccatcc ctattacatt agatgttgat gaagcatttg ctaaccaaat taaaccagac    2280
acaagaattg cccttttcca agatgatgaa attcctattg ctatacttac tgtccaggat    2340
gtttacaagc caaacaaaac tatcgaagcc gaaaaagtct tcagaggtga cccagaacat    2400
ccagccatta gctatttatt taacgttgcc ggtgattatt acgtcggcgg ttctttagaa    2460
gcgattcaat tacctcaaca ttatgactat ccaggtttgc gtaagacacc tgcccaacta    2520
agacttgaat tccaatcaag acaatgggac cgtgtcgtag ctttccaaac tcgtaatcca    2580
atgcatagag cccacaggga gttgactgtg agagccgcca gagaagctaa tgctaaggtg    2640
ctgatccatc cagttgttgg actaaccaaa ccaggtgata tagaccatca cactcgtgtt    2700
cgtgtctacc aggaaattat taagcgttat cctaatggta ttgctttctt atccctgttg    2760
ccattagcaa tgagaatgag tggtgataga gaagccgtat ggcatgctat tattagaaag    2820
aattatggtg cctcccactt cattgttggt agagaccatg cgggcccagg taagaactcc    2880
aagggtgttg atttctacgg tccatacgat gctcaagaat tggtcgaatc ctacaagcat    2940
gaactggaca ttgaagttgt tccattcaga atggtcactt atttgccaga cgaagaccgt    3000
tatgctccaa ttgatcaaat tgacaccaca aagacgagaa ccttgaacat ttcaggtaca    3060
gagttgagac gccgtttaag agttggtggt gagattcctg aatggttctc atatcctgaa    3120
gtggttaaaa tcctaagaga atccaaccca ccaagaccaa acaaggtttt tcaattgtt    3180
ttaggtaatt cattaaccgt ttctcgtgag caattatcca ttgctttgtt gtcaacattc    3240
ttgcaattcg gtggtggcag gtattacaag atctttgaac acaataataa gacagagtta    3300
ctatctttga ttcaagattt cattggttct ggtagtggac taattattcc aaatcaatgg    3360
gaagatgaca aggactctgt tgttggcaag caaaacgttt acttattaga tacctcaagc    3420
tcagccgata ttcagctaga gtcagcggat gaacctattt cacatattgt acaaaaagtt    3480
gtcctattct tggaagacaa tggctttttt gtattttaa                           3519
```

<210> SEQ ID NO 4
<211> LENGTH: 1172
<212> TYPE: PRT
<213> ORGANISM: Escherichia coli

<400> SEQUENCE: 4

Met Arg Gly Ser His His His His His His Gly Met Ala Ser Met Glu
1               5                   10                  15

Ala Pro Ala Ala Ala Glu Ile Ser Gly His Ile Val Arg Ser Pro Met
            20                  25                  30

Val Gly Thr Phe Tyr Arg Thr Pro Ser Pro Asp Ala Lys Ala Phe Ile
        35                  40                  45

Glu Val Gly Gln Lys Val Asn Val Gly Asp Thr Leu Cys Ile Val Glu
    50                  55                  60

-continued

```
Ala Met Lys Met Met Asn Gln Ile Glu Ala Asp Lys Ser Gly Thr Val
 65                  70                  75                  80

Lys Ala Ile Leu Val Glu Ser Gly Gln Pro Val Glu Phe Asp Glu Pro
                 85                  90                  95

Leu Val Val Ile Glu Gly Ser Glu Leu Glu Ile Gln Met Glu Asp Ala
                100                 105                 110

Lys Asn Ile Lys Lys Gly Pro Ala Pro Phe Tyr Pro Leu Glu Asp Gly
                115                 120                 125

Thr Ala Gly Glu Gln Leu His Lys Ala Met Lys Arg Tyr Ala Leu Val
130                 135                 140

Pro Gly Thr Ile Ala Phe Thr Asp Ala His Ile Glu Val Asn Ile Thr
145                 150                 155                 160

Tyr Ala Glu Tyr Phe Glu Met Ser Val Arg Leu Ala Glu Ala Met Lys
                165                 170                 175

Arg Tyr Gly Leu Asn Thr Asn His Arg Ile Val Val Cys Ser Glu Asn
                180                 185                 190

Ser Leu Gln Phe Phe Met Pro Val Leu Gly Ala Leu Phe Ile Gly Val
                195                 200                 205

Ala Val Ala Pro Ala Asn Asp Ile Tyr Asn Glu Arg Glu Leu Leu Asn
210                 215                 220

Ser Met Asn Ile Ser Gln Pro Thr Val Val Phe Val Ser Lys Lys Gly
225                 230                 235                 240

Leu Gln Lys Ile Leu Asn Val Gln Lys Lys Leu Pro Ile Ile Gln Lys
                245                 250                 255

Ile Ile Ile Met Asp Ser Lys Thr Asp Tyr Gln Gly Phe Gln Ser Met
                260                 265                 270

Tyr Thr Phe Val Thr Ser His Leu Pro Pro Gly Phe Asn Glu Tyr Asp
                275                 280                 285

Phe Val Pro Glu Ser Phe Asp Arg Asp Lys Thr Ile Ala Leu Ile Met
                290                 295                 300

Asn Ser Ser Gly Ser Thr Gly Leu Pro Lys Gly Val Ala Leu Pro His
305                 310                 315                 320

Arg Thr Ala Cys Val Arg Phe Ser His Ala Arg Asp Pro Ile Phe Gly
                325                 330                 335

Asn Gln Ile Ile Pro Asp Thr Ala Ile Leu Ser Val Val Pro Phe His
                340                 345                 350

His Gly Phe Gly Met Phe Thr Thr Leu Gly Tyr Leu Ile Cys Gly Phe
                355                 360                 365

Arg Val Val Leu Met Tyr Arg Phe Glu Glu Glu Leu Phe Leu Arg Ser
370                 375                 380

Leu Gln Asp Tyr Lys Ile Gln Ser Ala Leu Leu Val Pro Thr Leu Phe
385                 390                 395                 400

Ser Phe Phe Ala Lys Ser Thr Leu Ile Asp Lys Tyr Asp Leu Ser Asn
                405                 410                 415

Leu His Glu Ile Ala Ser Gly Gly Ala Pro Leu Ser Lys Glu Val Gly
                420                 425                 430

Glu Ala Val Ala Lys Arg Phe His Leu Pro Gly Ile Arg Gln Gly Tyr
                435                 440                 445

Gly Leu Thr Glu Thr Thr Ser Ala Ile Leu Ile Thr Pro Glu Gly Asp
                450                 455                 460

Asp Lys Pro Gly Ala Val Gly Lys Val Val Pro Phe Phe Glu Ala Lys
465                 470                 475                 480
```

```
Val Val Asp Leu Asp Thr Gly Lys Thr Leu Gly Val Asn Gln Arg Gly
            485                 490                 495

Glu Leu Cys Val Arg Gly Pro Met Ile Met Ser Gly Tyr Val Asn Asn
            500                 505                 510

Pro Glu Ala Thr Asn Ala Leu Ile Asp Lys Asp Gly Trp Leu His Ser
            515                 520                 525

Gly Asp Ile Ala Tyr Trp Asp Glu Asp Glu His Phe Phe Ile Val Asp
            530                 535                 540

Arg Leu Lys Ser Leu Ile Lys Tyr Lys Gly Tyr Gln Val Ala Pro Ala
545                 550                 555                 560

Glu Leu Glu Ser Ile Leu Leu Gln His Pro Asn Ile Phe Asp Ala Gly
            565                 570                 575

Val Ala Gly Leu Pro Asp Asp Ala Gly Glu Leu Pro Ala Ala Val
            580                 585                 590

Val Val Leu Glu His Gly Lys Thr Met Thr Glu Lys Glu Ile Val Asp
            595                 600                 605

Tyr Val Ala Ser Gln Val Thr Thr Ala Lys Lys Leu Arg Gly Gly Val
            610                 615                 620

Val Phe Val Asp Glu Val Pro Lys Gly Leu Thr Gly Lys Leu Asp Ala
625                 630                 635                 640

Arg Lys Ile Arg Glu Ile Leu Ile Lys Ala Lys Gly Gly Lys Ser
            645                 650                 655

Lys Leu Ala Ala Ala Met Pro Ala Pro His Gly Gly Ile Leu Gln Asp
            660                 665                 670

Leu Ile Ala Arg Asp Ala Leu Lys Lys Asn Glu Leu Leu Ser Glu Ala
            675                 680                 685

Gln Ser Ser Asp Ile Leu Val Trp Asn Leu Thr Pro Arg Gln Leu Cys
            690                 695                 700

Asp Ile Glu Leu Ile Leu Asn Gly Gly Phe Ser Pro Leu Thr Gly Phe
705                 710                 715                 720

Leu Asn Glu Asn Asp Tyr Ser Ser Val Val Thr Asp Ser Arg Leu Ala
            725                 730                 735

Asp Gly Thr Leu Trp Thr Ile Pro Ile Thr Leu Asp Val Asp Glu Ala
            740                 745                 750

Phe Ala Asn Gln Ile Lys Pro Asp Thr Arg Ile Ala Leu Phe Gln Asp
            755                 760                 765

Asp Glu Ile Pro Ile Ala Ile Leu Thr Val Gln Asp Val Tyr Lys Pro
770                 775                 780

Asn Lys Thr Ile Glu Ala Glu Lys Val Phe Arg Gly Asp Pro Glu His
785                 790                 795                 800

Pro Ala Ile Ser Tyr Leu Phe Asn Val Ala Gly Asp Tyr Tyr Val Gly
            805                 810                 815

Gly Ser Leu Glu Ala Ile Gln Leu Pro Gln His Tyr Asp Tyr Pro Gly
            820                 825                 830

Leu Arg Lys Thr Pro Ala Gln Leu Arg Leu Glu Phe Gln Ser Arg Gln
            835                 840                 845

Trp Asp Arg Val Val Ala Phe Gln Thr Arg Asn Pro Met His Arg Ala
            850                 855                 860

His Arg Glu Leu Thr Val Arg Ala Ala Arg Glu Ala Asn Ala Lys Val
865                 870                 875                 880

Leu Ile His Pro Val Val Gly Leu Thr Lys Pro Gly Asp Ile Asp His
            885                 890                 895

His Thr Arg Val Arg Val Tyr Gln Glu Ile Ile Lys Arg Tyr Pro Asn
```

-continued

```
              900              905              910
Gly Ile Ala Phe Leu Ser Leu Leu Pro Leu Ala Met Arg Met Ser Gly
         915              920              925

Asp Arg Glu Ala Val Trp His Ala Ile Ile Arg Lys Asn Tyr Gly Ala
     930              935              940

Ser His Phe Ile Val Gly Arg Asp His Ala Gly Pro Gly Lys Asn Ser
945              950              955              960

Lys Gly Val Asp Phe Gly Pro Tyr Asp Ala Gln Glu Leu Val Glu
             965              970              975

Ser Tyr Lys His Glu Leu Asp Ile Glu Val Val Pro Phe Arg Met Val
         980              985              990

Thr Tyr Leu Pro Asp Glu Asp Arg Tyr Ala Pro Ile Asp Gln Ile Asp
     995              1000             1005

Thr Thr Lys Thr Arg Thr Leu Asn Ile Ser Gly Thr Glu Leu Arg Arg
    1010             1015             1020

Arg Leu Arg Val Gly Gly Glu Ile Pro Glu Trp Phe Ser Tyr Pro Glu
1025             1030             1035             1040

Val Val Lys Ile Leu Arg Glu Ser Asn Pro Pro Arg Pro Lys Gln Gly
             1045             1050             1055

Phe Ser Ile Val Leu Gly Asn Ser Leu Thr Val Ser Arg Glu Gln Leu
         1060             1065             1070

Ser Ile Ala Leu Leu Ser Thr Phe Leu Gln Phe Gly Gly Gly Arg Tyr
     1075             1080             1085

Tyr Lys Ile Phe Glu His Asn Asn Lys Thr Glu Leu Leu Ser Leu Ile
    1090             1095             1100

Gln Asp Phe Ile Gly Ser Gly Ser Gly Leu Ile Ile Pro Asn Gln Trp
1105             1110             1115             1120

Glu Asp Asp Lys Asp Ser Val Val Gly Lys Gln Asn Val Tyr Leu Leu
             1125             1130             1135

Asp Thr Ser Ser Ser Ala Asp Ile Gln Leu Glu Ser Ala Asp Glu Pro
         1140             1145             1150

Ile Ser His Ile Val Gln Lys Val Val Leu Phe Leu Glu Asp Asn Gly
     1155             1160             1165

Phe Phe Val Phe
    1170
```

<210> SEQ ID NO 5
<211> LENGTH: 1488
<212> TYPE: DNA
<213> ORGANISM: Escherichia coli

<400> SEQUENCE: 5

```
atgcggggtt ctcatcatca tcatcatcat ggtatggcta gcatggaagc gccagcagca      60
gcggaaatca gtggtcacat cgtacgttcc ccgatggttg gtactttcta ccgcacccca     120
agcccggacg caaaagcgtt catcgaagtg ggtcagaaag tcaacgtggg cgatacccctg    180 tgcatcgttg aagccatgaa atgatgaac cagatcgaag cggacaaatc cggtaccgtg      240
aaagcaattc tggtcgaaag tggacaaccg gtagaatttg acgagccgct ggtcgtcatc     300
gagggatccg agctcgagat ctgcagcatg agcgtaagca tcccgcatgg cggcacattg     360
atcaaccgtt ggaatccgga ttacccaatc gatgaagcaa cgaaaacgat cgagctgtcc     420
aaagccgaac taagcgacct tgagctgatc ggcacaggcg cctacagccc gctcaccggg     480 ttttttaacga aagccgatta cgatgcggtc gtagaaacga tgcgcctcgc tgatggcact    540
```

-continued

```
gtctggagca ttccgatcac gctggcggtg acggaagaaa aagcgagtga actcactgtc    600
ggcgacaaag cgaaactcgt ttatggcggc gacgtctacg gcgtcattga aatcgccgat    660
atttaccgcc cggataaaac gaaagaagcc aagctcgtct ataaaaccga tgaactcgct    720
cacccgggcg tgcgcaagct gttttgaaaaa ccagatgtgt acgtcggcgg agcggttacg    780
ctcgtcaaac ggaccgacaa aggccagttt gctccgtttt atttcgatcc ggccgaaacg    840
cggaaacgat tgccgaact cggctggaat accgtcgtcg gcttccaaac acgcaacccg    900
gttcaccgcg cccatgaata cattcaaaaa tgcgcgcttg aaatcgtgga cggcttgttt    960
ttaaacccgc tcgtcggcga aacgaaagcg acgatattc cggccgacat ccggatggaa   1020
agctatcaag tgctgctgga aaactattat ccgaaagacc gcgttttctt gggcgtcttc   1080
caagctgcga tgcgctatgc cggtccgcgc gaagcgattt tccatgccat ggtgcggaaa   1140
aacttcggct gcacgcactt catcgtcggc cgcgaccatg cgggcgtcgg caactattac   1200
ggcacgtatg atgcgcaaaa aatcttctcg aactttacag ccgaagagct tggcattaca   1260
ccgctctttt tcgaacacag ctttttattgc acgaaatgcg aaggcatggc atcgacgaaa   1320
acatgcccgc acgacgcaca atatcacgtt gtcctttctg cacgaaagt ccgtgaaatg    1380
ttgcgtaacg gccaagtgcc gccgagcaca ttcagccgtc cggaagtggc cgccgttttg   1440
atcaaagggc tgcaagaacg cgaaacggtc gccccgtcag cgcgctaa              1488
```

<210> SEQ ID NO 6
<211> LENGTH: 495
<212> TYPE: PRT
<213> ORGANISM: Escherichia coli

<400> SEQUENCE: 6

```
Met Arg Gly Ser His His His His His Gly Met Ala Ser Met Glu
  1               5                  10                  15

Ala Pro Ala Ala Glu Ile Ser Gly His Ile Val Arg Ser Pro Met
                 20                  25                  30

Val Gly Thr Phe Tyr Arg Thr Pro Ser Pro Asp Ala Lys Ala Phe Ile
                 35                  40                  45

Glu Val Gly Gln Lys Val Asn Val Gly Asp Thr Leu Cys Ile Val Glu
 50                  55                  60

Ala Met Lys Met Met Asn Gln Ile Glu Ala Asp Lys Ser Gly Thr Val
 65                  70                  75                  80

Lys Ala Ile Leu Val Glu Ser Gly Gln Pro Val Glu Phe Asp Glu Pro
                 85                  90                  95

Leu Val Val Ile Glu Gly Ser Glu Leu Glu Ile Cys Ser Met Ser Val
                100                 105                 110

Ser Ile Pro His Gly Gly Thr Leu Ile Asn Arg Trp Asn Pro Asp Tyr
                115                 120                 125

Pro Ile Asp Glu Ala Thr Lys Thr Ile Glu Leu Ser Lys Ala Glu Leu
                130                 135                 140

Ser Asp Leu Glu Leu Ile Gly Thr Gly Ala Tyr Ser Pro Leu Thr Gly
145                 150                 155                 160

Phe Leu Thr Lys Ala Asp Tyr Asp Ala Val Val Glu Thr Met Arg Leu
                165                 170                 175

Ala Asp Gly Thr Val Trp Ser Ile Pro Ile Thr Leu Ala Val Thr Glu
                180                 185                 190

Glu Lys Ala Ser Glu Leu Thr Val Gly Asp Lys Ala Lys Leu Val Tyr
                195                 200                 205
```

```
Gly Gly Asp Val Tyr Gly Val Ile Glu Ile Ala Asp Ile Tyr Arg Pro
        210                 215                 220

Asp Lys Thr Lys Glu Ala Lys Leu Val Tyr Lys Thr Asp Glu Leu Ala
225                 230                 235                 240

His Pro Gly Val Arg Lys Leu Phe Glu Lys Pro Asp Val Tyr Val Gly
                245                 250                 255

Gly Ala Val Thr Leu Val Lys Arg Thr Asp Lys Gly Gln Phe Ala Pro
                260                 265                 270

Phe Tyr Phe Asp Pro Ala Glu Thr Arg Lys Arg Phe Ala Glu Leu Gly
            275                 280                 285

Trp Asn Thr Val Gly Phe Gln Thr Arg Asn Pro Val His Arg Ala
        290                 295                 300

His Glu Tyr Ile Gln Lys Cys Ala Leu Glu Ile Val Asp Gly Leu Phe
305                 310                 315                 320

Leu Asn Pro Leu Val Gly Glu Thr Lys Ala Asp Ile Pro Ala Asp
            325                 330                 335

Ile Arg Met Glu Ser Tyr Gln Val Leu Leu Glu Asn Tyr Tyr Pro Lys
                340                 345                 350

Asp Arg Val Phe Leu Gly Val Phe Gln Ala Ala Met Arg Tyr Ala Gly
                355                 360                 365

Pro Arg Glu Ala Ile Phe His Ala Met Val Arg Lys Asn Phe Gly Cys
370                 375                 380

Thr His Phe Ile Val Gly Arg Asp His Ala Gly Val Gly Asn Tyr Tyr
385                 390                 395                 400

Gly Thr Tyr Asp Ala Gln Lys Ile Phe Ser Asn Phe Thr Ala Glu Glu
                405                 410                 415

Leu Gly Ile Thr Pro Leu Phe Phe Glu His Ser Phe Tyr Cys Thr Lys
                420                 425                 430

Cys Glu Gly Met Ala Ser Thr Lys Thr Cys Pro His Asp Ala Gln Tyr
            435                 440                 445

His Val Val Leu Ser Gly Thr Lys Val Arg Glu Met Leu Arg Asn Gly
450                 455                 460

Gln Val Pro Pro Ser Thr Phe Ser Arg Pro Glu Val Ala Ala Val Leu
465                 470                 475                 480

Ile Lys Gly Leu Gln Glu Arg Glu Thr Val Ala Pro Ser Ala Arg
            485                 490                 495

<210> SEQ ID NO 7
<211> LENGTH: 45
<212> TYPE: DNA
<213> ORGANISM: Artificial Sequence
<220> FEATURE:
<223> OTHER INFORMATION: Description of Artificial Sequence: primer

<400> SEQUENCE: 7
cccttctgca gcatgagcgt aagcatcccg catggcggca cattg            45

<210> SEQ ID NO 8
<211> LENGTH: 47
<212> TYPE: DNA
<213> ORGANISM: Artificial Sequence
<220> FEATURE:
<223> OTHER INFORMATION: Description of Artificial Sequence: primer

<400> SEQUENCE: 8
cccgtaagct tttagcgcgc tgacggggcg accgtttcgc gttcttg           47
```

<210> SEQ ID NO 9
<211> LENGTH: 48
<212> TYPE: DNA
<213> ORGANISM: Artificial Sequence
<220> FEATURE:
<223> OTHER INFORMATION: Description of Artificial Sequence: primer

<400> SEQUENCE: 9
ccccctcgag atccaaatgg aagacgccaa aaacataaag aaaggccc           48

<210> SEQ ID NO 10
<211> LENGTH: 45
<212> TYPE: DNA
<213> ORGANISM: Artificial Sequence
<220> FEATURE:
<223> OTHER INFORMATION: Description of Artificial Sequence: primer

<400> SEQUENCE: 10
ccccctcgag atccaaatgg ctgacaaaaa catcctgtat ggccc              45

<210> SEQ ID NO 11
<211> LENGTH: 67
<212> TYPE: DNA
<213> ORGANISM: Artificial Sequence
<220> FEATURE:
<223> OTHER INFORMATION: Description of Artificial Sequence: primer

<400> SEQUENCE: 11
ttgtagaata ccaccgtgag gagcaggcat agcggccgcc aatttggact ttccgccctt    60
cttggcc                                                       67

<210> SEQ ID NO 12
<211> LENGTH: 64
<212> TYPE: DNA
<213> ORGANISM: Artificial Sequence
<220> FEATURE:
<223> OTHER INFORMATION: Description of Artificial Sequence: primer

<400> SEQUENCE: 12
ttgtagaata ccaccgtgag gagcaggcat agcggccgca ccgttggtgt gtttctcgaa    60
catc                                                          64

<210> SEQ ID NO 13
<211> LENGTH: 37
<212> TYPE: DNA
<213> ORGANISM: Artificial Sequence
<220> FEATURE:
<223> OTHER INFORMATION: Description of Artificial Sequence: primer

<400> SEQUENCE: 13
gcggccgcta tgcctgctcc tcacggtggt attctac                      37

<210> SEQ ID NO 14
<211> LENGTH: 49
<212> TYPE: DNA
<213> ORGANISM: Artificial Sequence
<220> FEATURE:
<223> OTHER INFORMATION: Description of Artificial Sequence: primer

<400> SEQUENCE: 14
ccccaagctt ttaaaataca aaaagccat tgtcttccaa gaataggac           49

<210> SEQ ID NO 15
<211> LENGTH: 49
<212> TYPE: DNA

```
<213> ORGANISM: Artificial Sequence
<220> FEATURE:
<223> OTHER INFORMATION: Description of Artificial Sequence: primer

<400> SEQUENCE: 15
ccccggatcc atccaaatgc ctgctcctca cggtggtatt ctacaagac            49

<210> SEQ ID NO 16
<211> LENGTH: 62
<212> TYPE: DNA
<213> ORGANISM: Artificial Sequence
<220> FEATURE:
<223> OTHER INFORMATION: Description of Artificial Sequence: primer

<400> SEQUENCE: 16
gggcctttct ttatgttttt ggcgtcttcc atagcggccg caaatacaaa aaagccattg    60
tc                                                                  62

<210> SEQ ID NO 17
<211> LENGTH: 41
<212> TYPE: DNA
<213> ORGANISM: Artificial Sequence
<220> FEATURE:
<223> OTHER INFORMATION: Description of Artificial Sequence: primer

<400> SEQUENCE: 17
gcggccgcta tggaagacgc caaaaacata agaaaggcc c                    41

<210> SEQ ID NO 18
<211> LENGTH: 41
<212> TYPE: DNA
<213> ORGANISM: Artificial Sequence
<220> FEATURE:
<223> OTHER INFORMATION: Description of Artificial Sequence: primer

<400> SEQUENCE: 18 cccccccatgg ttacaatttg gactttccgc ccttcttggc c                  41

<210> SEQ ID NO 19
<211> LENGTH: 59
<212> TYPE: DNA
<213> ORGANISM: Artificial Sequence
<220> FEATURE:
<223> OTHER INFORMATION: Description of Artificial Sequence: primer

<400> SEQUENCE: 19
gggccataca ggatgttttt gtcagccata gcggccgcaa atacaaaaaa gccattgtc   59

<210> SEQ ID NO 20
<211> LENGTH: 38
<212> TYPE: DNA
<213> ORGANISM: Artificial Sequence
<220> FEATURE:
<223> OTHER INFORMATION: Description of Artificial Sequence: primer

<400> SEQUENCE: 20
gcggccgcta tggctgacaa aaacatcctg tatggccc                       38

<210> SEQ ID NO 21
<211> LENGTH: 44
<212> TYPE: DNA
<213> ORGANISM: Artificial Sequence
<220> FEATURE:
<223> OTHER INFORMATION: Description of Artificial Sequence: primer

<400> SEQUENCE: 21
```
ccccaagctt ctaaccgttg gtgtgtttct cgaacatctg acgc          44

<210> SEQ ID NO 22
<211> LENGTH: 386
<212> TYPE: PRT
<213> ORGANISM: Bacillus stearothermophilus

<400> SEQUENCE: 22

Met Ser Val Ser Ile Pro His Gly Gly Thr Leu Ile Asn Arg Trp Asn
1               5                   10                  15

Pro Asp Tyr Pro Leu Asp Glu Ala Thr Lys Thr Ile Glu Leu Ser Lys
            20                  25                  30

Ala Glu Leu Ser Asp Leu Glu Leu Ile Gly Thr Gly Ala Tyr Ser Pro
        35                  40                  45

Leu Thr Gly Phe Leu Thr Lys Thr Asp Tyr Asp Ala Val Val Glu Thr
    50                  55                  60

Met Arg Leu Ser Asp Gly Thr Val Trp Ser Ile Pro Val Thr Leu Ala
65                  70                  75                  80

Val Thr Glu Glu Lys Ala Lys Glu Leu Ala Val Gly Asp Lys Ala Lys
                85                  90                  95

Leu Val Tyr Arg Gly Asp Val Tyr Gly Val Ile Glu Ile Ala Asp Ile
            100                 105                 110

Tyr Arg Pro Asp Lys Thr Lys Glu Ala Lys Leu Val Tyr Lys Thr Asp
        115                 120                 125

Glu Leu Ala His Pro Gly Val Arg Lys Leu Phe Glu Lys Pro Asp Val
    130                 135                 140

Tyr Val Gly Gly Glu Ile Thr Leu Val Lys Arg Thr Asp Lys Gly Gln
145                 150                 155                 160

Phe Ala Ala Phe Tyr Phe Asp Pro Ala Glu Thr Arg Lys Lys Phe Ala
                165                 170                 175

Glu Phe Gly Trp Asn Thr Val Val Gly Phe Gln Thr Arg Asn Pro Val
            180                 185                 190

His Arg Ala His Glu Tyr Ile Gln Lys Cys Ala Leu Glu Ile Val Asp
        195                 200                 205

Gly Leu Phe Leu Asn Pro Leu Val Gly Glu Thr Lys Ser Asp Asp Ile
    210                 215                 220

Pro Ala Asp Ile Arg Met Glu Ser Tyr Gln Val Leu Leu Glu Asn Tyr
225                 230                 235                 240

Tyr Pro Lys Asp Arg Val Phe Leu Gly Val Phe Gln Ala Ala Met Arg
                245                 250                 255

Tyr Ala Gly Pro Arg Glu Ala Ile Phe His Ala Met Val Arg Lys Asn
            260                 265                 270

Phe Gly Cys Thr His Phe Ile Val Gly Arg Asp His Ala Gly Val Gly
        275                 280                 285

Asn Tyr Tyr Gly Thr Tyr Asp Ala Gln Lys Ile Phe Leu Asn Phe Thr
    290                 295                 300

Ala Glu Glu Leu Gly Ile Thr Pro Leu Phe Phe Glu His Ser Phe Tyr
305                 310                 315                 320

Cys Thr Lys Cys Glu Gly Met Ala Ser Thr Lys Thr Cys Pro His Asp
                325                 330                 335

Ala Lys Tyr His Val Val Leu Ser Gly Thr Lys Val Arg Glu Met Leu
            340                 345                 350

Arg Asn Gly Gln Val Pro Pro Ser Thr Phe Ser Arg Pro Glu Val Ala
        355                 360                 365

-continued

```
Ala Val Leu Ile Lys Gly Leu Gln Glu Arg Glu Thr Val Ala Pro Ser
    370                 375                 380

Ala Arg
385

<210> SEQ ID NO 23
<211> LENGTH: 546
<212> TYPE: PRT
<213> ORGANISM: Aquifex aeolicus

<400> SEQUENCE: 23

Met Glu Lys Ile Lys Tyr Leu Lys Ser Ile Gln Ile Ser Gln Arg Ser
  1               5                  10                  15

Val Leu Asp Leu Lys Leu Leu Ala Val Gly Ala Phe Thr Pro Leu Asp
             20                  25                  30

Arg Phe Met Gly Glu Glu Asp Tyr Arg Asn Val Val Glu Ser Met Arg
         35                  40                  45

Leu Lys Ser Gly Thr Leu Phe Pro Ile Pro Ile Thr Leu Pro Met Glu
     50                  55                  60

Lys Glu Ile Ala Lys Asp Leu Lys Glu Gly Trp Ile Val Leu Arg
 65                  70                  75                  80

Asp Pro Lys Asn Val Pro Leu Ala Ile Met Arg Val Glu Glu Val Tyr
                 85                  90                  95

Lys Trp Asn Leu Glu Tyr Glu Ala Lys Asn Val Leu Gly Thr Thr Asp
            100                 105                 110

Pro Arg His Pro Leu Val Ala Glu Met His Thr Trp Gly Glu Tyr Tyr
        115                 120                 125

Ile Ser Gly Glu Leu Lys Val Ile Gln Leu Pro Lys Tyr Tyr Asp Phe
    130                 135                 140

Pro Glu Tyr Arg Lys Thr Pro Lys Gln Val Arg Glu Glu Ile Lys Ser
145                 150                 155                 160

Leu Gly Leu Asp Lys Ile Val Ala Phe Gln Thr Arg Asn Pro Met His
                165                 170                 175

Arg Val His Glu Glu Leu Thr Lys Arg Ala Met Glu Lys Val Gly Gly
            180                 185                 190

Gly Leu Leu Leu His Pro Val Gly Leu Thr Lys Pro Gly Asp Val
        195                 200                 205

Asp Val Tyr Thr Arg Met Arg Ile Tyr Lys Val Leu Tyr Glu Lys Tyr
    210                 215                 220

Tyr Asp Lys Lys Lys Thr Ile Leu Ala Phe Leu Pro Leu Ala Met Arg
225                 230                 235                 240

Met Ala Gly Pro Arg Glu Ala Leu Trp His Gly Ile Ile Arg Arg Asn
                245                 250                 255

Tyr Gly Ala Thr His Phe Ile Val Gly Arg Asp His Ala Ser Pro Gly
            260                 265                 270

Lys Asp Ser Lys Gly Lys Pro Phe Tyr Asp Pro Tyr Glu Ala Gln Glu
        275                 280                 285

Leu Phe Lys Lys Tyr Glu Asp Glu Ile Gly Ile Lys Met Val Pro Phe
    290                 295                 300

Glu Glu Leu Val Tyr Val Pro Glu Leu Asp Gln Tyr Val Glu Ile Asn
305                 310                 315                 320

Glu Ala Lys Lys Arg Asn Leu Lys Tyr Ile Asn Ile Ser Gly Thr Glu
                325                 330                 335

Ile Arg Glu Asn Phe Leu Lys Gln Gly Arg Lys Leu Pro Glu Trp Phe
```

```
            340                 345                 350
Thr Arg Pro Glu Val Ala Glu Ile Leu Ala Thr Tyr Val Pro Lys
        355                 360                 365
His Lys Gln Gly Phe Cys Val Trp Leu Thr Gly Leu Pro Cys Ala Gly
        370                 375                 380
Lys Ser Thr Ile Ala Glu Ile Leu Ala Thr Met Leu Gln Ala Arg Gly
385                 390                 395                 400
Arg Lys Val Thr Leu Leu Asp Gly Asp Val Arg Thr His Leu Ser
                405                 410                 415
Arg Gly Leu Gly Phe Ser Lys Asp Arg Ile Thr Asn Ile Leu Arg
            420                 425                 430
Val Gly Phe Val Ala Ser Glu Ile Val Lys His Asn Gly Val Val Ile
            435                 440                 445
Cys Ala Leu Val Ser Pro Tyr Arg Ser Ala Arg Asn Gln Val Arg Asn
            450                 455                 460
Met Met Glu Glu Gly Lys Phe Ile Glu Val Phe Val Asp Ala Pro Val
465                 470                 475                 480
Glu Val Cys Glu Glu Arg Asp Val Lys Gly Leu Tyr Lys Lys Ala Lys
                485                 490                 495
Glu Gly Leu Ile Lys Gly Phe Thr Gly Val Asp Asp Pro Tyr Glu Pro
                500                 505                 510
Pro Val Ala Pro Glu Val Arg Val Asp Thr Thr Lys Leu Thr Pro Glu
            515                 520                 525
Glu Ser Ala Leu Lys Ile Leu Glu Phe Leu Lys Lys Glu Gly Phe Ile
            530                 535                 540
Lys Asp
545

<210> SEQ ID NO 24
<211> LENGTH: 259
<212> TYPE: PRT
<213> ORGANISM: Pyrococcus furiosus

<400> SEQUENCE: 24

Met Val Ser Lys Pro His Gly Gly Lys Leu Ile Arg Arg Ile Ala Ala
1               5                   10                  15
Pro Arg Thr Arg Glu Arg Ile Leu Ser Glu Gln His Glu Tyr Pro Arg
            20                  25                  30
Val Gln Ile Asp His Gly Arg Ala Ile Asp Leu Glu Asn Ile Ala His
        35                  40                  45
Gly Val Tyr Ser Pro Leu Lys Gly Phe Leu Thr Arg Glu Asp Phe Glu
    50                  55                  60
Ser Val Leu Asp Tyr Met Arg Leu Ser Asp Asp Thr Pro Trp Thr Ile
65                  70                  75                  80
Pro Ile Val Leu Asp Val Gly Glu Pro Thr Phe Glu Gly Gly Asp Ala
                85                  90                  95
Ile Leu Leu Tyr Tyr Glu Asn Pro Pro Ile Ala Arg Met His Val Glu
            100                 105                 110
Asp Ile Tyr Thr Tyr Asp Lys Lys Glu Phe Ala Val Lys Val Phe Lys
        115                 120                 125
Thr Asp Asp Pro Asn His Leu Gly Val Ala Arg Val Tyr Ser Met Gly
    130                 135                 140
Lys Tyr Leu Val Gly Gly Ile Glu Leu Leu Asn Glu Leu Pro Asn
145                 150                 155                 160
```

```
Pro Phe Ala Lys Tyr Thr Leu Arg Pro Val Glu Thr Arg Ile Leu Phe
                165                 170                 175

Lys Glu Arg Gly Trp Lys Thr Ile Val Ala Phe Gln Thr Arg Asn Val
            180                 185                 190

Pro His Leu Gly His Glu Tyr Val Gln Lys Ala Ala Leu Thr Phe Val
        195                 200                 205

Asp Gly Leu Phe Ile Asn Pro Val Leu Gly Arg Lys Lys Lys Gly Asp
    210                 215                 220

Tyr Lys Asp Glu Val Ile Ile Lys Ala Tyr Tyr Leu Ile Met Lys Tyr
225                 230                 235                 240

Cys Ser Asn Thr Thr His His Ala Ile Met Arg Lys Thr Ser Thr Ser
                245                 250                 255

Ser Gln Thr

<210> SEQ ID NO 25
<211> LENGTH: 406
<212> TYPE: PRT
<213> ORGANISM: Sulfolobus solfataricus

<400> SEQUENCE: 25

Met Asn Leu Ile Gly His Gly Lys Val Glu Ile Val Glu Arg Ile Lys
  1               5                  10                  15

Thr Ile Ser Asp Phe Lys Glu Leu His Arg Ile Glu Val Lys Arg Gln
             20                  25                  30

Leu Ala His Glu Ile Val Ser Ile Ala Tyr Gly Phe Leu Ser Pro Leu
         35                  40                  45

Lys Gly Phe Met Asn Tyr Glu Glu Val Asp Gly Val Val Glu Asn Met
     50                  55                  60

Arg Leu Pro Asn Gly Val Leu Trp Pro Ile Pro Leu Val Phe Asp Tyr
 65                  70                  75                  80

Ser Gln Asn Glu Lys Val Lys Glu Gly Asp Thr Ile Gly Ile Thr Tyr
                 85                  90                  95

Leu Gly Lys Pro Leu Ala Ile Met Lys Val Lys Glu Ile Phe Lys Tyr
            100                 105                 110

Asp Lys Leu Lys Ile Ala Glu Lys Val Tyr Lys Thr Lys Asp Ile Lys
        115                 120                 125

His Pro Gly Val Lys Arg Thr Leu Ser Tyr Ala Asp Ala Phe Leu Ala
    130                 135                 140

Gly Asp Val Trp Leu Val Arg Glu Pro Gln Phe Asn Lys Pro Tyr Ser
145                 150                 155                 160

Glu Phe Trp Leu Thr Pro Arg Met His Arg Thr Val Phe Glu Lys Lys
                165                 170                 175

Gly Trp Lys Arg Val Val Ala Phe Gln Thr Arg Asn Val Pro His Thr
            180                 185                 190

Gly His Glu Tyr Leu Met Lys Phe Ala Trp Phe Ala Ala Asn Glu Asn
        195                 200                 205

Gln Lys Val Asp Glu Pro Arg Thr Gly Ile Leu Val Asn Val Val Ile
    210                 215                 220

Gly Glu Lys Arg Val Gly Asp Tyr Ile Asp Glu Ala Ile Leu Leu Thr
225                 230                 235                 240

His Asp Ala Leu Ser Lys Tyr Gly Tyr Ile Ser Pro Lys Val His Leu
                245                 250                 255

Leu Ser Phe Thr Leu Trp Asp Met Arg Tyr Ala Gly Pro Arg Glu Ala
            260                 265                 270
```

Leu Leu His Ala Ile Ile Arg Ser Asn Leu Gly Cys Thr His His Val
            275                 280                 285

Phe Gly Arg Asp His Ala Gly Val Gly Asn Tyr Tyr Ser Pro Tyr Glu
            290                 295                 300

Ala His Glu Ile Phe Asp Ser Ile Asn Glu Asp Leu Leu Ile Lys
305                 310                 315                 320

Pro Ile Phe Leu Arg Glu Asn Tyr Tyr Cys Pro Arg Cys Gly Ser Ile
            325                 330                 335

Glu Asn Glu Ile Leu Cys Asp His Lys Asp Glu Lys Gln Glu Phe Ser
            340                 345                 350

Gly Ser Leu Ile Arg Ser Ile Leu Asp Glu Val Lys Pro Thr Lys
            355                 360                 365

Met Val Met Arg Pro Glu Val Tyr Asp Val Leu Met Lys Ala Ala Glu
            370                 375                 380

Gln Tyr Gly Phe Gly Ser Pro Phe Val Thr Glu Glu Tyr Leu Glu Lys
385                 390                 395                 400

Arg Gln Ser Ile Leu Gly
            405

<210> SEQ ID NO 26
<211> LENGTH: 455
<212> TYPE: PRT
<213> ORGANISM: Pyrobaculum aerophilum

<400> SEQUENCE: 26

Met Pro Met Pro Ala Pro Leu Glu Pro His Gly Gly Arg Leu Val Tyr
1               5                   10                  15

Asn Val Ile Glu Asp Arg Asp Lys Ala Ala Met Ile Gln Gly Leu
            20                  25                  30

Pro Ser Ile Glu Ile Glu Pro Thr Leu Gly Pro Asp Gly Ser Pro Ile
            35                  40                  45

Arg Asn Pro Tyr Arg Glu Ile Met Ser Ile Ala Tyr Gly Phe Phe Ser
        50                  55                  60

Pro Val Glu Gly Phe Met Thr Arg Asn Glu Val Glu Ser Ile Leu Lys
65                  70                  75                  80

Glu Arg Arg Leu Leu Asn Gly Trp Leu Phe Pro Phe Pro Leu Ile Tyr
                85                  90                  95

Asp Val Asp Glu Glu Lys Ile Lys Gly Ile Lys Glu Gly Asp Ser Val
            100                 105                 110

Leu Leu Lys Leu Lys Gly Lys Pro Leu Ala Val Leu Asn Val Glu Glu
            115                 120                 125

Ile Trp Arg Leu Pro Asp Arg Lys Glu Leu Ala Asp Ala Val Phe Gly
        130                 135                 140

Thr Pro Glu Arg Asn Lys Glu Val Val Lys Lys Arg Phe Asp Glu Lys
145                 150                 155                 160

His Pro Gly Trp Leu Ile Tyr Arg Ser Met Arg Pro Met Ala Leu Ala
                165                 170                 175

Gly Lys Ile Thr Val Val Asn Pro Pro Arg Phe Lys Glu Pro Tyr Ser
            180                 185                 190

Arg Phe Trp Met Pro Pro Arg Val Ser Arg Glu Tyr Val Glu Lys Lys
        195                 200                 205

Gly Trp Arg Ile Val Val Ala His Gln Thr Arg Asn Val Pro His Ile
        210                 215                 220

Gly His Glu Met Leu Met Lys Arg Ala Met Phe Val Ala Gly Gly Glu
225                 230                 235                 240

```
Arg Pro Gly Asp Ala Val Leu Val Asn Ala Ile Ile Gly Ala Lys Arg
            245                 250                 255

Pro Gly Asp Tyr Val Asp Glu Ala Ile Leu Glu Gly His Glu Ala Leu
        260                 265                 270

Asn Lys Ala Gly Tyr Phe His Pro Asp Arg His Val Thr Met Thr
    275                 280                 285

Leu Trp Asp Met Arg Tyr Gly Asn Pro Leu Glu Ser Leu Leu His Gly
290                 295                 300

Ile Ile Arg Gln Asn Met Gly Ala Thr His His Met Phe Gly Arg Asp
305                 310                 315                 320

His Ala Ala Thr Gly Asp Tyr Asp Pro Tyr Ala Thr Gln Tyr Leu
            325                 330                 335

Trp Thr Arg Gly Leu Pro Ser Tyr Gly Leu Asn Glu Pro Pro His Met
            340                 345                 350

Thr Asp Lys Gly Leu Arg Ile Lys Pro Val Asn Leu Gly Glu Phe Ala
            355                 360                 365

Tyr Cys Pro Lys Cys Gly Glu Tyr Thr Tyr Leu Gly Met Ser Tyr Glu
    370                 375                 380

Gly Tyr Lys Glu Val Ala Leu Cys Gly His Thr Pro Glu Arg Ile Ser
385                 390                 395                 400

Gly Ser Leu Leu Arg Gly Ile Ile Glu Gly Leu Arg Pro Pro Lys
            405                 410                 415

Val Val Met Arg Pro Glu Val Tyr Asp Val Ile Val Lys Trp Trp Arg
            420                 425                 430

Val Tyr Gly Tyr Pro Tyr Val Thr Asp Lys Tyr Leu Arg Ile Lys Glu
        435                 440                 445

Gln Glu Leu Glu Val Glu Leu
    450                 455

<210> SEQ ID NO 27
<211> LENGTH: 456
<212> TYPE: PRT
<213> ORGANISM: Archaeoglobus fulgidus

<400> SEQUENCE: 27

Met Pro Leu Ile Lys Thr Pro Pro His Gly Gly Lys Leu Val Glu
1               5                   10                  15

Arg Val Val Lys Lys Arg Asp Ile Ala Glu Lys Met Ile Ala Gly Cys
            20                  25                  30

Pro Thr Tyr Glu Leu Lys Pro Thr Thr Leu Pro Asp Gly Thr Pro Ile
        35                  40                  45

Arg His Val Tyr Arg Glu Ile Met Ser Val Cys Tyr Gly Phe Phe Ser
    50                  55                  60

Pro Val Glu Gly Ser Met Val Gln Asn Glu Leu Glu Arg Val Leu Asn
65                  70                  75                  80

Glu Arg Arg Leu Leu Ser Glu Trp Ile Phe Pro Tyr Pro Ile Leu Phe
            85                  90                  95

Asp Ile Ser Glu Glu Asp Tyr Lys Ala Leu Asp Val Lys Glu Gly Asp
            100                 105                 110

Arg Leu Leu Leu Met Leu Lys Gly Gln Pro Phe Ala Thr Leu Asp Ile
        115                 120                 125

Glu Glu Val Tyr Lys Ile Asp Pro Val Asp Val Ala Thr Arg Thr Phe
    130                 135                 140

Gly Thr Pro Glu Lys Asn Pro Glu Val Val Arg Glu Pro Phe Asp Asp
```

```
                145                 150                 155                 160
Lys His Pro Gly Tyr Val Ile Tyr Lys Met His Asn Pro Ile Ile Leu
                    165                 170                 175

Ala Gly Lys Tyr Thr Ile Val Asn Glu Pro Lys Phe Lys Glu Pro Tyr
                180                 185                 190

Asp Arg Phe Trp Phe Pro Ser Lys Cys Arg Glu Val Ile Lys Asn
                    195                 200                 205

Glu Lys Lys Trp Arg Thr Val Ile Ala His Gln Thr Arg Asn Val Pro
                210                 215                 220

His Val Gly His Glu Met Leu Met Lys Cys Ala Ala Tyr Thr Gly Asp
225                 230                 235                 240

Ile Glu Pro Cys His Gly Ile Leu Val Asn Ala Ile Ile Gly Ala Lys
                    245                 250                 255

Arg Arg Gly Asp Tyr Pro Asp Glu Ala Ile Leu Glu Gly His Glu Ala
                    260                 265                 270

Val Asn Lys Tyr Gly Tyr Ile Lys Pro Glu Arg His Met Val Thr Phe
                275                 280                 285

Thr Leu Trp Asp Met Arg Tyr Gly Asn Pro Ile Glu Ser Leu Leu His
                290                 295                 300

Gly Val Ile Arg Gln Asn Met Gly Cys Thr His His Met Phe Gly Arg
305                 310                 315                 320

Asp His Ala Ala Val Gly Glu Tyr Tyr Asp Met Tyr Ala Thr Gln Ile
                    325                 330                 335

Leu Trp Ser Gln Gly Ile Pro Ser Phe Gly Phe Glu Ala Pro Pro Asn
                340                 345                 350

Glu Val Asp Tyr Gly Leu Lys Ile Ile Pro Gln Asn Met Ala Glu Phe
                355                 360                 365

Trp Tyr Cys Pro Ile Cys Gln Glu Ile Ala Tyr Ser Glu Asn Cys Gly
                370                 375                 380

His Thr Asp Ala Lys Gln Lys Phe Ser Gly Ser Phe Leu Arg Gly Met
385                 390                 395                 400

Val Ala Glu Gly Val Phe Pro Pro Arg Val Val Met Arg Pro Glu Val
                    405                 410                 415

Tyr Lys Gln Ile Val Lys Trp Trp Lys Val Tyr Asn Tyr Pro Phe Val
                420                 425                 430

Asn Arg Lys Tyr Leu Glu Leu Lys Asn Lys Glu Leu Glu Ile Asp Leu
                435                 440                 445

Pro Ala Met Glu Val Pro Lys Ala
                450                 455

<210> SEQ ID NO 28
<211> LENGTH: 573
<212> TYPE: PRT
<213> ORGANISM: Penicillium chrysogenum

<400> SEQUENCE: 28

Met Ala Asn Ala Pro His Gly Gly Val Leu Lys Asp Leu Leu Ala Arg
1                   5                   10                  15

Asp Ala Pro Arg Gln Ala Glu Leu Ala Ala Glu Ala Glu Ser Leu Pro
                20                  25                  30

Ala Val Thr Leu Thr Glu Arg Gln Leu Cys Asp Leu Glu Leu Ile Met
                35                  40                  45

Asn Gly Gly Phe Ser Pro Leu Glu Gly Phe Met Asn Gln Ala Asp Tyr
            50                  55                  60
```

-continued

```
Asp Arg Val Cys Glu Asp Asn Arg Leu Ala Asp Gly Asn Val Phe Ser
 65                  70                  75                  80

Met Pro Ile Thr Leu Asp Ala Ser Gln Glu Val Ile Asp Glu Lys Lys
                 85                  90                  95

Leu Gln Ala Ala Ser Arg Ile Thr Leu Arg Asp Phe Arg Asp Asp Arg
            100                 105                 110

Asn Leu Ala Ile Leu Thr Ile Asp Asp Ile Tyr Arg Pro Asp Lys Thr
            115                 120                 125

Lys Glu Ala Lys Leu Val Phe Gly Gly Asp Pro Glu His Pro Ala Ile
130                 135                 140

Val Tyr Leu Asn Asn Thr Val Lys Glu Phe Tyr Ile Gly Gly Lys Ile
145                 150                 155                 160

Glu Ala Val Asn Lys Leu Asn His Tyr Asp Tyr Val Ala Leu Arg Tyr
                165                 170                 175

Thr Pro Ala Glu Leu Arg Val His Phe Asp Lys Leu Gly Trp Ser Arg
            180                 185                 190

Val Val Ala Phe Gln Thr Arg Asn Pro Met His Arg Ala His Arg Glu
            195                 200                 205

Leu Thr Val Arg Ala Ala Arg Ser Arg Gln Ala Asn Val Leu Ile His
    210                 215                 220

Pro Val Val Gly Leu Thr Lys Pro Gly Asp Ile Asp His Phe Thr Arg
225                 230                 235                 240

Val Arg Ala Tyr Gln Ala Leu Leu Pro Arg Tyr Pro Asn Gly Met Ala
                245                 250                 255

Val Leu Gly Leu Leu Gly Leu Ala Met Arg Met Gly Gly Pro Arg Glu
            260                 265                 270

Ala Ile Trp His Ala Ile Arg Lys Asn His Gly Ala Thr His Phe
            275                 280                 285

Ile Val Gly Arg Asp His Ala Gly Pro Gly Ser Asn Ser Lys Gly Glu
    290                 295                 300

Asp Phe Tyr Gly Pro Tyr Asp Ala Gln His Ala Val Glu Lys Tyr Lys
305                 310                 315                 320

Asp Glu Leu Gly Ile Glu Val Val Glu Phe Gln Met Val Thr Tyr Leu
                325                 330                 335

Pro Asp Thr Asp Glu Tyr Arg Pro Val Asp Gln Val Pro Ala Gly Val
            340                 345                 350

Lys Thr Leu Asn Ile Ser Gly Thr Glu Leu Arg Arg Arg Leu Arg Ser
            355                 360                 365

Gly Ala His Ile Pro Glu Trp Phe Ser Tyr Pro Glu Val Val Lys Ile
    370                 375                 380

Leu Arg Glu Ser Asn Pro Pro Arg Ala Thr Gln Gly Phe Thr Ile Phe
385                 390                 395                 400

Leu Thr Gly Tyr Met Asn Ser Gly Lys Asp Ala Ile Ala Arg Ala Leu
                405                 410                 415

Gln Val Thr Leu Asn Gln Gln Gly Gly Arg Ser Val Ser Leu Leu Leu
            420                 425                 430

Gly Asp Thr Val Arg His Glu Leu Ser Ser Glu Leu Gly Phe Thr Arg
            435                 440                 445

Glu Asp Arg His Thr Asn Ile Gln Arg Ile Ala Phe Val Ala Thr Glu
    450                 455                 460

Leu Thr Arg Ala Gly Ala Ala Val Ile Ala Ala Pro Ile Ala Pro Tyr
465                 470                 475                 480

Glu Glu Ser Arg Lys Phe Ala Arg Asp Ala Val Ser Gln Ala Gly Ser
```

```
                    485                 490                 495
Phe Phe Leu Val His Val Ala Thr Pro Leu Glu His Cys Glu Gln Ser
            500                 505                 510
Asp Lys Arg Gly Ile Tyr Ala Ala Arg Arg Gly Glu Ile Lys Gly
            515                 520                 525
Phe Thr Gly Val Asp Asp Pro Tyr Glu Thr Pro Glu Lys Ala Asp Leu
            530                 535                 540
Val Val Asp Phe Ser Lys Gln Ser Val Arg Ser Ile Val His Glu Ile
545                 550                 555                 560
Ile Leu Val Leu Glu Ser Gln Gly Phe Leu Glu Arg Gln
                565                 570

<210> SEQ ID NO 29
<211> LENGTH: 389
<212> TYPE: PRT
<213> ORGANISM: Aeropyrum pernix

<400> SEQUENCE: 29

Met Gly Cys Ser Val Gly Leu Val Ser Arg Pro His Gly Gly Arg Leu
1               5                   10                  15
Val Arg Arg Val Leu Ser Gly Arg Arg Glu Ile Phe Glu Ser Gln
            20                  25                  30
Tyr Arg Glu Met Pro Arg Leu Glu Val Pro Leu Glu Arg Ala Ile Asp
            35                  40                  45
Ala Glu Asp Leu Ala Arg Gly Val Phe Ser Pro Leu Glu Gly Phe Met
        50                  55                  60
Val Glu Asp Asp Tyr Leu Ser Val Leu Ser Arg Met Arg Leu Ser Asn
65                  70                  75                  80
Asp Leu Pro Trp Thr Ile Pro Ile Val Leu Asp Ala Asn Arg Glu Trp
                85                  90                  95
Val Leu Asn Glu Gly Val Ser Ala Gly Asp Asp Ile Ile Leu Thr Tyr
            100                 105                 110
His Gly Leu Pro Ile Ala Val Leu Thr Leu Glu Asp Ile Tyr Ser Trp
            115                 120                 125
Asp Lys Gly Leu His Ala Glu Lys Val Phe Lys Thr Arg Asp Pro Asn
        130                 135                 140
His Pro Gly Val Glu Ala Thr Tyr Lys Arg Gly Asp Ile Leu Leu Gly
145                 150                 155                 160
Gly Arg Leu Glu Leu Ile Gln Gly Pro Pro Asn Pro Leu Glu Arg Tyr
                165                 170                 175
Thr Leu Trp Pro Val Glu Thr Arg Val Leu Phe Lys Glu Lys Gly Trp
            180                 185                 190
Arg Thr Val Ala Ala Phe Gln Thr Arg Asn Val Pro His Leu Gly His
            195                 200                 205
Glu Tyr Val Gln Lys Ala Ala Leu Thr Phe Val Asp Gly Leu Leu Val
        210                 215                 220
His Pro Leu Ala Gly Trp Lys Lys Arg Gly Asp Tyr Arg Asp Glu Val
225                 230                 235                 240
Ile Ile Arg Ala Tyr Glu Ala Leu Ile Thr His Tyr Tyr Pro Arg Gly
                245                 250                 255
Val Val Val Leu Ser Val Leu Arg Met Asn Met Asn Tyr Ala Gly Pro
            260                 265                 270
Arg Glu Ala Val His His Ala Ile Val Arg Lys Asn Phe Gly Ala Thr
            275                 280                 285
```

```
His Phe Ile Val Gly Arg Asp His Ala Gly Val Gly Ser Tyr Tyr Gly
    290                 295                 300

Pro Tyr Glu Ala Trp Glu Ile Phe Arg Glu Phe Pro Asp Leu Gly Ile
305                 310                 315                 320

Thr Pro Leu Phe Val Arg Glu Ala Tyr Tyr Cys Arg Arg Cys Gly Gly
                325                 330                 335

Met Val Asn Glu Lys Val Cys Pro His Gly Asp Glu Tyr Arg Val Arg
            340                 345                 350

Ile Ser Gly Thr Arg Leu Arg Glu Met Leu Gly Arg Gly Glu Arg Pro
        355                 360                 365

Pro Glu Tyr Met Met Arg Pro Glu Val Ala Asp Ala Ile Ile Ser His
    370                 375                 380

Pro Asp Pro Phe Ile
385

<210> SEQ ID NO 30
<211> LENGTH: 511
<212> TYPE: PRT
<213> ORGANISM: Saccharomyces cerevisiae

<400> SEQUENCE: 30

Met Pro Ala Pro His Gly Gly Ile Leu Gln Asp Leu Ile Ala Arg Asp
1               5                   10                  15

Ala Leu Lys Lys Asn Glu Leu Leu Ser Glu Ala Gln Ser Ser Asp Ile
            20                  25                  30

Leu Val Trp Asn Leu Thr Pro Arg Gln Leu Cys Asp Ile Glu Leu Ile
        35                  40                  45

Leu Asn Gly Gly Phe Ser Pro Leu Thr Gly Phe Leu Asn Glu Asn Asp
    50                  55                  60

Tyr Ser Ser Val Val Thr Asp Ser Arg Leu Ala Asp Gly Thr Leu Trp
65                  70                  75                  80

Thr Ile Pro Ile Thr Leu Asp Val Asp Glu Ala Phe Ala Asn Gln Ile
                85                  90                  95

Lys Pro Asp Thr Arg Ile Ala Leu Phe Gln Asp Asp Glu Ile Pro Ile
            100                 105                 110

Ala Ile Leu Thr Val Gln Asp Val Tyr Lys Pro Asn Lys Thr Ile Glu
        115                 120                 125

Ala Glu Lys Val Phe Arg Gly Asp Pro Glu His Pro Ala Ile Ser Tyr
    130                 135                 140

Leu Phe Asn Val Ala Gly Asp Tyr Tyr Val Gly Gly Ser Leu Glu Ala
145                 150                 155                 160

Ile Gln Leu Pro Gln His Tyr Asp Tyr Pro Gly Leu Arg Lys Thr Pro
                165                 170                 175

Ala Gln Leu Arg Leu Glu Phe Gln Ser Arg Gln Trp Asp Arg Val Val
            180                 185                 190

Ala Phe Gln Thr Arg Asn Pro Met His Arg Ala His Arg Glu Leu Thr
        195                 200                 205

Val Arg Ala Ala Arg Glu Ala Asn Ala Lys Val Leu Ile His Pro Val
    210                 215                 220

Val Gly Leu Thr Lys Pro Gly Asp Ile Asp His His Thr Arg Val Arg
225                 230                 235                 240

Val Tyr Gln Glu Ile Ile Lys Arg Tyr Pro Asn Gly Ile Ala Phe Leu
                245                 250                 255

Ser Leu Leu Pro Leu Ala Met Arg Met Ser Gly Asp Arg Glu Ala Val
            260                 265                 270
```

```
Trp His Ala Ile Ile Arg Lys Asn Tyr Gly Ala Ser His Phe Ile Val
            275                 280                 285

Gly Arg Asp His Ala Gly Pro Gly Lys Asn Ser Lys Gly Val Asp Phe
        290                 295                 300

Tyr Gly Pro Tyr Asp Ala Gln Glu Leu Val Glu Ser Tyr Lys His Glu
305                 310                 315                 320

Leu Asp Ile Glu Val Val Pro Phe Arg Met Val Thr Tyr Leu Pro Asp
                325                 330                 335

Glu Asp Arg Tyr Ala Pro Ile Asp Gln Ile Asp Thr Thr Lys Thr Arg
            340                 345                 350

Thr Leu Asn Ile Ser Gly Thr Glu Leu Arg Arg Leu Arg Val Gly
            355                 360                 365

Gly Glu Ile Pro Glu Trp Phe Ser Tyr Pro Glu Val Val Lys Ile Leu
            370                 375                 380

Arg Glu Ser Asn Pro Pro Arg Pro Lys Gln Gly Phe Ser Ile Val Leu
385                 390                 395                 400

Gly Asn Ser Leu Thr Val Ser Arg Glu Gln Leu Ser Ile Ala Leu Leu
                405                 410                 415

Ser Thr Phe Leu Gln Phe Gly Gly Gly Arg Tyr Tyr Lys Ile Phe Glu
                420                 425                 430

His Asn Asn Lys Thr Glu Leu Leu Ser Leu Ile Gln Asp Phe Ile Gly
            435                 440                 445

Ser Gly Ser Gly Leu Ile Ile Pro Asn Gln Trp Glu Asp Asp Lys Asp
            450                 455                 460

Ser Val Val Gly Lys Gln Asn Val Tyr Leu Leu Asp Thr Ser Ser Ser
465                 470                 475                 480

Ala Asp Ile Gln Leu Glu Ser Ala Asp Glu Pro Ile Ser His Ile Val
                485                 490                 495

Gln Lys Val Val Leu Phe Leu Glu Asp Asn Gly Phe Phe Val Phe
                500                 505                 510

<210> SEQ ID NO 31
<211> LENGTH: 309
<212> TYPE: PRT
<213> ORGANISM: Thermomonospora fusca

<400> SEQUENCE: 31

Met Ser Gln Val Ser Asp Ala Val Gly Arg Tyr Gln Leu Ser Gln Leu
 1               5                  10                  15

Asp Phe Leu Glu Ala Glu Ala Ile Phe Ile Met Arg Glu Val Ala Ala
                20                  25                  30

Glu Phe Glu Arg Pro Val Leu Leu Phe Ser Gly Gly Lys Asp Ser Val
            35                  40                  45

Val Met Leu Arg Ile Ala Glu Lys Ala Phe Trp Pro Ala Pro Ile Pro
        50                  55                  60

Phe Pro Val Met His Val Asp Thr Gly His Asn Phe Pro Glu Val Ile
 65                 70                  75                  80

Glu Phe Arg Asp Lys Arg Val Ala Glu Leu Gly Val Arg Leu Ile Val
                85                  90                  95

Ala Ser Val Gln Asp Leu Ile Asp Ala Gly Lys Val Val Glu Pro Lys
                100                 105                 110

Gly Arg Trp Ala Ser Arg Asn Arg Leu Gln Thr Ala Ala Leu Leu Glu
            115                 120                 125
```

-continued

```
Ala Ile Glu Lys Tyr Gly Phe Asp Ala Ala Phe Gly Gly Ala Arg Arg
    130                 135                 140
Asp Glu Glu Lys Ala Arg Ala Lys Glu Arg Val Phe Ser Phe Arg Asp
145                 150                 155                 160
Glu Phe Gly Gln Trp Asp Pro Lys Asn Gln Arg Pro Glu Leu Trp Asn
                165                 170                 175
Leu Tyr Asn Thr Arg Val His Arg Gly Glu Asn Ile Arg Val Phe Pro
            180                 185                 190
Leu Ser Asn Trp Thr Glu Leu Asp Val Trp His Tyr Ile Arg Arg Glu
        195                 200                 205
Gly Leu Arg Leu Pro Ser Ile Tyr Phe Ala His Arg Arg Val Phe
    210                 215                 220
Glu Arg Asp Gly Ile Leu Leu Pro Asp Ser Pro Tyr Val Thr Arg Asp
225                 230                 235                 240
Glu Asp Glu Glu Val Phe Glu Ala Ser Val Arg Tyr Arg Thr Val Gly
                245                 250                 255
Asp Met Thr Cys Thr Gly Ala Val Leu Ser Thr Ala Thr Thr Leu Asp
            260                 265                 270
Glu Val Ile Ala Glu Ile Ala Ala Thr Arg Ile Thr Glu Arg Gly Gln
        275                 280                 285
Thr Arg Ala Asp Asp Arg Gly Ser Glu Ala Ala Met Glu Glu Arg Lys
    290                 295                 300
Arg Glu Gly Tyr Phe
305
```